(12) United States Patent
Takada et al.

(10) Patent No.: US 9,550,825 B2
(45) Date of Patent: Jan. 24, 2017

(54) HUMANIZED ANTI-HMGB1 ANTIBODY OR ANTIGEN-BINDING FRAGMENT THEREOF

(71) Applicants: EVEC INC., Hokkaido (JP); NATIONAL UNIVERSITY CORPORATION OKAYAMA UNIVERSITY, Okayama (JP)

(72) Inventors: Kenzo Takada, Hokkaido (JP); Takashi Torashima, Hokkaido (JP); Masahiro Nishibori, Okayama (JP)

(73) Assignees: EVEC INC., Hokkaido (JP); NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 0 days.

(21) Appl. No.: 14/761,152

(22) PCT Filed: Dec. 6, 2013

(86) PCT No.: PCT/JP2013/082860
§ 371 (c)(1),
(2) Date: Jul. 15, 2015

(87) PCT Pub. No.: WO2014/115430
PCT Pub. Date: Jul. 31, 2014

(65) Prior Publication Data
US 2015/0361164 A1    Dec. 17, 2015

(30) Foreign Application Priority Data
Jan. 28, 2013  (JP) ................................ 2013-013602

(51) Int. Cl.
C07K 16/18 (2006.01)
A61K 39/395 (2006.01)
C07K 16/24 (2006.01)
A61K 39/00 (2006.01)

(52) U.S. Cl.
CPC .............. *C07K 16/18* (2013.01); *C07K 16/24* (2013.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 2009/0175878 A1 | 7/2009 | Nishibori et al. |
| 2009/0252739 A1 | 10/2009 | Nishibori et al. |
| 2009/0297546 A1 | 12/2009 | Yamada et al. |
| 2010/0172909 A1 | 7/2010 | Nishibori et al. |
| 2012/0183556 A1 | 7/2012 | Nishibori et al. |

FOREIGN PATENT DOCUMENTS

| | | |
|---|---|---|
| EP | 1946774 A1 | 7/2008 |
| WO | 0047104 A3 | 8/2000 |
| WO | 02074337 A1 | 9/2002 |
| WO | 2004046345 A2 | 6/2004 |
| WO | 2005026209 A2 | 3/2005 |
| WO | 2007001422 A2 | 1/2007 |
| WO | 2007049468 A1 | 5/2007 |
| WO | 2007135992 A1 | 11/2007 |
| WO | 2008075788 A1 | 6/2008 |
| WO | 2011037227 A1 | 3/2011 |
| WO | 2012074043 A1 | 6/2012 |
| WO | 2012136250 A1 | 10/2012 |

OTHER PUBLICATIONS

Andersson et al., "HMGB1 Is a Therapeutic Target for Sterile Inflammation and Infection," The Annual Review of Immunology, 2011, (vol. 29) pp. 139-162.
Muhammad et al., "The HMGB1 Receptor RAGE Mediates Ischemic Brain Damage," The Journal of Neuroscience, 2008, (vol. 28) pp. 12023-12031.
Lutterloh et al., "Inhibition of the RAGE products increases survival in experimental models of severe sepsis and systemic infection," Critical Care, 2007, (vol. 11) pR122.
Zhang et al., "Tanshinone IIA Sodium Sulfonate Facilitates Endocytic HMGB1 Uptake," Biochemical Pharmacology, 2012, (vol. 84) pp. 1492-1500.
Abraham et al., "HMG-1 as a Mediator of Acute Lung Inflammation," Cutting Edge, 2000, (vol. 165) pp. 2950-2954.
Schierbeck et al., "Monoclonal Anti-HMGB1 (High Mobility Group Box Chromosomal Protein 1) Antibody Protection in Two Experimental Arthritis Models," Molecular Medical, 2011, (vol. 17) pp. 1039-1044.
Kim et al., "HMGB1, a Novel Cytokine-Like Mediator Linking Acute Neuronal Death and Delayed Neuroinflammation in the Postischemic Brain," The Journal of Neuroscience, 2006, (vol. 26) pp. 6413-6421.
Gao et al., "TLR4 Mediates Early Graft Failure After Intraportal Islet Transplantation," American Journal of Transplantation, 2010, (vol. 10) pp. 1588-1596.

(Continued)

*Primary Examiner* — Kimberly A. Ballard
*Assistant Examiner* — Stacey N MacFarlane
(74) *Attorney, Agent, or Firm* — EIP US LLP

(57) ABSTRACT

The present invention provides a humanized anti-HMGB1 antibody which specifically binds to a sequence consisting of the C-terminal 8 amino acid residues (EEEDDDDE) of HMGB1 protein and is effective for treatment or prevention of various inflammatory diseases related to this protein, as well as an antigen-binding fragment thereof. The present invention also provides a pharmaceutical composition comprising such an antibody or antigen-binding fragment thereof.

14 Claims, 14 Drawing Sheets

(56) References Cited

OTHER PUBLICATIONS

Nakamura et al., "Neuropathic Pain in Rats with a Partial Sciatic Nerve Ligation is Alleviated by Intravenous Injection of Monoclonal Antibody to High Mobility Group Box-1," Plos ONE, 2013, (vol. 8) e73640.
Liu et al., "Anti-high Mobility Group Box 1 Monoclonal Antibody Ameliorates Brain Infarction Induced by Transient Ischemia in Rats," The FASEB Journal, 2007, (vol. 21) pp. 3904-3916.
Zhang et al., "Anti-high Mobility Group Box-1 Monoclonal Antibody Protects the Blood-Brian Barrier From Ischemia-Induced Disruption in Rats," Stroke: Journal of the American Heart Association, 2011, (vol. 42) pp. 1420-1428.
Kanellakis et al., "High-Mobility Group Box Protein 1 Neutralization Reduces Development of Diet-Induced Atherosclerosis in Apolipoprotein E-Deficient Mice," Arteriosclerosis, Thrombosis, and Vascular Biology: Journal of the American Heart Association, 2011, (vol. 31) pp. 313-319.
Okuma et al., "Anti-High Mobility Group Box-1 Antibody Therapy for Traumatic Brain Injury." Annals of Neurology (2012). (vol. 72) pp. 373-384.
International Search Report of PCT/JP2013/082860 dated Mar. 11, 2014.
Extended European Search Report issued in related case EP 13872417.4, dated Jun. 9, 2016.
Tian, Jane et al., "Toll-like receotir 9-dependent activation by DNA-containing immune complexes is mediated by HMGB1 and RAGE", Nature Immunology, Nature Publishing Group, GB May 1, 2007.

Fig. 1

|  | OD 450 nm |
|---|---|
| POSITIVE CONTROL (HYBRIDOMA-DERIVED ANTIBODY, 500 ng/ml) | 1.777 |
| NEGATIVE CONTROL (10% FCS-DMEM) | 0.052 |
| RAT H CHAIN + RAT L CHAIN (CULTURE SUPERNATANT) | 3.414 |

Fig. 2

|  | OD 450 nm |
|---|---|
| POSITIVE CONTROL (#10-22, 500 ng/ml) | 1.250 |
| NEGATIVE CONTROL (10% FCS-DMEM) | 0.043 |
| #10-22 CHIMERA (CULTURE SUPERNATANT) | 2.787 |

1. His-HMGB1 (full length)
2. His-A-Box + B-Box
3. His-A-Box + C-tail
4. His-B-Box + C-tail
5. His-A-Box
6. His-B-Box
7. His-C-tail Fig. 16-a
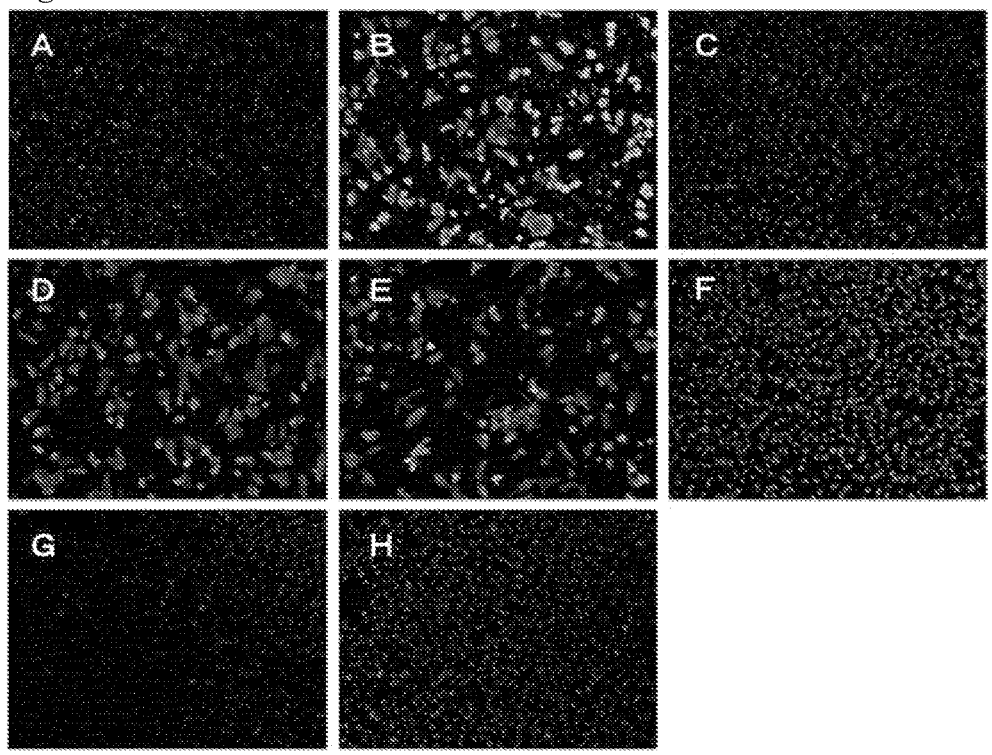
Fig. 16-b
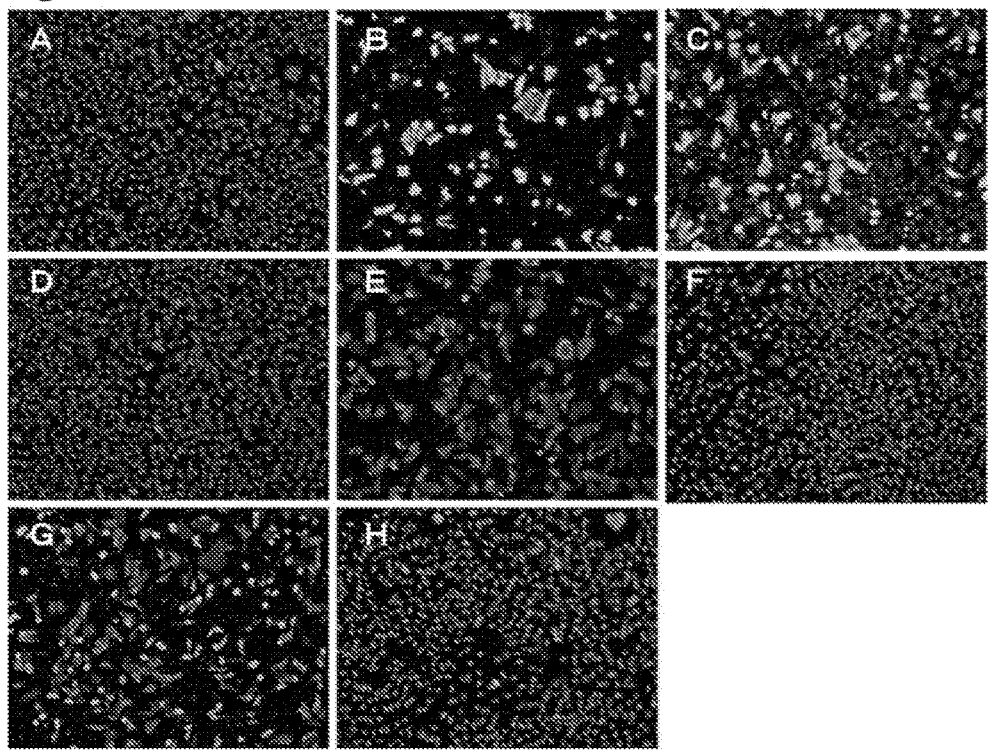

Fig. 16-c
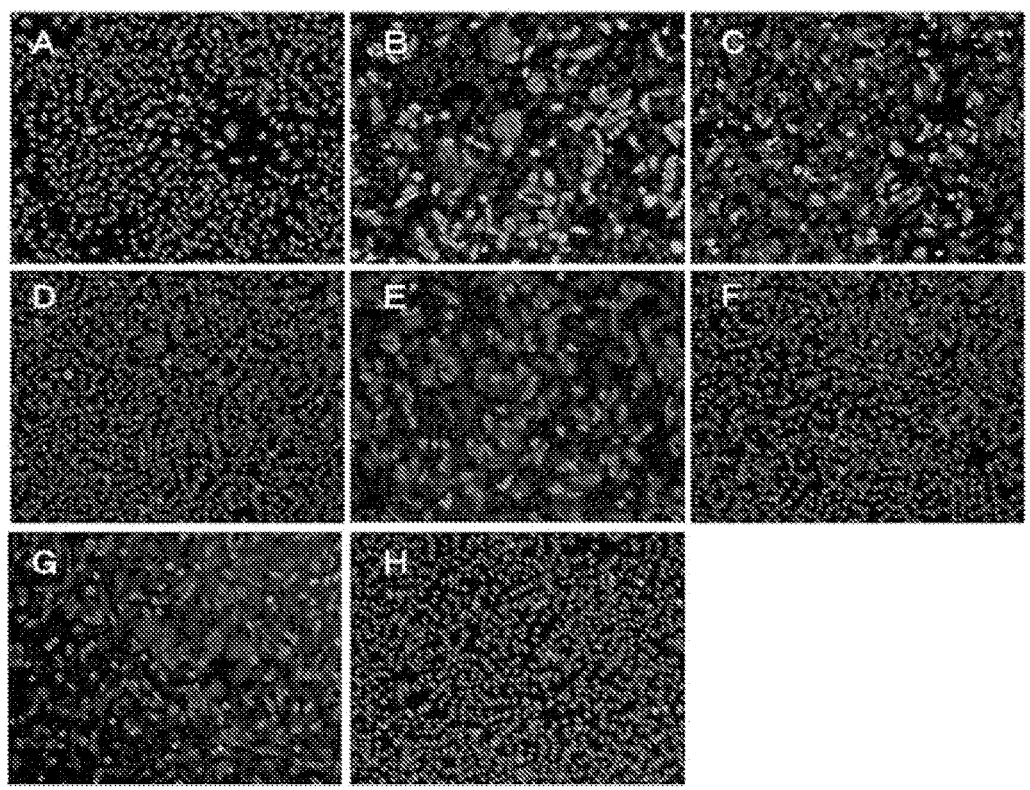

Fig. 17-a
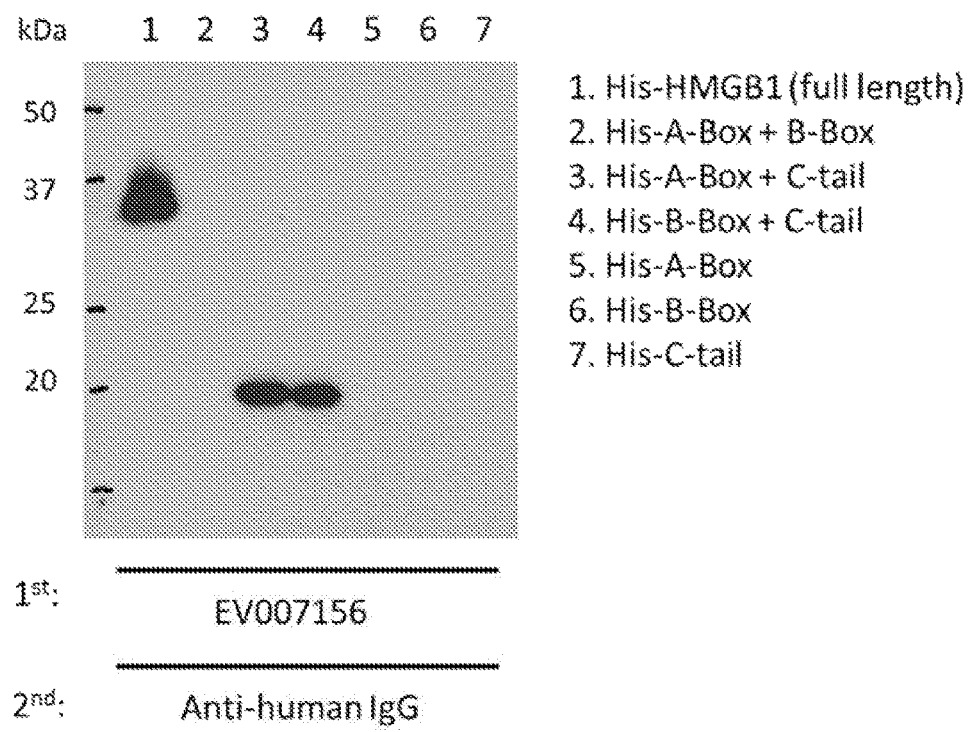
1. His-HMGB1 (full length)
2. His-A-Box + B-Box
3. His-A-Box + C-tail
4. His-B-Box + C-tail
5. His-A-Box
6. His-B-Box
7. His-C-tail
1st: EV007156
2nd: Anti-human IgG
Fig. 17-b
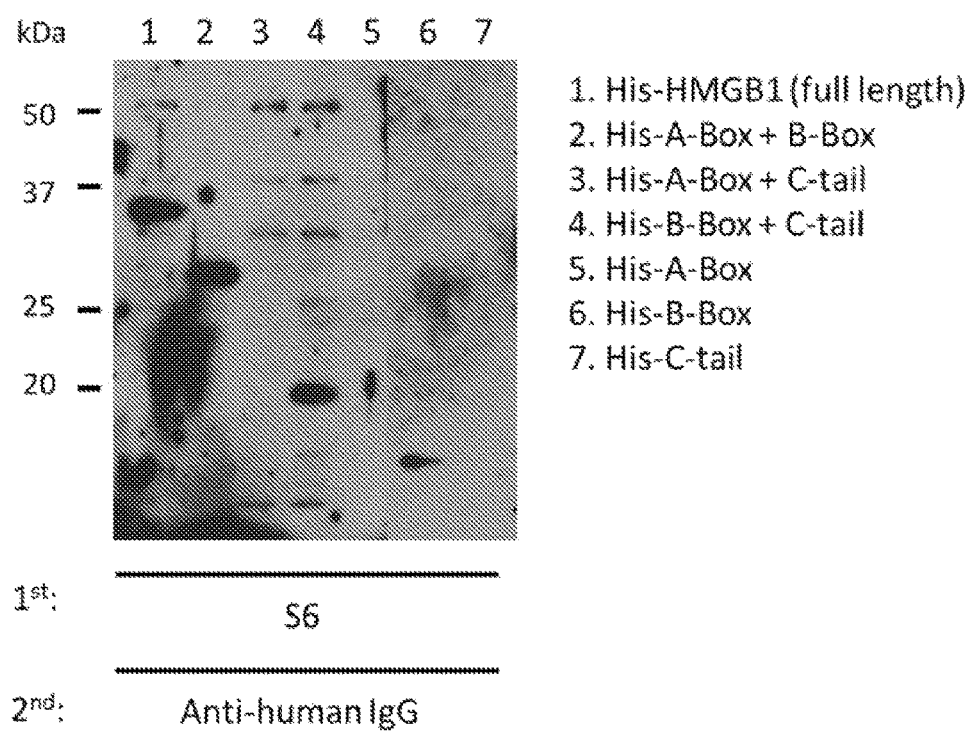
1. His-HMGB1 (full length)
2. His-A-Box + B-Box
3. His-A-Box + C-tail
4. His-B-Box + C-tail
5. His-A-Box
6. His-B-Box
7. His-C-tail
1st: S6
2nd: Anti-human IgG

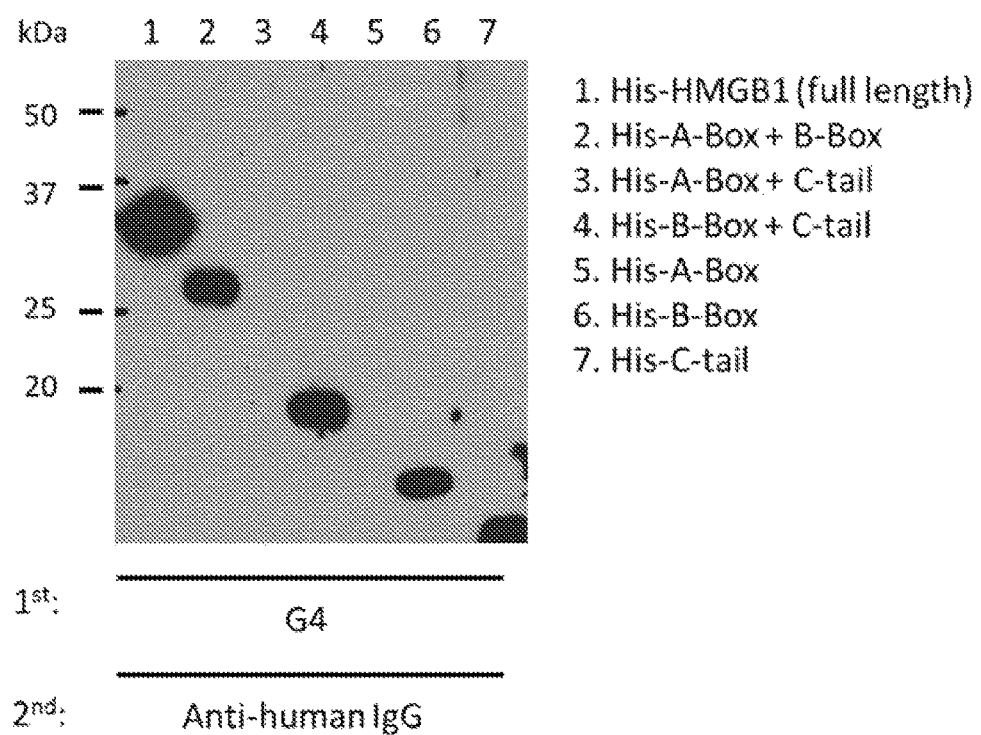
Fig. 17-c

SEQUENCE LISTING

<160> NUMBER OF SEQ ID NOS: 60

<210> SEQ ID NO 1
<211> LENGTH: 465
<212> TYPE: PRT
<213> ORGANISM: Rattus norvegicus

<400> SEQUENCE: 1

Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Lys Glu Ser Leu Lys Ile Ser Cys Ala Ala Ser Gly Phe Thr Phe Ser
        35                  40                  45

Asn Ala Ala Met Tyr Trp Val Arg Gln Ala Pro Gly Lys Gly Leu Glu
    50                  55                  60

Trp Val Ala Arg Ile Arg Thr Lys Pro Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Met Val Tyr Leu Gln Met Asp Asn Leu Lys Thr Glu Asp Thr Ala
            100                 105                 110

Met Tyr Tyr Cys Thr Ala Pro Arg Arg Thr Glu Gly Ile Val Ser Ser
        115                 120                 125

Gly Val Asp Tyr Trp Gly Gln Gly Val Met Val Thr Val Ser Ser Ala
    130                 135                 140

Glu Thr Thr Ala Pro Ser Val Tyr Pro Leu Ala Pro Gly Thr Ala Leu
145                 150                 155                 160

Lys Ser Asn Ser Met Val Thr Leu Gly Cys Leu Val Lys Gly Tyr Phe
                165                 170                 175

Pro Glu Pro Val Thr Val Thr Trp Asn Ser Gly Ala Leu Ser Ser Gly
            180                 185                 190

Val His Thr Phe Pro Ala Val Leu Gln Ser Gly Leu Tyr Thr Leu Thr
        195                 200                 205

Ser Ser Val Thr Val Pro Ser Ser Thr Trp Ser Ser Gln Ala Val Thr
    210                 215                 220

Cys Asn Val Ala His Pro Ala Ser Ser Thr Lys Val Asp Lys Lys Ile
225                 230                 235                 240

Val Pro Arg Glu Cys Asn Pro Cys Gly Cys Thr Gly Ser Glu Val Ser
                245                 250                 255

Ser Val Phe Ile Phe Pro Pro Lys Thr Lys Asp Val Leu Thr Ile Thr
            260                 265                 270

Leu Thr Pro Lys Val Thr Cys Val Val Asp Ile Ser Gln Asn Asp
        275                 280                 285

Pro Glu Val Arg Phe Ser Trp Phe Ile Asp Asp Val Glu Val His Thr
    290                 295                 300

Ala Gln Thr His Ala Pro Glu Lys Gln Ser Asn Ser Thr Leu Arg Ser
305                 310                 315                 320

Val Ser Glu Leu Pro Ile Val His Arg Asp Trp Leu Asn Gly Lys Thr
                325                 330                 335

Phe Lys Cys Lys Val Asn Ser Gly Ala Phe Pro Ala Pro Ile Glu Lys
            340                 345                 350

Ser Ile Ser Lys Pro Glu Gly Thr Pro Arg Gly Pro Gln Val Tyr Thr
        355                 360                 365

```
Met Ala Pro Pro Lys Glu Glu Met Thr Gln Ser Gln Val Ser Ile Thr
    370                 375                 380

Cys Met Val Lys Gly Phe Tyr Pro Pro Asp Ile Tyr Thr Glu Trp Lys
385                 390                 395                 400

Met Asn Gly Gln Pro Gln Glu Asn Tyr Lys Asn Thr Pro Pro Thr Met
                405                 410                 415

Asp Thr Asp Gly Ser Tyr Phe Leu Tyr Ser Lys Leu Asn Val Lys Lys
            420                 425                 430

Glu Thr Trp Gln Gln Gly Asn Thr Phe Thr Cys Ser Val Leu His Glu
            435                 440                 445

Gly Leu His Asn His His Thr Glu Lys Ser Leu Ser His Ser Pro Gly
    450                 455                 460

Lys
465

<210> SEQ ID NO 2
<211> LENGTH: 232
<212> TYPE: PRT
<213> ORGANISM: Rattus norvegicus

<400> SEQUENCE: 2

Met Ser Trp Thr Ser Leu Leu Pro Leu Leu Ser Leu Tyr Ala Gly
1               5                   10                  15

Ser Val Thr Ser Tyr Glu Leu Ile Gln Pro Ser Ala Ser Val Thr
                20                  25                  30

Leu Gly Asn Thr Val Ser Ile Thr Cys Ser Gly Asp Glu Leu Pro Lys
            35                  40                  45

Arg Tyr Ala Tyr Trp Tyr Gln Gln Lys Pro Asp Lys Ser Ile Val Arg
50                  55                  60

Val Ile Tyr Lys Asp Ser Glu Arg Pro Ser Gly Ile Ser Asp Arg Phe
65                  70                  75                  80

Ser Gly Ser Ser Ser Gly Thr Thr Ala Thr Leu Thr Ile Arg Asp Thr
                85                  90                  95

Gln Ala Glu Asp Glu Ala Asp Tyr Tyr Cys His Ser Thr Tyr Ser Asp
            100                 105                 110

Asp Lys Leu Pro Val Phe Gly Gly Gly Thr Lys Leu Thr Val Leu Gly
            115                 120                 125

Gln Pro Lys Ser Thr Pro Thr Leu Thr Val Phe Pro Pro Ser Thr Glu
    130                 135                 140

Glu Leu Gln Gly Asn Lys Ala Thr Leu Val Cys Leu Ile Ser Asp Phe
145                 150                 155                 160

Tyr Pro Ser Asp Val Glu Val Ala Trp Lys Ala Asn Gly Ala Pro Ile
                165                 170                 175

Ser Gln Gly Val Asp Thr Ala Asn Pro Thr Lys Gln Gly Asn Lys Tyr
            180                 185                 190

Ile Ala Ser Ser Phe Leu Arg Leu Thr Ala Glu Gln Trp Arg Ser Arg
            195                 200                 205

Asn Ser Phe Thr Cys Gln Val Thr His Glu Gly Asn Thr Val Glu Lys
    210                 215                 220

Ser Leu Ser Pro Ala Glu Cys Ser
225                 230

<210> SEQ ID NO 3
<211> LENGTH: 447
<212> TYPE: PRT
<213> ORGANISM: Rattus norvegicus
```

<400> SEQUENCE: 3

```
Ala Val Gln Leu Val Glu Ser Gly Gly Leu Val Gln Pro Lys Glu
 1               5                  10                  15
Ser Leu Lys Ile Ser Cys Ala Ala Ser Gly Phe Thr Phe Ser Asn Ala
            20                  25                  30
Ala Met Tyr Trp Val Arg Gln Ala Pro Gly Lys Gly Leu Glu Trp Val
        35                  40                  45
Ala Arg Ile Arg Thr Lys Pro Asn Asn Tyr Ala Thr Tyr Tyr Ala Asp
50                  55                  60
Ser Val Lys Gly Arg Phe Thr Ile Ser Arg Asp Asp Ser Lys Ser Met
65                  70                  75                  80
Val Tyr Leu Gln Met Asp Asn Leu Lys Thr Glu Asp Thr Ala Met Tyr
                85                  90                  95
Tyr Cys Thr Ala Pro Arg Arg Thr Glu Gly Ile Val Ser Ser Gly Val
            100                 105                 110
Asp Tyr Trp Gly Gln Gly Val Met Val Thr Val Ser Ser Ala Glu Thr
        115                 120                 125
Thr Ala Pro Ser Val Tyr Pro Leu Ala Pro Gly Thr Ala Leu Lys Ser
130                 135                 140
Asn Ser Met Val Thr Leu Gly Cys Leu Val Lys Gly Tyr Phe Pro Glu
145                 150                 155                 160
Pro Val Thr Val Thr Trp Asn Ser Gly Ala Leu Ser Ser Gly Val His
                165                 170                 175
Thr Phe Pro Ala Val Leu Gln Ser Gly Leu Tyr Thr Leu Thr Ser Ser
            180                 185                 190
Val Thr Val Pro Ser Ser Thr Trp Ser Ser Gln Ala Val Thr Cys Asn
        195                 200                 205
Val Ala His Pro Ala Ser Ser Thr Lys Val Asp Lys Lys Ile Val Pro
210                 215                 220
Arg Glu Cys Asn Pro Cys Gly Cys Thr Gly Ser Glu Val Ser Ser Val
225                 230                 235                 240
Phe Ile Phe Pro Pro Lys Thr Lys Asp Val Leu Thr Ile Thr Leu Thr
                245                 250                 255
Pro Lys Val Thr Cys Val Val Asp Ile Ser Gln Asn Asp Pro Glu
            260                 265                 270
Val Arg Phe Ser Trp Phe Ile Asp Asp Val Glu Val His Thr Ala Gln
        275                 280                 285
Thr His Ala Pro Glu Lys Gln Ser Asn Ser Thr Leu Arg Ser Val Ser
290                 295                 300
Glu Leu Pro Ile Val His Arg Asp Trp Leu Asn Gly Lys Thr Phe Lys
305                 310                 315                 320
Cys Lys Val Asn Ser Gly Ala Phe Pro Ala Pro Ile Glu Lys Ser Ile
                325                 330                 335
Ser Lys Pro Glu Gly Thr Pro Arg Gly Pro Gln Val Tyr Thr Met Ala
            340                 345                 350
Pro Pro Lys Glu Glu Met Thr Gln Ser Gln Val Ser Ile Thr Cys Met
        355                 360                 365
Val Lys Gly Phe Tyr Pro Pro Asp Ile Tyr Thr Glu Trp Lys Met Asn
370                 375                 380
Gly Gln Pro Gln Glu Asn Tyr Lys Asn Thr Pro Pro Thr Met Asp Thr
385                 390                 395                 400
Asp Gly Ser Tyr Phe Leu Tyr Ser Lys Leu Asn Val Lys Lys Glu Thr
```

-continued

```
                        405                 410                 415
Trp Gln Gln Gly Asn Thr Phe Thr Cys Ser Val Leu His Glu Gly Leu
            420                 425                 430
His Asn His His Thr Glu Lys Ser Leu Ser His Ser Pro Gly Lys
            435                 440                 445

<210> SEQ ID NO 4
<211> LENGTH: 212
<212> TYPE: PRT
<213> ORGANISM: Rattus norvegicus

<400> SEQUENCE: 4

Tyr Glu Leu Ile Gln Pro Pro Ser Ala Ser Val Thr Leu Gly Asn Thr
1               5                   10                  15
Val Ser Ile Thr Cys Ser Gly Asp Glu Leu Pro Lys Arg Tyr Ala Tyr
                20                  25                  30
Trp Tyr Gln Gln Lys Pro Asp Lys Ser Ile Val Arg Val Ile Tyr Lys
            35                  40                  45
Asp Ser Glu Arg Pro Ser Gly Ile Ser Asp Arg Phe Ser Gly Ser Ser
        50                  55                  60
Ser Gly Thr Thr Ala Thr Leu Thr Ile Arg Asp Thr Gln Ala Glu Asp
65                  70                  75                  80
Glu Ala Asp Tyr Tyr Cys His Ser Thr Tyr Ser Asp Asp Lys Leu Pro
                85                  90                  95
Val Phe Gly Gly Gly Thr Lys Leu Thr Val Leu Gly Gln Pro Lys Ser
            100                 105                 110
Thr Pro Thr Leu Thr Val Phe Pro Pro Ser Thr Glu Glu Leu Gln Gly
        115                 120                 125
Asn Lys Ala Thr Leu Val Cys Leu Ile Ser Asp Phe Tyr Pro Ser Asp
130                 135                 140
Val Glu Val Ala Trp Lys Ala Asn Gly Ala Pro Ile Ser Gln Gly Val
145                 150                 155                 160
Asp Thr Ala Asn Pro Thr Lys Gln Gly Asn Lys Tyr Ile Ala Ser Ser
                165                 170                 175
Phe Leu Arg Leu Thr Ala Glu Gln Trp Arg Ser Arg Asn Ser Phe Thr
            180                 185                 190
Cys Gln Val Thr His Glu Gly Asn Thr Val Glu Lys Ser Leu Ser Pro
        195                 200                 205
Ala Glu Cys Ser
        210

<210> SEQ ID NO 5
<211> LENGTH: 125
<212> TYPE: PRT
<213> ORGANISM: Rattus norvegicus

<400> SEQUENCE: 5

Ala Val Gln Leu Val Glu Ser Gly Gly Gly Leu Val Gln Pro Lys Glu
1               5                   10                  15
Ser Leu Lys Ile Ser Cys Ala Ala Ser Gly Phe Thr Phe Ser Asn Ala
                20                  25                  30
Ala Met Tyr Trp Val Arg Gln Ala Pro Gly Lys Gly Leu Glu Trp Val
            35                  40                  45
Ala Arg Ile Arg Thr Lys Pro Asn Asn Tyr Ala Thr Tyr Tyr Ala Asp
        50                  55                  60
Ser Val Lys Gly Arg Phe Thr Ile Ser Arg Asp Asp Ser Lys Ser Met
```

```
            65                  70                  75                  80
Val Tyr Leu Gln Met Asp Asn Leu Lys Thr Glu Asp Thr Ala Met Tyr
                    85                  90                  95
Tyr Cys Thr Ala Pro Arg Arg Thr Glu Gly Ile Val Ser Ser Gly Val
                    100                 105                 110
Asp Tyr Trp Gly Gln Gly Val Met Val Thr Val Ser Ser
                    115                 120                 125

<210> SEQ ID NO 6
<211> LENGTH: 107
<212> TYPE: PRT
<213> ORGANISM: Rattus norvegicus

<400> SEQUENCE: 6

Tyr Glu Leu Ile Gln Pro Pro Ser Ala Ser Val Thr Leu Gly Asn Thr
1               5                   10                  15
Val Ser Ile Thr Cys Ser Gly Asp Glu Leu Pro Lys Arg Tyr Ala Tyr
                20                  25                  30
Trp Tyr Gln Gln Lys Pro Asp Lys Ser Ile Val Arg Val Ile Tyr Lys
                35                  40                  45
Asp Ser Glu Arg Pro Ser Gly Ile Ser Asp Arg Phe Ser Gly Ser Ser
            50                  55                  60
Ser Gly Thr Thr Ala Thr Leu Thr Ile Arg Asp Thr Gln Ala Glu Asp
65                  70                  75                  80
Glu Ala Asp Tyr Tyr Cys His Ser Thr Tyr Ser Asp Asp Lys Leu Pro
                85                  90                  95
Val Phe Gly Gly Gly Thr Lys Leu Thr Val Leu
                100                 105

<210> SEQ ID NO 7
<211> LENGTH: 10
<212> TYPE: PRT
<213> ORGANISM: Rattus norvegicus

<400> SEQUENCE: 7

Gly Phe Thr Phe Ser Asn Ala Ala Met Tyr
1               5                   10

<210> SEQ ID NO 8
<211> LENGTH: 19
<212> TYPE: PRT
<213> ORGANISM: Rattus norvegicus

<400> SEQUENCE: 8

Arg Ile Arg Thr Lys Pro Asn Asn Tyr Ala Thr Tyr Tyr Ala Asp Ser
1               5                   10                  15
Val Lys Gly

<210> SEQ ID NO 9
<211> LENGTH: 14
<212> TYPE: PRT
<213> ORGANISM: Rattus norvegicus

<400> SEQUENCE: 9

Pro Arg Arg Thr Glu Gly Ile Val Ser Ser Gly Val Asp Tyr
1               5                   10

<210> SEQ ID NO 10
<211> LENGTH: 11
<212> TYPE: PRT
```

<210> SEQ ID NO 11
<211> LENGTH: 7
<212> TYPE: PRT
<213> ORGANISM: Rattus norvegicus

<400> SEQUENCE: 10

Ser Gly Asp Glu Leu Pro Lys Arg Tyr Ala Tyr
1               5                   10

<210> SEQ ID NO 11
<211> LENGTH: 7
<212> TYPE: PRT
<213> ORGANISM: Rattus norvegicus

<400> SEQUENCE: 11

Lys Asp Ser Glu Arg Pro Ser
1               5

<210> SEQ ID NO 12
<211> LENGTH: 11
<212> TYPE: PRT
<213> ORGANISM: Rattus norvegicus

<400> SEQUENCE: 12

His Ser Thr Tyr Ser Asp Asp Lys Leu Pro Val
1               5                   10

<210> SEQ ID NO 13
<211> LENGTH: 455
<212> TYPE: PRT
<213> ORGANISM: Artificial Sequence
<220> FEATURE:
<223> OTHER INFORMATION: Amino acid sequence of a H-chain of a chimera
      antibody in which constant regions of a rat antibody are replaced
      with human-derived amino acid sequences

<400> SEQUENCE: 13

Ala Val Gln Leu Val Glu Ser Gly Gly Gly Leu Val Gln Pro Lys Glu
1               5                   10                  15

Ser Leu Lys Ile Ser Cys Ala Ala Ser Gly Phe Thr Phe Ser Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Tyr Tyr Ala Asp
    50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Thr Glu Asp Thr Ala Met Tyr
                85                  90                  95

Tyr Cys Thr Ala Pro Arg Arg Thr Glu Gly Ile Val Ser Ser Gly Val
            100                 105                 110

Asp Tyr Trp Gly Gln Gly Val Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

```
Asn Val Asn His Lys Pro Ser Asn Thr Lys Val Asp Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
        450                 455

<210> SEQ ID NO 14
<211> LENGTH: 213
<212> TYPE: PRT
<213> ORGANISM: Artificial Sequence
<220> FEATURE:
<223> OTHER INFORMATION: Amino acid sequence of a L-chain of a chimera
      antibody in which constant regions of a rat antibody are replaced
      with human-derived amino acid sequences

<400> SEQUENCE: 14

Tyr Glu Leu Ile Gln Pro Pro Ser Ala Ser Val Thr Leu Gly Asn Thr
1               5                   10                  15

Val Ser Ile Thr Cys Ser Gly Asp Glu Leu Pro Lys Arg Tyr Ala Tyr
                20                  25                  30

Trp Tyr Gln Gln Lys Pro Asp Lys Ser Ile Val Arg Val Ile Tyr Lys
                35                  40                  45

Asp Ser Glu Arg Pro Ser Gly Ile Ser Asp Arg Phe Ser Gly Ser Ser
        50                  55                  60

Ser Gly Thr Thr Ala Thr Leu Thr Ile Arg Asp Thr Gln Ala Glu Asp
65                  70                  75                  80

Glu Ala Asp Tyr Tyr Cys His Ser Thr Tyr Ser Asp Asp Lys Leu Pro
                85                  90                  95
```

```
Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 15
<211> LENGTH: 94
<212> TYPE: PRT
<213> ORGANISM: Homo sapiens

<400> SEQUENCE: 15

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Glu Arg Phe Ser Gly Ser
    50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn
            85                  90

<210> SEQ ID NO 16
<211> LENGTH: 96
<212> TYPE: PRT
<213> ORGANISM: Homo sapiens

<400> SEQUENCE: 16

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
            85                  90                  95

<210> SEQ ID NO 17
<211> LENGTH: 96
```

```
<212> TYPE: PRT
<213> ORGANISM: Homo sapiens

<400> SEQUENCE: 17

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

<210> SEQ ID NO 18
<211> LENGTH: 95
<212> TYPE: PRT
<213> ORGANISM: Homo sapiens

<400> SEQUENCE: 18

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn Leu
                85                  90                  95

<210> SEQ ID NO 19
<211> LENGTH: 95
<212> TYPE: PRT
<213> ORGANISM: Homo sapiens

<400> SEQUENCE: 19

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95

<210> SEQ ID NO 20
<211> LENGTH: 105
<212> TYPE: PRT
```

<213> ORGANISM: Homo sapiens

<400> SEQUENCE: 20

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Arg Ser Pro Val Leu Leu Ile Tyr
        35                  40                  45

Gln Asp Thr Lys Arg Pro Ser Gly Ile Pro Glu Arg Phe Ser Gly Ser
    50                  55                  60

Asn Ser Gly Gly Thr Ala Thr Leu Thr Ile Ser Gly Thr Gln Thr Met
65                  70                  75                  80

Asp Glu Ala Asp Tyr Tyr Cys Gln Ala Trp Asp Arg Ser Val Val Phe
                85                  90                  95

Gly Gly Gly Thr Lys Leu Thr Val Leu
            100                 105

<210> SEQ ID NO 21
<211> LENGTH: 22
<212> TYPE: PRT
<213> ORGANISM: Artificial Sequence
<220> FEATURE:
<223> OTHER INFORMATION: Human framework region 1 of a human-derived L
      chain variable region sequence hLV3_cons

<400> SEQUENCE: 21

Ser Tyr Glu Leu Thr Gln Pro Pro Ser Val Ser Val Ser Pro Gly Gln
1               5                   10                  15

Thr Ala Arg Ile Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: Human framework region 2 of a human-derived L
      chain variable region sequence hLV3_cons

<400> SEQUENCE: 22

Trp Tyr Gln Gln Lys Pro Gly Gln Ala Pro Val Leu Val Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Human framework region 3 of a human-derived L
      chain variable region sequence hLV3_cons

<400> SEQUENCE: 23

Gly Ile Pro Glu Arg Phe Ser Gly Ser Ser Ser Gly Asn Thr Ala Thr
1               5                   10                  15

Leu Thr Ile Ser Gly Ala Gln Ala Glu Asp Glu Ala Asp Tyr Tyr Cys
            20                  25                  30

<210> SEQ ID NO 24
<211> LENGTH: 12
<212> TYPE: PRT
<213> ORGANISM: Artificial Sequence
<220> FEATURE:

<223> OTHER INFORMATION: Human framework region 4 of a human-derived L
      chain variable region sequence hLV3_cons

<400> SEQUENCE: 24

Val Val Phe Gly Gly Gly Thr Lys Leu Thr Val Leu
1               5                   10

<210> SEQ ID NO 25
<211> LENGTH: 21
<212> TYPE: PRT
<213> ORGANISM: Artificial Sequence
<220> FEATURE:
<223> OTHER INFORMATION: Human amino acid sequence for a L chain
      framework region 1

<400> SEQUENCE: 25

Tyr Glu Leu Thr Gln Pro Pro Ser Val Ser Val Ser Pro Gly Gln Thr
1               5                   10                  15

Ala Ser Ile Thr Cys
            20

<210> SEQ ID NO 26
<211> LENGTH: 15
<212> TYPE: PRT
<213> ORGANISM: Artificial Sequence
<220> FEATURE:
<223> OTHER INFORMATION: Human amino acid sequence for a L chain
      framework region 2

<400> SEQUENCE: 26

Trp Tyr Gln Gln Lys Pro Gly Gln Ser Pro Val Leu Val Ile Tyr
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: Human amino acid sequence for a L chain
      framework region 3

<400> SEQUENCE: 27

Gly Ile Pro Glu Arg Phe Ser Gly Ser Ser Ser Gly Thr Thr Ala Thr
1               5                   10                  15

Leu Thr Ile Ser Gly Thr Gln Ala Glu Asp Glu Ala Asp Tyr Tyr Cys
            20                  25                  30

<210> SEQ ID NO 28
<211> LENGTH: 10
<212> TYPE: PRT
<213> ORGANISM: Artificial Sequence
<220> FEATURE:
<223> OTHER INFORMATION: Human amino acid sequence for a L chain
      framework region 4

<400> SEQUENCE: 28

Phe Gly Gly Gly Thr Lys Leu Thr Val Leu
1               5                   10

<210> SEQ ID NO 29
<211> LENGTH: 100
<212> TYPE: PRT
<213> ORGANISM: Homo sapiens

<400> SEQUENCE: 29

Glu Val Gln Leu Val Glu Ser Gly Gly Gly Leu Val Gln Pro Gly Gly

```
1               5                  10                 15
Ser Leu Lys Leu Ser Cys Ala Ala Ser Gly Phe Thr Phe Ser Gly Ser
            20                 25                 30

Ala Met His Trp Val Arg Gln Ala Ser Gly Lys Gly Leu Glu Trp Val
            35                 40                 45

Gly Arg Ile Arg Ser Lys Ala Asn Ser Tyr Ala Thr Ala Tyr Ala Ala
            50                 55                 60

Ser Val Lys Gly Arg Phe Thr Ile Ser Arg Asp Asp Ser Lys Asn Thr
65                  70                 75                 80

Ala Tyr Leu Gln Met Asn Ser Leu Lys Thr Glu Asp Thr Ala Val Tyr
                    85                 90                 95

Tyr Cys Thr Arg
            100
```

```
<210> SEQ ID NO 30
<211> LENGTH: 115
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                  10                 15

Ser Leu Lys Leu Ser Cys Ala Ala Ser Gly Phe Thr Phe Ser Gly Ser
            20                 25                 30

Ala Met His Trp Val Arg Gln Ala Ser Gly Lys Gly Leu Glu Trp Val
            35                 40                 45

Gly Arg Ile Arg Ser Lys Ala Asn Ser Tyr Ala Thr Ala Tyr Ala Ala
            50                 55                 60

Ser Val Lys Gly Arg Phe Thr Ile Ser Arg Asp Asp Ser Lys Asn Thr
65                  70                 75                 80

Ala Tyr Leu Gln Met Asn Ser Leu Lys Thr Glu Asp Thr Ala Val Tyr
                    85                 90                 95

Tyr Cys Thr Ser Ile Ala Gln Glu Gly Val Arg Trp Gly Leu Gly Thr
            100                105                110

Leu Val Thr
        115
```

```
<210> SEQ ID NO 31
<211> LENGTH: 121
<212> TYPE: PRT
<213> ORGANISM: Homo sapiens

<400> SEQUENCE: 31

Glu Val Gln Leu Val Glu Ser Gly Gly Gly Leu Val Gln Pro Gly Gly
1               5                  10                 15

Ser Leu Lys Leu Ser Cys Ala Ala Ser Gly Phe Thr Phe Ser Gly Ser
            20                 25                 30

Ala Met His Trp Val Arg Gln Ala Ser Gly Lys Gly Leu Glu Trp Val
            35                 40                 45

Gly Arg Ile Arg Ser Lys Ala Asn Ser Tyr Ala Thr Ala Tyr Ala Ala
            50                 55                 60

Ser Val Lys Gly Arg Phe Thr Ile Ser Arg Asp Asp Ser Lys Asn Thr
65                  70                 75                 80

Ala Tyr Leu Gln Met Asn Ser Leu Lys Thr Glu Asp Thr Ala Val Tyr
                    85                 90                 95

Tyr Cys Thr Thr Cys Gly Gly Asp Cys Ser His Phe Gly Tyr Trp Gly
```

```
                100                 105                 110
Gln Gly Thr Leu Val Thr Val Ser Ser
            115                 120

<210> SEQ ID NO 32
<211> LENGTH: 100
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 33
<211> LENGTH: 114
<212> TYPE: PRT
<213> ORGANISM: Homo sapiens

<400> SEQUENCE: 33

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asp Ser Leu Lys Thr Glu Asp Thr Ala Val Tyr
                85                  90                  95

Tyr Cys Thr Thr Tyr Glu Gly Trp Gly Gln Gly Thr Leu Val Thr Val
            100                 105                 110

Ser Ser

<210> SEQ ID NO 34
<211> LENGTH: 100
<212> TYPE: PRT
<213> ORGANISM: Homo sapiens

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30
```

Tyr Met Ser Trp Val Arg Gln Ala Gln Gly Lys Gly Leu Glu Leu Val
             35                  40                  45

Gly Leu Ile Arg Asn Lys Ala Asn Ser Tyr Thr Thr Glu Tyr Ala Ala
 50                  55                  60

Ser Val Lys Gly Arg Leu Thr Ile Ser Arg Glu Asp Ser Lys Asn Thr
 65                  70                  75                  80

Leu Tyr Leu Gln Met Ser Ser Leu Lys Thr Glu Asp Leu Ala Val Tyr
                 85                  90                  95

Tyr Cys Ala Arg
            100

<210> SEQ ID NO 35
<211> LENGTH: 25
<212> TYPE: PRT
<213> ORGANISM: Artificial Sequence
<220> FEATURE:
<223> OTHER INFORMATION: Human amino acid sequence of a H chain
      framework region 1

<400> SEQUENCE: 35

Glu Val Gln Leu Val Glu Ser Gly Gly Gly Leu Val Gln Pro Gly Gly
 1               5                  10                  15

Ser Leu Lys Leu Ser Cys Ala Ala Ser
             20                  25

<210> SEQ ID NO 36
<211> LENGTH: 14
<212> TYPE: PRT
<213> ORGANISM: Artificial Sequence
<220> FEATURE:
<223> OTHER INFORMATION: Human amino acid sequence of a H chain
      framework region 2

<400> SEQUENCE: 36

Trp Val Arg Gln Ala Ser Gly Lys Gly Leu Glu Trp Val Gly
 1               5                  10

<210> SEQ ID NO 37
<211> LENGTH: 32
<212> TYPE: PRT
<213> ORGANISM: Artificial Sequence
<220> FEATURE:
<223> OTHER INFORMATION: Human amino acid sequence of a H chain
      framework region 3

<400> SEQUENCE: 37

Arg Phe Thr Ile Ser Arg Asp Asp Ser Lys Asn Thr Ala Tyr Leu Gln
 1               5                  10                  15

Met Asn Ser Leu Lys Thr Glu Asp Thr Ala Val Tyr Tyr Cys Thr Arg
             20                  25                  30

<210> SEQ ID NO 38
<211> LENGTH: 11
<212> TYPE: PRT
<213> ORGANISM: Artificial Sequence
<220> FEATURE:
<223> OTHER INFORMATION: Human amino acid sequence of a H chain
      framework region 4

<400> SEQUENCE: 38

Trp Gly Gln Gly Thr Leu Val Thr Val Ser Ser
 1               5                  10

<210> SEQ ID NO 39

<211> LENGTH: 455
<212> TYPE: PRT
<213> ORGANISM: Artificial Sequence
<220> FEATURE:
<223> OTHER INFORMATION: Full-length H-chain amino acid sequence of a humanized anti-HMGB1 antibody EV007156

<400> SEQUENCE: 39

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Ala
            20                  25                  30

Ala Met Tyr Trp Val Arg Gln Ala Ser Gly Lys Gly Leu Glu Trp Val
        35                  40                  45

Ala Arg Ile Arg Thr Lys Pro Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ala Pro Arg Arg Thr Glu Gly Ile Val Ser Ser Gly Val
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
```

```
               370                 375                 380
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
450                 455

<210> SEQ ID NO 40
<211> LENGTH: 213
<212> TYPE: PRT
<213> ORGANISM: Artificial Sequence
<220> FEATURE:
<223> OTHER INFORMATION: Full-length L-chain amino acid sequence of
      a humanized anti-HMGB1 antibody EV007156

<400> SEQUENCE: 40

Tyr Glu Leu Thr Gln Pro Pro Ser Val Ser Val Ser Pro Gly Gln Thr
1               5                   10                  15

Ala Ser Ile Thr Cys Ser Gly Asp Glu Leu Pro Lys Arg Tyr Ala Tyr
                20                  25                  30

Trp Tyr Gln Gln Lys Pro Gly Gln Ser Ile Val Arg Val Ile Tyr Lys
                35                  40                  45

Asp Ser Glu Arg Pro Ser Gly Ile Pro Glu Arg Phe Ser Gly Ser Ser
            50                  55                  60

Ser Gly Thr Thr Ala Thr Leu Thr Ile Ser Gly Thr Gln Ala Glu Asp
65              70                  75                  80

Glu Ala Asp Tyr Tyr Cys His Ser Thr Tyr Ser Asp Asp Lys Leu Pro
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Thr Leu Val Cys Leu Ile Ser Asp Phe Tyr Pro Gly Ala
                130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
                195                 200                 205

Pro Thr Glu Cys Ser
        210

<210> SEQ ID NO 41
<211> LENGTH: 125
<212> TYPE: PRT
<213> ORGANISM: Artificial Sequence
<220> FEATURE:
<223> OTHER INFORMATION: Variable region amino acid sequence of a
      full-length H-chain amino acid sequence of a humanized anti-HMGB1
      antibody EV007156
```

<400> SEQUENCE: 41

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Ala
            20                  25                  30

Ala Met Tyr Trp Val Arg Gln Ala Ser Gly Lys Gly Leu Glu Trp Val
        35                  40                  45

Ala Arg Ile Arg Thr Lys Pro Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ala Pro Arg Arg Thr Glu Gly Ile Val Ser Ser Gly Val
            100                 105                 110

Asp Tyr Trp Gly Gln Gly Thr Leu Val Thr Val Ser Ser
            115                 120                 125

<210> SEQ ID NO 42
<211> LENGTH: 107
<212> TYPE: PRT
<213> ORGANISM: Artificial Sequence
<220> FEATURE:
<223> OTHER INFORMATION: Variable region amino acid sequence of a
      full-length L-chain amino acid sequence of a humanized anti-HMGB1
      antibody EV007156

<400> SEQUENCE: 42

Tyr Glu Leu Thr Gln Pro Pro Ser Val Ser Val Ser Pro Gly Gln Thr
1               5                   10                  15

Ala Ser Ile Thr Cys Ser Gly Asp Glu Leu Pro Lys Arg Tyr Ala Tyr
            20                  25                  30

Trp Tyr Gln Gln Lys Pro Gly Gln Ser Ile Val Arg Val Ile Tyr Lys
        35                  40                  45

Asp Ser Glu Arg Pro Ser Gly Ile Pro Glu Arg Phe Ser Gly Ser Ser
    50                  55                  60

Ser Gly Thr Thr Ala Thr Leu Thr Ile Ser Gly Thr Gln Ala Glu Asp
65                  70                  75                  80

Glu Ala Asp Tyr Tyr Cys His Ser Thr Tyr Ser Asp Asp Lys Leu Pro
                85                  90                  95

Val Phe Gly Gly Gly Thr Lys Leu Thr Val Leu
            100                 105

<210> SEQ ID NO 43
<211> LENGTH: 25
<212> TYPE: PRT
<213> ORGANISM: Artificial Sequence
<220> FEATURE:
<223> OTHER INFORMATION: Amino acid sequence of a H chain variable
      region FR (framework region) 1 of EV007156

<400> SEQUENCE: 43

Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 44

```
<211> LENGTH: 14
<212> TYPE: PRT
<213> ORGANISM: Artificial Sequence
<220> FEATURE:
<223> OTHER INFORMATION: Amino acid sequence of a H chain variable
      region FR2 of EV007156

<400> SEQUENCE: 44

Trp Val Arg Gln Ala Ser Gly Lys Gly Leu Glu Trp Val Ala
1               5                   10

<210> SEQ ID NO 45
<211> LENGTH: 32
<212> TYPE: PRT
<213> ORGANISM: Artificial Sequence
<220> FEATURE:
<223> OTHER INFORMATION: Amino acid sequence of a H chain variable
      region FR3 of EV007156

<400> SEQUENCE: 45

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Thr Ala
                20                  25                  30

<210> SEQ ID NO 46
<211> LENGTH: 11
<212> TYPE: PRT
<213> ORGANISM: Artificial Sequence
<220> FEATURE:
<223> OTHER INFORMATION: Amino acid sequence of a H chain variable
      region FR4 of EV007156

<400> SEQUENCE: 46

Trp Gly Gln Gly Thr Leu Val Thr Val Ser Ser
1               5                   10

<210> SEQ ID NO 47
<211> LENGTH: 21
<212> TYPE: PRT
<213> ORGANISM: Artificial Sequence
<220> FEATURE:
<223> OTHER INFORMATION: Amino acid sequence of a L chain variable
      region FR1 of EV007156

<400> SEQUENCE: 47

Tyr Glu Leu Thr Gln Pro Pro Ser Val Ser Val Ser Pro Gly Gln Thr
1               5                   10                  15

Ala Ser Ile Thr Cys
            20

<210> SEQ ID NO 48
<211> LENGTH: 15
<212> TYPE: PRT
<213> ORGANISM: Artificial Sequence
<220> FEATURE:
<223> OTHER INFORMATION: Amino acid sequence of a L chain variable
      region FR2 of EV007156

<400> SEQUENCE: 48

Trp Tyr Gln Gln Lys Pro Gly Gln Ser Ile Val Arg Val Ile Tyr
1               5                   10                  15

<210> SEQ ID NO 49
<211> LENGTH: 32
<212> TYPE: PRT
<213> ORGANISM: Artificial Sequence
```

```
<220> FEATURE:
<223> OTHER INFORMATION: Amino acid sequence of a L chain variable
      region FR3 of EV007156

<400> SEQUENCE: 49

Gly Ile Pro Glu Arg Phe Ser Gly Ser Ser Ser Gly Thr Thr Ala Thr
1               5                   10                  15

Leu Thr Ile Ser Gly Thr Gln Ala Glu Asp Glu Ala Asp Tyr Tyr Cys
            20                  25                  30

<210> SEQ ID NO 50
<211> LENGTH: 10
<212> TYPE: PRT
<213> ORGANISM: Artificial Sequence
<220> FEATURE:
<223> OTHER INFORMATION: Amino acid sequence of a L chain variable
      region FR4 of EV007156

<400> SEQUENCE: 50

Phe Gly Gly Gly Thr Lys Leu Thr Val Leu
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthesized amino acid sequence constituting
      the C-terminal end of HMGB1

<400> SEQUENCE: 51

Glu Glu Glu Glu Asp Glu Glu Asp Glu Glu Asp Glu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthesized amino acid sequence constituting
      the C-terminal end of HMGB1

<400> SEQUENCE: 52

Glu Asp Glu Glu Asp Glu Glu Asp Glu Glu Glu Glu
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthesized amino acid sequence constituting
      the C-terminal end of HMGB1

<400> SEQUENCE: 53

Glu Asp Glu Glu Asp Glu Glu Glu Glu Glu Asp Glu
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthesized amino acid sequence constituting
      the C-terminal end of HMGB1

<400> SEQUENCE: 54
```

<210> SEQ ID NO 55
<211> LENGTH: 12
<212> TYPE: PRT
<213> ORGANISM: Artificial Sequence
<220> FEATURE:
<223> OTHER INFORMATION: Synthesized amino acid sequence constituting the C-terminal end of HMGB1

<400> SEQUENCE: 55

Asp Glu Glu Glu Glu Glu Asp Glu Glu Asp Glu Asp
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthesized amino acid sequence constituting the C-terminal end of HMGB1

<400> SEQUENCE: 56

Glu Glu Glu Glu Asp Glu Glu Asp Glu Asp Glu Glu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthesized amino acid sequence constituting the C-terminal end of HMGB1

<400> SEQUENCE: 57

Glu Glu Asp Glu Glu Asp Glu Asp Glu Glu Glu Asp
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthesized amino acid sequence constituting the C-terminal end of HMGB1

<400> SEQUENCE: 58

Asp Glu Glu Asp Glu Asp Glu Glu Glu Asp Asp Asp
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthesized amino acid sequence constituting the C-terminal end of HMGB1

<400> SEQUENCE: 59

Glu Asp Glu Asp Glu Glu Glu Asp Asp Asp Asp Glu
1               5                   10

<210> SEQ ID NO 60
<211> LENGTH: 8
<212> TYPE: PRT
<213> ORGANISM: Artificial Sequence
<220> FEATURE:

```
<223> OTHER INFORMATION: Synthesized amino acid sequence constituting
      the C-terminal end of HMGB1

<400> SEQUENCE: 60

Glu Glu Glu Asp Asp Asp Asp Glu
1               5
```

HUMANIZED ANTI-HMGB1 ANTIBODY OR ANTIGEN-BINDING FRAGMENT THEREOF

CROSS-REFERENCE TO RELATED APPLICATIONS

This application is a U.S. national stage entry under 35 U.S.C. §371 of PCT International Patent Application No. PCT/JP2013/082860, filed Dec. 6, 2013, which claims the benefit of JP Patent Application No. 2013-013602, filed Jan. 28, 2013, the contents of which are incorporated herein by reference in their entirety.

TECHNICAL FIELD

The present invention relates to a humanized anti-HMGB1 antibody which specifically binds to HMGB1 protein and is effective for treatment and/or prevention of HMGB1-related diseases, as well as an antigen-binding fragment thereof.

BACKGROUND ART

HMGB1 (high mobility group box 1) is a protein which has recently been rediscovered as an early or late inflammatory mediator distinct from the previously identified inflammatory cytokines (e.g., tumor necrosis factor and various interleukins) in diseases such as cerebral infarction, cerebral vasospasm, brain trauma, atherosclerosis, traumatic brain damage, sepsis, neuropathic pain and various types of arthritis, for which no therapeutic method has yet been sufficiently established; and HMGB1 is now receiving great attention because it can serve as a target of therapeutic and/or prophylactic methods for these diseases (Non-patent Document 1).

HMGB1 was discovered about 40 years ago as a protein showing high mobility during electrophoresis, which is among the non-histone proteins ubiquitously present in the cell nuclei of eukaryotic organisms and bound to chromatin. At first, this protein was referred to as HMG1 (high mobility group 1) as a member belonging to the high mobility group (HMG) protein family and was considered to play important roles in chromatin structure maintenance, transcriptional activity regulation and DNA repair, etc. Thereafter, it was rediscovered as a membrane binding protein (amphoterin) and further rediscovered again as an inflammatory mediator involved in various inflammatory diseases. In 2001, HMG1 was renamed HMGB1 as a result of reconsidering the nomenclature of the high mobility protein family.

HMGB1 protein is a 25 kDa protein composed of 215 amino acids rich in lysine residues and has an amino acid sequence which is very highly conserved among mammals. Its structure is composed of three domains, i.e., two DNA-binding domains called A-box (or box-A) and B-box (or box-B), and a carboxyl-terminal domain consisting only of aspartic acid and glutamic acid residues (also referred to as the C-terminal domain or acidic tail). The A-box and B-box are each composed of about 80 highly conserved amino acid residues, and are strongly positively charged. The B-box has a TLR4 (toll-like receptor 4)-binding domain and a RAGE (receptor for advanced glycation end products)-binding domain. Upon binding to TLR4, HMGB1 induces the secretion of inflammatory cytokines from macrophages/monocytes. Upon binding to RAGE, HMGB1 induces the growth, differentiation and migration of endothelial cells and other somatic cells (including tumor cells) and the expression of their cell surface proteins. The third domain, i.e., the carboxyl-terminal end has a structure consisting of a 30 amino acid sequence composed only of aspartic acid and glutamic acid residues and is excessively negatively charged. The amino acid sequence of this C-terminal segment is also known to be highly conserved among mammals, only with a few differences.

The HMGB1 protein was considered at first to have the functions of chromatin structure maintenance, transcriptional activity regulation, DNA repair and so on. However, particularly after 1999 when the HMGB1 protein was rediscovered as a late inflammatory mediator in sepsis by the research group of Tracey et al., discoveries have been made one after another, showing that the HMGB1 protein plays important roles in inflammatory cytokine cascades in various diseases. HMGB1 is not only localized in the nuclei of cells, but also migrates from the nuclei to the cytoplasm upon activation of macrophages and/or various cells of the immune system and is thereby secreted into the extracellular environment (active secretion). Alternatively, it has been elucidated that HMGB1 localized in the nuclei is rapidly released upon ischemia- or damage-induced cell necrosis or apoptosis (passive release). In recent years, HMGB1 or heat shock protein (HSP) or the like has been regarded as one of the endogenous damage-associated molecular patterns (DAMPs), which are released from damaged cells resulting from non-microbial causes (e.g., ischemia, trauma and the like). On the other hand, bacterial lipopolysaccharides (LPSs) and the like are referred to as pathogen-associated molecular patterns (PAMPs), which include various products of microbial origin. Receptors that recognize and respond to the latter patterns both on the cell surface and in the cytoplasm are referred to as pattern recognition receptors (PRRs), and their representative families include Toll-like receptors (TLRs). However, some members of the TLR family, particularly TLR2, TLR4 and TLR9 recognize and activate the above DAMPs. In particular, HMGB1 is known to activate TLR4 signaling and other events to induce inflammatory response, thereby resulting in enhanced TNFα secretion, etc. Moreover, as to RAGE, which is one of the HMGB1 receptors, it has been shown that RAGE-mediated transmission of inflammatory information plays an important role in amplification of this HMGB1-induced inflammatory response in diseases such as ischemia-induced brain disorder (Non-patent Document 2) and sepsis associated with bacterial infection (Non-patent Document 3), as a result of studies using RAGE knockout animals and/or studies using inhibitory peptides or specific antibodies against binding between RAGE and HMGB1. Namely, HMGB1 released into the extracellular environment acts as a strong inflammatory mediator via TLR4 or RAGE, etc., to further stimulate previously known inflammatory immune responses, so that HMGB1 may also be responsible for causing various serious diseases.

These diseases in which HMGB1 is involved (HMGB1-related diseases) are divided into two major groups, i.e., a group of diseases (e.g., septic shock) showing the extracellular secretion of HMGB1 resulting from microbial infection-induced immune responses, and a group of diseases (e.g., cerebral infarction) showing the extracellular release of HMGB1 caused by cell injury due to non-microbial causes. In the former group, TLR4 activation is induced, for example, by the action of bacterial components (e.g., bacterial lipopolysaccharides (LPSs)) produced upon infection. In response to this activation, monocytes, macrophages and other cells cause active secretion of HMGB1, which in turn acts as a late inflammatory mediator. HMGB1-related diseases in this context include sepsis, arthritis, atherosclerosis, various infections, and various immune diseases, etc. The latter group corresponds to cases where upon ischemia- or trauma-induced cell necrosis, HMGB1 having been localized in the nuclei is rapidly released into the extracellular environment within several hours (passive release) and thereby acts as an early inflammatory mediator to induce production of various inflammatory cytokines. Relevant diseases include cerebral infarction, traumatic brain injury, diseases due to ischemia during organ transplantation, myocardial infarction and so on.

In recent years, as to therapeutic or prophylactic methods for HMGB1-related diseases, reports have been made on studies searching for methods using an antibody against HMGB1 (Patent Documents 1, 2, 4 and 5), methods using a partial fragment of HMGB1 protein as an antagonist (Patent Documents 2 and 3), methods using an inhibitory compound against HMGB1 secretion (Non-patent Document 4) and so on. In particular, therapeutic methods using an antibody against HMGB1 in an animal model have been reported for the possibility of their application to sepsis (Patent Documents 1, 4 and 5), acute lung injury (Non-patent Document 5), connective tissue injury due to heat burn (Patent Document 2), arthritis (Patent Documents 4 and 5 and Non-patent Document 6), cerebral ischemia (Non-patent Document 7), amyloidosis (Patent Document 6), hepatopathy during intraportal islet transplantation (Non-patent Document 8) and neuropathic pain (Non-patent Document 9), etc. However, all of these studies have just been started as studies of therapeutic and prophylactic agents.

Under these circumstances, we have shown that rat-derived anti-HMGB1 monoclonal antibody is effective in animal models of cerebral infarction (Patent Document 8, Non-patent Documents 10 and 11), cerebral vasospasm (Patent Document 9), atherosclerosis (Patent Document 10 and Non-patent Document 12), traumatic brain damage (Patent Document 11 and Non-patent Document 13) and neuropathic pain (Non-patent Document 9). However, such a rat-derived antibody has a problem of immunogenicity and is difficult to use in humans.

CITATION LIST

Patent Documents

Patent Document 1: WO2000/047104
Patent Document 2: WO2002/074337
Patent Document 3: WO2004/046345
Patent Document 4: WO2005/026209
Patent Document 5: WO2007/001422
Patent Document 6: WO2008/075788
Patent Document 7: WO2012/136250
Patent Document 8: WO2007/049468
Patent Document 9: WO2007/135992
Patent Document 10: WO2011/037227
Patent Document 11: WO2012/074043

Non-Patent Documents

Non-patent Document 1: Annu. Rev. Immunol., 2011 (vol. 29) p. 139
Non-patent Document 2: J. Neuros., 2008 (vol. 28) p. 12023
Non-patent Document 3: Crit. Care, 2007 (vol. 11) p. R122
Non-patent Document 4: Biochem Pharmacol. 2012 p. 1492
Non-patent Document 5: J. Immunol., 2000 (165) p. 2950
Non-patent Document 6: Mol. Med., 2011 (vol. 17) p. 1039
Non-patent Document 7: J. Neurosci., 2006 (vol. 26) p. 6413
Non-patent Document 8: Am. J. Transplant., 2010 (vol. 10) p. 1588
Non-patent Document 9: PLoS One. 2013 (vol. 8) e73640
Non-patent Document 10: FASEB J., 2007 (vol. 21) p. 3904
Non-patent Document 11: Stroke., 2011 (vol. 42) p. 1420
Non-patent Document 12: Arterioscler Thromb Vasc Biol., 2011 (vol. 31) p. 313
Non-patent Document 13: Ann Neurol., 2012 (72) p. 373

SUMMARY OF THE INVENTION

Problem to be Solved by the Invention

Anti-HMGB1 antibody is now receiving great attention as an antagonist of inflammatory mediators which are fundamentally responsible for lethal inflammatory responses observed in, e.g., ischemia/reperfusion injury, traumatic brain damage, neuropathic pain and sepsis, for which no therapeutic method has yet been sufficiently established. This is because anti-HMGB1 antibody has the potential to serve as an agent which solves the problems lying in therapeutic and/or prophylactic methods for these diseases. Under these circumstances, we have shown that rat-derived anti-HMGB1 monoclonal antibody (#10-22) is effective in animal models of cerebral infarction (Patent Document 8), cerebral vasospasm (Patent Document 9), atherosclerosis (Patent Document 10), traumatic brain damage (Patent Document 11) and neuropathic pain (Non-patent Document 9). However, such a rat-derived antibody is difficult to use clinically. To ensure that the rat antibody is available for use in humans, regions of rat origin in the antibody should be replaced as much as possible with those derived from human antibody (humanization) to thereby attenuate the immunogenicity of the antibody, while it is also necessary to maintain or improve the antigen specificity, affinity and neutralizing activity of the antibody.

Means to Solve the Problem

Under these circumstances, our efforts have been made to obtain a gene for the rat antibody #10-22 present in hybridomas producing the rat antibody #10-22 and to analyze the H and L chains of the rat antibody #10-22, variable regions thereof and CDRs thereof for their amino acid sequences to thereby select highly homologous human frameworks. After much trial and error, we have succeeded in preparing a humanized antibody whose antigen specificity, affinity and in vitro neutralizing activity are equal to or greater than those of the rat antibody.

On the other hand, a plurality of human-derived anti-HMGB1 monoclonal antibodies have been reported previously, and G4 is disclosed as a human antibody which has the highest inhibitory activity against binding of HMGB1 to RAGE and which binds to the C-terminal region of HMGB1 (WO2007/076200). Moreover, S6 is disclosed as a human antibody which most strongly inhibits the induction of TNFα secretion from macrophages/monocytes mediated by binding of HMGB1 to TLR4 (WO2007/001422). However, the humanized antibody of the present invention has now been demonstrated to be significantly higher than the above human antibody G4 in terms of inhibitory activity against binding of HMGB1 to RAGE and also to be advantageously superior to the above human antibody S6 in terms of in vitro inhibitory activity against the induction of TNFα secretion mediated by binding of HMGB1 to TLR4, and further to have a high death protection effect in sepsis model mice, thereby leading to the completion of the present invention.

Namely, the present invention provides a humanized anti-HMGB1 antibody which specifically binds to HMGB1 protein, as well as an antigen-binding fragment thereof, a pharmaceutical composition comprising such an antibody or antigen-binding fragment thereof, etc., as shown in [1] to [16] below.

[1] A humanized antibody specifically binding to an amino acid sequence (EEEDDDE (SEQ ID NO: 60)) present in the C-terminal domain of HMGB1 protein, or an antigen-binding fragment thereof, comprising a heavy chain variable region (VH) and a light chain variable region (VL), wherein
(i) the heavy chain variable region (VH) comprises:
(a) an amino acid sequence of heavy chain CDR1 comprising the amino acid sequence of SEQ ID NO: 7 or an amino acid sequence having mutations of deletion, substitution, insertion and/or addition of one to several amino acid residues in the amino acid sequence of SEQ ID NO: 7;
(b) an amino acid sequence of heavy chain CDR2 comprising the amino acid sequence of SEQ ID NO: 8 or an amino acid sequence having mutations of deletion, substitution, insertion and/or addition of one to several amino acid residues in the amino acid sequence of SEQ ID NO: 8; and
(c) an amino acid sequence of heavy chain CDR3 comprising the amino acid sequence of SEQ ID NO: 9 or an amino acid sequence having mutations of deletion, substitution, insertion and/or addition of one to several amino acid residues in the amino acid sequence of SEQ ID NO: 9, and
(ii) the light chain variable region (VL) comprises:
(a) an amino acid sequence of light chain CDR1 comprising the amino acid sequence of SEQ ID NO: 10 or an amino acid sequence having mutations of deletion, substitution, insertion and/or addition of one to several amino acid residues in the amino acid sequence of SEQ ID NO: 10;
(b) an amino acid sequence of light chain CDR2 comprising the amino acid sequence of SEQ ID NO: 11 or an amino acid sequence having mutations of deletion, substitution, insertion and/or addition of one to several amino acid residues in the amino acid sequence of SEQ ID NO: 11; and
(c) an amino acid sequence of light chain CDR3 comprising the amino acid sequence of SEQ ID NO: 12 or an amino acid sequence having mutations of deletion, substitution, insertion and/or addition of one to several amino acid residues in the amino acid sequence of SEQ ID NO: 12.

[2] The humanized antibody or antigen-binding fragment thereof according to [1] above, wherein
(i) the heavy chain variable region (VH) comprises:
(a) an amino acid sequence of heavy chain CDR1 comprising the amino acid sequence of SEQ ID NO: 7;
(b) an amino acid sequence of heavy chain CDR2 comprising the amino acid sequence of SEQ ID NO: 8; and
(c) an amino acid sequence of heavy chain CDR3 comprising the amino acid sequence of SEQ ID NO: 9, and
(ii) the light chain variable region (VL) comprises:
(a) an amino acid sequence of light chain CDR1 comprising the amino acid sequence of SEQ ID NO: 10;
(b) an amino acid sequence of light chain CDR2 comprising the amino acid sequence of SEQ ID NO: 11; and
(c) an amino acid sequence of light chain CDR3 comprising the amino acid sequence of SEQ ID NO: 12.

[3] The humanized antibody or antigen-binding fragment thereof according to [1] or [2] above, wherein
(i) the heavy chain variable region (VH) comprises the amino acid sequences of SEQ ID NOs: 43, 44, 45 and 46 as amino acid sequences of FR1, FR2, FR3 and FR4, respectively, wherein the amino acid sequences of FR1, FR2, FR3 and FR4 optionally have mutations of deletion, substitution, insertion and/or addition of one to several amino acid residues in the amino acid sequences of SEQ ID NOs: 43, 44, 45 and 46, respectively, and
(ii) the light chain variable region (VL) comprises the amino acid sequences of SEQ ID NOs: 47, 48, 49 and 50 as amino acid sequences of FR1, FR2, FR3 and FR4, respectively, wherein the amino acid sequences of FR1, FR2, FR3 and FR4 optionally have mutations of deletion, substitution, insertion and/or addition of one to several amino acid residues in the amino acid sequences of SEQ ID NOs: 47, 48, 49 and 50, respectively.

[4] The humanized antibody or antigen-binding fragment thereof according to any one of [1] to [3] above, wherein
(i) the heavy chain variable region (VH) comprises an amino acid sequence in which at least the two amino acid residues at positions 49 and 94 are amino acid residues (which are each alanine) derived from the rat antibody #10-22 H chain, and
(ii) the light chain variable region (VL) comprises an amino acid sequence in which at least two amino acid residues at positions 44 and 46 are amino acid residues (which are isoleucine and arginine, respectively) derived from the rat antibody #10-22 L chain.

[5] The humanized antibody or antigen-binding fragment thereof according to any one of [1] to [4] above, wherein
(i) the heavy chain variable region (VH) comprises an amino acid sequence having a 90% or more identity with the amino acid sequence of SEQ ID NO: 41, and
(ii) the light chain variable region (VL) comprises an amino acid sequence having a 90% or more identity with the amino acid sequence of SEQ ID NO: 42.

[6] The humanized antibody or antigen-binding fragment thereof according to any one of [1] to [5] above, wherein
(i) the heavy chain variable region (VH) comprises the amino acid sequence of SEQ ID NO: 41, and
(ii) the light chain variable region (VL) comprises the amino acid sequence of SEQ ID NO: 42.

[7] The humanized antibody or antigen-binding fragment thereof according to any one of [1] to [6] above, wherein the class (subclass) of the humanized antibody is IgG1(λ) or IgG2(λ).

[8] The humanized antibody or antigen-binding fragment thereof according to any one of [1] to [7] above, wherein the binding activity thereof to human HMGB1 protein (analyzed by ELISA assay) is 2-fold or higher than that of #10-22 chimeric antibody when compared at 250 ng/ml.

[9] The antibody according to any one of [1] to [7] above or an antigen-binding fragment thereof, wherein the activity thereof required for 50% inhibition (IC50) of binding of human HMGB1 protein to RAGE is 5 μg/mL (about 33 nM) or less.

[10] The antibody according to any one of [1] to [7] above or an antigen-binding fragment thereof, wherein the activity thereof required for 50% inhibition (IC50) of HMGB1 protein-stimulated TNF-α release in human PBMCs is 0.02 μg/mL (about 0.13 nM) or less.

[11] A pharmaceutical composition comprising the humanized antibody or antigen-binding fragment thereof according to any one of [1] to [10] above and a pharmaceutically acceptable carrier.

[12] The pharmaceutical composition according to [11] above for use in treatment or prevention of various HMGB1-related diseases induced by HMGB1 released from cells.
[13] The pharmaceutical composition according to [11] above for use in treatment or prevention of a HMGB1-related disease, wherein the HMGB1-related disease is any one of cerebral infarction, cerebral edema, cerebral vasospasm, traumatic brain damage, atherosclerosis, neuropathic pain, sepsis, arthritis, acute lung trauma, cerebral ischemia, renal ischemia, and hepatic ischemia, etc.
[14] An isolated nucleic acid encoding the amino acid sequence of the humanized antibody or antigen-binding fragment thereof according to any one of [1] to [10] above, or an isolated nucleic acid hybridizable with any of these nucleic acids under high stringent conditions.
[15] A recombinant expression vector comprising the isolated nucleic acid according to [14] above.
[16] A host cell transformed with the recombinant expression vector according to [15] above.

Effects of the Invention

In animal models of cerebral infarction, cerebral vasospasm, traumatic brain damage, atherosclerosis, neuropathic pain and so on, for which no therapeutic method has yet been sufficiently established, the rat antibody against HMGB1 used in the present invention has been shown to have the potential to serve as an agent which solves the problems lying in therapeutic and/or prophylactic methods for these relevant diseases. However, this antibody is difficult to use clinically because it is a rat-derived antibody. This rat antibody may be converted into a humanized antibody whose affinity and neutralizing activity are maintained or improved while maintaining its antigen specificity to thereby attenuate the immunogenicity of the rat antibody. Such a humanized antibody is able to provide new therapeutic and/or prophylactic methods for these many serious HMGB1-related diseases.

BRIEF DESCRIPTION OF THE DRAWINGS

FIG. 1 shows the HMGB1 reactivity of an antibody gene product cloned from #10-22 hybridoma.

FIG. 2 shows the HMGB1 reactivity of #10-22 chimeric antibody.

FIG. 16-a shows the epitope mapping of EV007156 by immunofluorescence staining. Full-length HMGB1 and six deletion constructs were each transfected into CHO-K1 cells, followed by staining with EV007156 to examine which of the deletion constructs was recognized by EV007156. A: CHO-K1, B: His-HMGB1 (full length), C: A-Box+B-Box, D: A-Box+C-tail, E: B-Box+C-tail, F: A-Box, G: B-Box, and H: +C-tail.

FIG. 16-b shows the epitope mapping of S6 by immunofluorescence staining. Full-length HMGB1 and six deletion constructs were each transfected into CHO-K1 cells, followed by staining with S6 to examine which of the deletion constructs was recognized by S6. A: CHO-K1, B: His-HMGB1 (full length), C: A-Box+B-Box, D: A-Box+C-tail, E: B-Box+C-tail, F: A-Box, G: B-Box, and H: +C-tail.

FIG. 16-c shows the epitope mapping of G4 by immunofluorescence staining. Full-length HMGB1 and six deletion constructs were each transfected into CHO-K1 cells, followed by staining with G4 to examine which of the deletion constructs was recognized by G4. A: CHO-K1, B: His-HMGB1 (full length), C: A-Box+B-Box, D: A-Box+C-tail, E: B-Box+C-tail, F: A-Box, G: B-Box, and H: +C-tail.

FIG. 17-a shows the epitope mapping of EV007156 by Western blotting. Full-length HMGB1 and individual deletion constructs were electrophoresed on a polyacrylamide gel, followed by detection with EV007156.

FIG. 17-b shows the epitope mapping of S6 by Western blotting. Full-length HMGB1 and individual deletion constructs were electrophoresed on a polyacrylamide gel, followed by detection with S6. Unlike EV007156, S6 recognizes regions containing B-Box.

FIG. 17-c shows the epitope mapping of G4 by Western blotting. Full-length HMGB1 and individual deletion constructs were electrophoresed on a polyacrylamide gel, followed by detection with G4. Unlike EV007156, G4 recognizes regions containing B-Box.

DESCRIPTION OF EMBODIMENTS

1. Explanation of Terms

Figure 3:
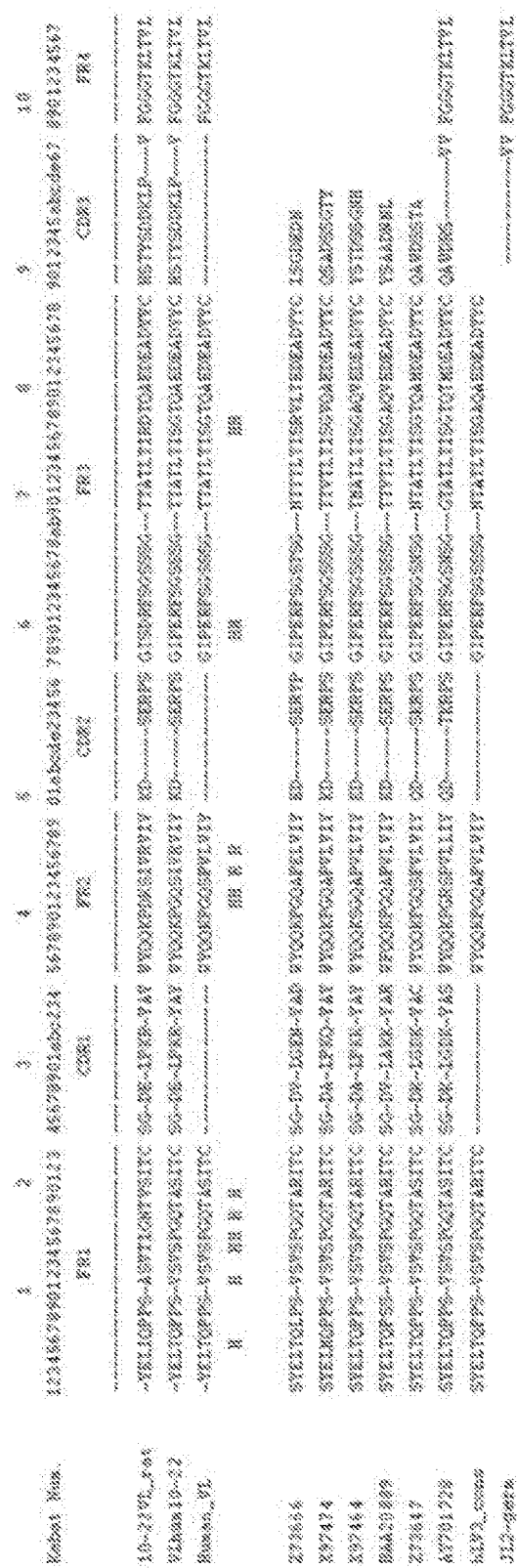
FIG. 3 shows the amino acid sequences of the L chain variable region of rat antibody #10-22 and its humanized antibody (VLhum10-22), along with human FR (Human_VL), and also shows the amino acid sequences of 8 human-derived antibody or germline (GenBank Accession Nos.: Z73666, X97474, X97464, BAA20889, Z73647 and AY701728, as well as hLV3_cons (consensus sequence in the human IGLV3 family: WO2011/080350) and JL2-germ (human lambda chain JL2 germline-derived sequence)) L chain variable regions highly homologous to the L chain FR sequence of #10-22. In this figure, Human_VL is a FR sequence modified to substitute consensus sequences in the above 8 human FR sequences for all 14 positions of the #10-22 FR sequence at which amino acid residues not observed in the above 8 human-derived sequences, i.e., "rat amino acid residues" are located (these positions are indicated with the symbol "H: human" or "R: rat" under the Human_VL sequence in the figure). In this figure, VLhum10-22 represents the L chain variable region of humanized antibody (EV007156), and its FR amino acid residues other than those at positions 44 and 46 are the same as in the above Human_VL sequence. With regard to the first position (1S) of L chain variable region, cleavage is known to occur between S1 and Y2, depending on the type of signal sequence used in human antibodies. For use as human FR (Human_VL) and humanized antibody (VLhum10-22) in the present invention, sequences whose "1S" will be cleaved off are selected, as in the case of the N-terminal end of the rat antibody #10-20 L chain variable region. It should be noted that the positions of amino acid residues in this figure are expressed in accordance with the numbering system of Kabat (http://vbase.mrc-cpe.cam.ac.uk/).

The scientific terms and technical terms used herein in relation to the present invention have the same meanings as commonly understood by those skilled in the art. Further, unless otherwise required by the context, singular terms shall include pluralities and plural terms shall include the singular. In general, the nomenclatures used in relation to the techniques described herein of cell and tissue culture, molecular biology, immunology, microbiology, genetics, protein and nucleic acid chemistry, as well as hybridization are well known in the art and commonly used.

The present invention relates to a humanized anti-HMGB1 antibody which specifically binds to HMGB1 protein and is effective for treatment and/or prevention of HMGB1-related diseases, as well as an antigen-binding fragment thereof. The embodiments of the present invention will be described in more detail below by clarifying the meanings of the words and phrases used in the present invention.

1) HMGB1 Protein

HMGB1 protein (or also referred to as "HMGB1 polypeptide") was considered to have the functions of chromatin structure maintenance, transcriptional activity regulation and so on. However, after its rediscovery as a late inflammatory mediator in sepsis, discoveries have been made one after another, showing that the HMGB1 protein plays important roles in inflammatory cytokine cascades in various diseases. HMGB1 is a 25 kDa protein composed of 215 amino acids rich in lysine residues and has an amino acid sequence which is very highly conserved among mammals. Its structure is composed of three domains, i.e., two DNA-binding domains called A-box and B-box, and a carboxyl-terminal domain consisting only of aspartic acid and glutamic acid residues (also referred to as the C-terminal domain or acidic tail). The A-box and B-box are each composed of about 80 highly conserved amino acid residues, and are strongly positively charged. The B-box has a TLR4 (toll-like receptor 4)-binding domain and a RAGE (receptor for advanced glycation end products)-binding domain. Upon binding to TLR4, HMGB1 induces the secretion of inflammatory cytokines from macrophages/monocytes. It should be noted that recent studies have shown that the TLR4/MD2 (myeloid differentiation protein 2) complex and further CD14 are involved as HMGB1 receptors in HMGB1-induced in vitro secretion of TNF-α and other cytokines (Mol. Med., 2013 (vol. 19) p. 88). On the other hand, upon binding to RAGE, HMGB1 induces the growth, differentiation and migration of endothelial cells and other somatic cells (including tumor cells) and the expression of their cell surface proteins. The third domain, i.e., the carboxyl-terminal end has a structure consisting of a 30 amino acid sequence composed only of aspartic acid and glutamic acid residues and is excessively negatively charged. The amino acid sequence of this C-terminal segment is also known to be highly conserved among mammals, only with a few differences. In particular, as to the RAGE-binding domain of HMGB1, it has been shown that upon inhibition of binding between HMGB1 and RAGE receptor in diseases such as ischemia-induced brain disorder (Non-patent Document 2) and sepsis associated with bacterial infection (Non-patent Document 3), it is possible to suppress HMGB1-RAGE-mediated amplification of inflammatory response in these HMGB1-related diseases.

HMGB1 used herein includes mammalian HMGB1s (e.g., human HMGB1, bovine thymus HMGB1, and rodent HMGB1s), and their amino acid sequences are disclosed in GenBank Accession No. CAG33144, GenBank Accession No. CAE48262, GenBank Accession No. CAI15600, NCBI Reference Sequence Accession No. NP_002119 and UniProtKB/Swiss-Prot Accession No. P09429 (all derived from humans), GenBank Accession No. BC102929 (derived from bovine thymus), GenBank Accession No. EGV93351 (derived from CHO-K1 cells), and UniProtKB/Swiss-Prot Accession No. P63159 (derived from rats), etc. The antibody of the present invention specifically binds to an amino acid sequence ((EEEDDDDE (SEQ ID NO: 60)) present in the C-terminal domain of HMGB1 protein. Not only human-derived HMGB1, but also the above bovine thymus-derived, CHO-derived and rat-derived HMGB1s have exactly the same amino acid sequence as shown in SEQ ID NO: 60 in their C-terminal domains.

2) HMGB1-Related Diseases

HMGB1 was considered at first to have the functions of chromatin structure maintenance, transcriptional activity regulation, DNA repair and so on. However, particularly after 1999 when HMGB1 was rediscovered as a late inflammatory mediator in sepsis, discoveries have been made one after another, showing that HMGB1 plays important roles in inflammatory cytokine cascades in various diseases. HMGB1-mediated inflammatory cytokine cascades are one of the factors responsible for harmful characteristics in many disorders, including inflammation and apoptosis, and hence are considered to be involved in HMGB1-related diseases as listed below. Particular examples (but not all) include: (i) conditions belonging to inflammatory diseases and autoimmune diseases, as exemplified by rheumatoid arthritis/seronegative arthropathy, osteoarthritis, inflammatory bowel disease, Crohn's disease, intestinal infarction, systemic lupus erythematosus, iritis/uveitis, optic neuritis, idiopathic pulmonary fibrosis, systemic angiitis/Wegener's granulomatosis, sarcoidosis, orchitis/vasectomy, systemic sclerosis and scleroderma; (ii) systemic inflammatory response syndrome, as exemplified by sepsis syndrome (including Gram-positive sepsis, Gram-negative sepsis, culture-negative sepsis, fungal sepsis, neutropenic fever, urinary sepsis, septic conjunctivitis), meningococcemia, traumatic hemorrhage, articulation difficulty, ionization radiation exposure, acute and chronic prostatitis, acute and chronic pancreatitis, appendicitis, digestive tract, gastric and duodenal ulcers, peritonitis, ulcerative, pseudomembranous, acute and ischemic colitis, diverticulitis, achalasia, cholangitis, cholecystitis, enteritis, and adult respiratory distress syndrome (ARDS); (iii) reperfusion injury, as exemplified by post-pump failure syndrome and ischemia reperfusion injury, as well as cardiovascular diseases, as exemplified by cardiac syncope syndrome, myocardial infarction and ischemia, atherosclerosis, venous thrombosis, endocarditis, pericarditis, congestive heart failure and restenosis; (iv) obstetric and gynecologic diseases, as exemplified by premature labor, endometriosis, abortion, vaginitis and sterility; (v) infectious diseases, as exemplified by HIV infection/HIV neuropathy, meningitis, hepatitis B and C, herpes simplex infection, septic arthritis, peritonitis, *E. coli* 0157:H7, pneumonia, epiglottitis, hemolytic uremic syndrome/thrombotic thrombocytopenic purpura, candidiasis, filariasis, amebiasis, malaria, dengue hemorrhagic fever, leishmaniasis, leprosy, toxic shock syndrome, streptococcal myositis, gas gangrene, *Mycobacterium tuberculosis, Mycobacterium avium-intracellulare, Pneumocystis carinii* pneumonia, pelvic inflammatory disease, orchitis/epididymitis, Legionnaires' disease, Lyme disease, influenza A, Epstein-Barr virus, cytomegalovirus, virus-associated hemophagocytic syndrome, and viral encephalitis/aseptic meningitis; (vi) allergic and atopic diseases, as exemplified by asthma, allergies, anaphylactic shock, immune complex disease, pollinosis, allergic rhinitis, eczema, allergic contact dermatitis, allergic conjunctivitis, and hypersensitivity pneumonitis; (vii) malignant tumors (conditions of liquid and solid tumors), as exemplified by ALL, AML, CML, CLL, Hodgkin's disease, non-Hodgkin's lymphoma, Kaposi's sarcoma, colorectal cancer, epipharyngeal cancer, malignant histiocytosis, and paraneoplastic syndrome/malignant hypercalcemia; (viii) transplantation diseases, as exemplified by organ transplant rejection and graft-versus-host disease; (ix) congenital diseases, as exemplified by cystic fibrosis, familial hemophagocytic lymphohistiocytosis and sickle cell anemia; (x) skin diseases, as exemplified by psoriasis, psoriatic arthritis and alopecia, as well as neurological diseases, as exemplified by neurodegenerative diseases (multiple sclerosis, migraine headache, headache, amyloid-associated conditions, prion disease/Creutzfeldt-Jakob disease, Alzheimer's disease and Parkinson's disease, multiple sclerosis, amyotrophic lateral sclerosis) and peripheral neuropathy, migraine headache, and headache; (xi) renal diseases, as exemplified by nephrotic syndrome, hemodialysis and uremia; (xii) iatrogenically intoxicated state, as exemplified by OKT3 therapy, anti-CD3 therapy, cytokine therapy, chemotherapy, radiation therapy and chronic salicylism; (xiii) metabolic or idiopathic diseases, as exemplified by Wilson's disease, hemochromatosis, α-1 antitrypsin deficiency, diabetes and diabetic complications, body weight reduction, anorexia, cachexia, obesity, Hashimoto's thyroiditis, osteoporosis, hypothalamic-pituitary-adrenal axis evaluation, and primary biliary cirrhosis; (xiv) ophthalmologic diseases, as exemplified by glaucoma, retinopathy and dry eye; as well as (xv) other conditions, as exemplified by multiple organ failure syndrome, muscular dystrophy, septic meningitis, atherosclerosis, epiglottitis, Whipple's disease, asthma, allergies, allergic rhinitis, organ necrosis, fervescence, sepsis, endotoxin shock, hyperpyrexia, eosinophilic granuloma, granulomatosis, sarcoidosis, infectious abortion, urethritis, pulmonary emphysema, rhinitis, alveolitis, bronchiolitis, pharyngitis, epithelial barrier dysfunction, pneumoconiosis, pleuritis, sinusitis, influenza, respiratory syncytial virus infection, disseminated bacteremia, hydatid cyst, dermatomyositis, heat burn, sunburn, urticaria, wart, wheal, angiitis, vasculitis, myocarditis, arteritis, periarteritis nodosa, rheumatic fever, celiac disease, encephalitis, cerebral embolism, Guillain-Barre syndrome, neuritis, neuralgia, iatrogenic complication/peripheral nerve lesion, spinal cord injury, paralysis, uveitis, arthritis, arthralgia, osteomyelitis, fasciitis, Paget's disease, gout, periodontal disease, synovitis, myasthenia gravis, Goodpasture's syndrome, Behcet's syndrome, ankylosing spondylitis, Buerger's disease, Reiter's syndrome, bullous dermatitis (bullous pemphigoid), pemphigoid and pemphigus vulgaris, and alopecia.

Recent studies have indicated that HMGB1 is not only localized in the nuclei of cells, but also migrates from the nuclei to the cytoplasm upon activation of macrophages and/or various cells of the immune system and is thereby released into the extracellular environment (active release), or alternatively, HMGB1 localized in the nuclei is rapidly released upon ischemia- or disorder-induced cell necrosis (passive release). Namely, these diseases in which HMGB1 is involved (HMGB1-related diseases) would be divided into two major groups. One is a group of diseases (e.g., septic shock) similar to microbial infection-induced immune responses, in which extracellular secretion of HMGB1 is observed at the late stage of inflammatory response upon activation of immunocytes. The other is a group of diseases (e.g., cerebral infarction) caused by cell injury due to non-microbial causes (e.g., ischemia, trauma and the like), in which rapid extracellular release of HMGB1 is observed upon cell injury, which in turn causes production of various cytokines. In the former group, active secretion of HMGB1 is caused from, e.g., infection-activated monocytes, macrophages and other cells, and HMGB1 acts as a late inflammatory mediator. Relevant diseases include sepsis, arthritis, atherosclerosis, various infections, and various immune diseases, etc. The latter group corresponds to cases where upon ischemia- or trauma-induced cell necrosis, HMGB1 having been localized in the nuclei is rapidly released into the extracellular environment within several hours (passive release) and thereby acts as an early inflammatory mediator to induce production of various inflammatory cytokines. Relevant diseases include cerebral infarction, traumatic brain injury, diseases due to ischemia during organ transplantation, myocardial infarction and so on.

3) Antibody

As used herein, the term "antibody" is intended to refer to an immunoglobulin molecule consisting of four polypeptide chains, i.e., two heavy (H) chains and two light (L) chains which are linked to each other via disulfide bonds. The monoclonal antibody in the context of the present invention is also composed of an immunoglobulin molecule comprising two heavy chains (H chains) and two light chains (L chains). Each H chain consists of an H chain variable region (also referred to as "HCVR" or "VH") and an H chain constant region (which consists of three domains, referred to as "CH1," "CH2," and "CH3," respectively (collectively referred as CH)). Each L chain consists of an L chain variable region (also referred to as "LCVR" or "VL") and an L chain constant region (which consists of one domain, also referred to as "CL"). Such a variable region refers to a region upstream of the beginning of each constant region (also referred to as the invariable region).

Heavy chains are classified into γ chain, μ chain, α chain, δ chain and ε chain, depending on differences in their constant region, and five classes (isotypes) of immunoglobulins, i.e., IgG, IgM, IgA, IgD and IgE are formed based on these differences. Further, in human cases, IgG has four subclasses, i.e., IgG1 to IgG4. On the other hand, light chains are classified into κ chain and λ chain, depending on differences in their constant region.

On the other hand, VH and VL are important in terms of being involved in the binding specificity of antibody. Since an antibody interacts with its target antigen through amino acid residues in VH and VL, amino acid sequences within these variable regions vary more greatly among individual antibodies than sequences located outside the variable regions. Moreover, VH and VL can also be subdivided into regions referred to as framework regions (FRs), which are kept more constant among various antibodies, and hypervariable regions referred to as complementarity determining regions (CDRs). VH and VL are each composed of three CDRs and four FRs, which are arranged in the order of FR1, CDR1, FR2, CDR2, FR3, CDR3 and FR4 from the amino-terminal end to the carboxy-terminal end (see FIGS. 3 and 6).

FR4 is also referred to as the D/J region in the case of the H chain variable region and referred to as the J region in the case of the L chain variable region. The distribution of amino acids in each region is in accordance with the definition of Kabat (see http://www.bioinf.org.uk/abs/#kabatnum), in principle.

Although there are also descriptions herein about the germline-derived sequences of these antibodies, the classes (families) and gene numbers of these germline-derived sequences will be expressed principally in accordance with "VBASE2 ID" described in VBASE2 (http://www.vbase2.org/vbase2.php). More specifically, for example, the family of λ (lambda) light chain variable region sequences will be expressed as, e.g., IGLV1, IGLV2 or IGLV3, and the "VBASE2 ID" numbers of their genes will be expressed as, e.g., humIGLV104 (=IGLV3-1*01) and humIGLV079 (=IGLV3-25*02). In addition, the family of λ chain J segments will be expressed as, e.g., JL1, JL2 or JL3. Likewise, the family of heavy chain variable regions will be expressed as, e.g., IGHV1, IGHV2, IGHV3 or IGHV4, and their gene numbers will be expressed as, e.g., humIGVH048 (=IGHV3-73*01), humIGHV240 (=IGHV3-72) and humIGHV025 (=IGHVH-15), principally in accordance with "VBASE2 ID" described in VBASE2 (http://www.vbase2.org/vbase2.php). In addition, the family of H chain J segments will be expressed as, e.g., JH1, JH2, JH3 or JH4.

4) "Antigen-Binding Fragment" of Antibody (or Simply "Antibody Fragment")

As used herein, the term "antigen-binding fragment" of antibody (or simply "antibody fragment") refers to one or more fragments (e.g., VH) of the antibody, each having the ability to specifically bind to the antigen (HMGB1 protein). It should be noted that such a fragment is intended to also include a peptide having the minimal amino acid sequence specifically binding to the antigen. Examples of binding portions encompassed within the term "antigen-binding fragment" of antibody include (i) a Fab fragment, (ii) a F(ab')₂ fragment, (iii) a Fd fragment consisting of VH and CH1 domains, (iv) a Fv fragment consisting of VL and VH domains of a single arm of antibody, (v) a dAb fragment consisting of a VH domain (Nature 341:544-546, 1989), (vi) an isolated complementarity determining region having sufficient framework to specifically bind, (vii) a bispecific antibody, and (viii) a multispecific antibody, etc. It should be noted that when used herein without any particular distinction, the term "antibody" is intended to include not only a full-length antibody, but also these "antigen-binding fragments."

These are each an antibody specifically binding to mammalian HMGB1, which is capable of binding to an epitope site in this HMGB1 or to a HMGB1 fragment, etc. As used herein, the term "anti-HMGB1 antibody," "antibody capable of neutralizing HMGB1," "anti-HMGB1 protein antibody," "antibody specifically binding to a HMGB1 fragment" or "antibody capable of neutralizing the biological activity of HMGB1" is intended to refer to an antibody that inhibits the biological activity of HMGB1 through binding to HMGB1.

5) Antibody Binding to HMGB1 Protein, or Humanized Antibody Thereof

The present invention provides an antibody specifically binding to mammalian HMGB1. In particular, the antibody of the present invention specifically binds to an amino acid sequence (EEEDDDDE (SEQ ID NO: 60)) present in the C-terminal domain of the HMGB1 protein. As used herein, the term "anti-HMGB1 antibody," "antibody capable of neutralizing HMGB1," "anti-HMGB1 protein antibody," "antibody specifically binding to a HMGB1 fragment" or "antibody capable of neutralizing the biological activity of HMGB1" is intended to refer to an antibody that inhibits the biological activity of HMGB1 through binding to the above epitope site in HMGB1. As described above, the C-terminal amino acid sequence (SEQ ID NO: 60) of HMGB1 is also very highly conserved among mammals; and hence it is not always necessary to use human-derived HMGB1 for obtaining an antibody against the above epitope in human HMGB1, and rat-derived, CHO-derived or bovine thymus-derived HMGB1 protein may also be used for this purpose.

It should be noted that a humanized antibody against HMGB1 in the context of the present invention is intended to mean a full-length antibody or an antigen-binding fragment thereof, which is prepared by grafting CDRs from the above rodent-derived anti-HMGB1 antibody used as a donor onto human-derived FRs, in principle, and which comprises rodent-derived amino acid residues as a part of the FR sequence and has HMGB1-binding activity or HMGB1-neutralizing activity equal to or greater than that of the original rodent-derived antibody or a chimeric antibody thereof. Based on the amino acid sequences representing variable regions and/or the amino acid sequences of complementarity determining regions (CDRs) disclosed in the present patent application, it is easy to obtain a humanized antibody specifically binding to HMGB1 protein which has higher binding activity or is less immunogenic, or an antigen-binding fragment thereof, when using well-known techniques in the art, and such a humanized antibody falls within the technical scope of the present invention.

6) Chimeric Antibody and Humanized Antibody

The term "chimeric antibody" refers to an antibody whose L and H chain genes are constructed typically by genetic engineering from immunoglobulin genes belonging to different species. Typically, variable region sites derived from mouse monoclonal antibody are joined to constant region sites from human-derived IgG1 or IgG4. Details on typical procedures for obtaining chimeric antibody through modification by genetic engineering techniques are disclosed in U.S. Pat. No. 483,457 (Genentech's patent) and so on. The term "humanized antibody" refers to an antibody comprising at least one chain comprising variable region framework residues substantially from a human antibody chain (referred to as the acceptor immunoglobulin or antibody) and at least one complementarity determining region substantially from mouse antibody (also referred to as the donor immunoglobulin or antibody). Typically, a chimeric antibody is further modified to have a structure close to the human sequence including FR sequences, thereby reducing the immunogenicity of the non-human antibody in humans. Representative procedures for this modification are disclosed in EP0239400 (MRC's patent), WO90/07861 (Protein Design Labs's patent) or EP0626390 (Celltech's patent), etc. For humanization, i.e., integration of mouse CDRs into human variable region FRs, it is necessary to increase the possibility of ensuring the retention of their correct spatial orientation. To achieve this end, human antibody variable region FR sequences to be used are obtained from a human antibody showing high sequence identity with donor variable region FR sequences. Human antibody sequences used for this purpose may be naturally occurring human antibody sequences or may be human antibody consensus sequences or germline-derived sequences, etc.

7) Equivalents

Amino acid sequences which are not only mutated to have deletion, substitution, insertion or addition of one or several amino acid residues in the amino acid sequence of the antibody of the present invention, or any combination of two or more of these modifications, but also retain the original antibody activity (e.g., antigen-binding ability) are equivalents of the present invention. In these cases, deletion, substitution, insertion or addition of one or several amino acid residues may occur at any one or more amino acid positions in the same sequence, or alternatively, two or more of deletion, substitution, insertion and addition may occur at the same time.

Amino acids constituting naturally occurring proteins can be grouped depending on the properties of their side chains. For example, they may be divided into groups of amino acids having similar properties, e.g., a group of aromatic amino acids (tyrosine, phenylalanine, tryptophan), a group of basic amino acids (lysine, arginine, histidine), a group of acidic amino acids (aspartic acid, glutamic acid), a group of neutral amino acids (serine, threonine, asparagine, glutamine), a group of amino acids with hydrocarbon chains (alanine, valine, leucine, isoleucine, proline), and a group of other amino acids (glycine, methionine, cysteine).

Examples of interchangeable amino acid residues including unnatural amino acids are as shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine, tryptophan.

Incidentally, amino acid residue substitution at a certain site of the antibody sequence is expressed herein as "ANB," by way of example. In this expression, "N" represents the number for this substitution site (expressed in accordance with Kabat Numbering), "A" represents an amino acid residue before substitution, which is expressed with one letter of the alphabet, and "B" represents an amino acid residue after substitution, which is expressed with one letter of the alphabet.

The identity of amino acid sequences or nucleotide sequences can be determined by using the algorithm of Karlin and Altschul, BLAST (PNAS, 1990 (vol. 87) p. 2264; PNAS, 1993 (vol. 90) p. 5873). Based on the algorithm of BLAST, programs called BLASTN and BLASTX have been developed (J Mol Biol, 1990 (vol. 215) p. 403). If BLASTN is used for nucleotide sequence analysis, parameters may be set to, for example, score=100 and wordlength=12. Likewise, if BLASTX is used for amino acid sequence analysis, parameters may be set to, for example, score=50 and wordlength=3. If BLAST and Gapped BLAST programs are used, default parameters in each program may be used. Alternatively, to determine the identity of amino acid sequence between proteins, the amino acid sequences of two proteins to be compared may be aligned to visually count amino acid residues matched between the proteins, followed by calculation according to the formula "(the number of matched amino acid residues/the number of amino acid residues in the entire protein)×100(%)."

2. How to Prepare Antibody-Producing Hybridomas for Use in the Present Invention To prepare rat-derived monoclonal antibody-producing hybridomas for use in the present invention by using the above HMGB1 antigen protein, rats are immunized with this antigen, and lymph cells are collected from these animals and then fused with myeloma cells in a standard manner to obtain hybridomas, whereby rat anti-HMGB1 monoclonal antibody-producing hybridomas can be obtained.

Namely, first of all, for example, bovine thymus-derived HMGB1 is mixed with Freund's complete adjuvant or Freund's incomplete adjuvant, and this mixture is used as an immunogen to immunize rats. Administration of the immunogen during immunization may be accomplished by any of subcutaneous injection, intraperitoneal injection, intravenous injection or intramuscular injection, preferably by subcutaneous injection or intraperitoneal injection. Immunization may be conducted once or several times at appropriate intervals, preferably several times at intervals of 1 week to 5 weeks. Then, lymph nodes are collected from the immunized animals in a standard manner, and lymph node cells obtained aseptically therefrom are subjected to cell fusion with mouse myeloma cells, followed by ELISA or other assays to confirm their binding ability to HMGB1. By repeating the cloning operation for desired antibody-producing hybridomas, monoclonal antibody-producing cells can be obtained.

3. How to Obtain a Gene for the Rat Antibody of the Present Invention

Total RNA is purified from rat antibody-producing hybridoma cells in a standard manner and then used to synthesize cDNA. From the resulting cDNA, the full-length H and L chain antibody genes are amplified by PCR with their respective primers to obtain their respective gene fragments. These fragments may each be ligated to a vector for expression in eukaryotic cells, thereby cloning a gene for the antibody. To determine the amino acid sequences of these antibody H and L chains, the plasmid vectors encoding these chains are confirmed for their nucleotide sequences with an ABI sequencer, and the amino acid sequence of the antibody can be determined based on these nucleotide sequences.

4. How to Obtain a Humanized Antibody

An example will be described below, where a humanized antibody is prepared from a rodent antibody. The procedures described below are fundamental procedures for humanization, and variations thereof are also possible as a matter of course. For example, amino acids in complementarity determining regions (CDRs) in the rat antibody variable region are first determined in accordance with "the definition of Kabat et al." and/or "the definition of Chothia." These rat antibody CDR sequences are grafted onto human antibody FRs serving as an acceptor to design a variable region amino acid sequence having the rat antibody CDRs and the human antibody FRs. A nucleotide sequence is designed for DNA encoding this variable region amino acid sequence, and a variable gene fragment having the same nucleic acid sequence as designed is prepared by PCR and gene recombination technology. Then, this variable region gene is ligated to a constant region gene for appropriate class of human antibody, preferably a constant region gene for IgG class of antibody, to thereby prepare a humanized antibody gene. Then, this humanized antibody gene is ligated to an appropriate expression vector and introduced into cultured cells. Finally, these cultured cells are cultured, and a humanized antibody can be obtained from their culture supernatant.

In the above procedures for humanized antibody preparation, the complementarity determining region genes in the rat antibody variable region gene can be determined from the range of complementarity determining regions according to "the definition of Kabat" mentioned above. However, only in the case of H chain CDR1, a region according to both "the definition of Kabat" and "the definition of Chothia" is intended herein for use as CDR1. Moreover, the positions of amino acid residues in the variable region are expressed in accordance with the numbering system of Kabat (see http://www.bioinf.org.uk/abs/#kabatnum, and http://vbase.mrc-cpe.cam.ac.uk/).

On the other hand, for use as human antibody framework region genes serving as a template, sequences highly homologous to the amino acid sequences of framework regions in the above rat antibody may be selected, for example, from among human antibody sequences or human antibody germline sequences or human antibody germline consensus sequences, etc., and nucleotide sequences encoding the thus selected amino acid sequences may be prepared in a standard manner and provided for use.

The above rat antibody complementarity determining region genes and the above human antibody framework region genes serving as a template are ligated to each other, and this gene fragment is further ligated to a human antibody constant region gene to thereby prepare a humanized antibody gene (hereinafter simply referred to as the "humanized antibody gene").

In general, in the case of humanized antibodies having amino acid substitutions only in their complementarity determining regions, it should be noted that they often have greatly reduced antigen-binding activity in comparison with their original rat antibody. For this reason, it is often attempted to conduct such substitutions together with grafting of some amino acids from the donor rat antibody and near the complementarity determining regions, by way of example. The humanized antibodies obtained above will have antigen-binding activity equal to or greater than that of their original rat antibody and will overcome the problems of antigenicity induction and half-life reduction, etc., when compared to the rat antibody. However, with regard to amino acid substitutions required to obtain humanized antibodies having binding activity or neutralizing activity equal to or greater than that of their original rat antibody, there is no particular rule and much trial and error will therefore be required.

5. The Humanized Antibody of the Present Invention or an Antigen-Binding Fragment Thereof In one embodiment, the present invention provides a humanized antibody which specifically binds to HMGB1 and is capable of neutralizing the biological activity of HMGB1 (hereinafter referred to as the antibody of the present invention) or an antigen-binding fragment thereof. Tables 1, 2 and 3 show SEQ ID NOs of the amino acid sequences identified in the present invention for rat anti-HMGB1 antibody (#10-22), a chimeric antibody thereof and a humanized antibody thereof, as well as SEQ ID NOs of the human antibody sequences or human germline-derived amino acid sequences used as human FR sequences for reference.

The humanized antibody of the present invention or an antigen-binding fragment thereof include a humanized antibody comprising the full-length, variable region or framework region amino acid sequences of EV007156 whose SEQ ID NOs are shown in Table 3, and an antigen-binding fragment thereof, as well as a humanized antibody comprising amino acid sequences equivalent to the above amino acid sequences, and an antigen-binding fragment thereof.

TABLE 1

SEQ ID NOs of rat #10-22 antibody-related amino acid sequences

| | Rat #10-22 antibody | | | | | |
|---|---|---|---|---|---|---|
| | Full-length (+signal) | Full-length (−signal) | Variable region sequence | CDR sequence (amino acid sequence) | | |
| | | | | CDR1 | CDR2 | CDR3 |
| H chain | 1 | 3 | 5 | 7 | 8 | 9 |
| L chain | 2 | 4 | 6 | 10 | 11 | 12 |

TABLE 2

SEQ ID NOs of human-derived variable region amino acid sequences and so on

| Variable region | SEQ ID NO | Sequence name (Accession No.); site |
|---|---|---|
| L region | 15 | Z73666 |
| | 16 | X97474 |
| | 17 | X97464 |
| | 18 | BAA20889 |
| | 19 | Z73647 |
| | 20 | AY701728 |
| | 21 | hLV3_cons; FR1 |
| | 22 | hLV3_cons; FR2 |
| | 23 | hLV3_cons; FR3 |
| | 24 | JL2-germ |
| VH region | 29 | AM940224 |
| | 30 | DQ926386 |
| | 31 | FJ488688 |
| | 32 | HM855402 |
| | 33 | DQ840895 |
| | 34 | Z12332 |

TABLE 3

SEQ ID NOs of amino acid sequences of chimeric antibody, Human_VH or VL, and humanized antibody (EV007156)

| | Chimeric antibody | | | | | EV007156 | | | | | |
|---|---|---|---|---|---|---|---|---|---|---|---|
| | Full-length | Human_VH or VL | | | | Full-length | Variable region | FR1 | FR2 | FR3 | FR4 |
| | | FR1 | FR2 | FR3 | FR4 | | | | | | |
| H chain | 13 | 35 | 36 | 37 | 38 | 39 | 41 | 43 | 44 | 45 | 46 |
| L chain | 14 | 25 | 26 | 27 | 28 | 40 | 42 | 47 | 48 | 49 | 50 |

Upon examination of the L chain variable regions of the IGLV3-family registered in GenBank or elsewhere, there are found many cases reporting that the N-terminal end starts with "S." In the sequences of the IGLV3-family, cleavage may also occur upstream of "Y" located at the second position when the 3j amino acid sequence (MAWTALLLSLLAHFTGSVA) or the 3r amino acid sequence (MAWIPLFLGVLAYCTGSVA) is selected as a signal sequence. For this reason, in the present invention, a sequence whose first position "S" has been cleaved off is selected for use as a human FR sequence (SEQ ID NOs: 25 to 28; expressed as Human_VL in FIG. 3) which serves as a template for humanization.

A preferred antibody or antigen-binding fragment of the present invention is, for example, a humanized antibody or an antigen-binding fragment thereof, whose heavy chain variable region comprises (a) an amino acid sequence of heavy chain CDR1 comprising the amino acid sequence of SEQ ID NO: 7, (b) an amino acid sequence of heavy chain CDR2 comprising the amino acid sequence of SEQ ID NO: 8, and (c) an amino acid sequence of heavy chain CDR3 comprising the amino acid sequence of SEQ ID NO: 9, and whose light chain variable region comprises (a) an amino acid sequence of light chain CDR1 comprising the amino acid sequence of SEQ ID NO: 10, (b) an amino acid sequence of light chain CDR2 comprising the amino acid sequence of SEQ ID NO: 11, and (c) an amino acid sequence of light chain CDR3 comprising the amino acid sequence of SEQ ID NO: 12. However, as long as the intended monoclonal antibody specifically binds to the amino acid sequence of SEQ ID NO: 60 (EEEDDDDE) present in the C-terminal domain of HMGB1 and is capable of neutralizing its biological activity, there is no need to be limited only to the above combination of CDR sequences, and these six CDR sequences of SEQ ID NOs: 7 to 12 may be mutated to have deletion, substitution, insertion or addition of one to several amino acid residues (more specifically 1 to 9 residues, 1 to 8 residues, 1 to 7 residues, 1 to 6 residues, 1 to 5 residues, 1 to 4 residues, 1 to 3 residues, 1 to 2 residues, or a single residue) or any combination of two or more of these modifications. In light of the fact that the present invention is directed to a humanized antibody, a more preferred embodiment of the present invention is, of course, an antibody comprising these six CDR sequences and FR amino acid sequences in which at least four amino acid residues at positions 49 and 94 in the H chain and at positions 44 and 46 in the L chain are of rat origin, but the remainder of these FR amino acid sequences are desirably human-derived sequences.

When the human FR sequence in the L chain variable region of the present invention (human_VL; SEQ ID NOs: 25 to 28 (in order of FR1, FR2, FR3 and FR4 sequences)) is compared with human λ (lambda) chain germline LV3 family-derived sequences, segments corresponding to FR1, FR2 and FR3 share high identity with human λ (lambda) chain IGHLV3 family germlines humIGLV104 (=IGLV3-1*01), humIGLV034 (=IGLV3-25*03), humIGLV079 (=IGLV3-25*02), humIGLV135, humIGLV094 (=IGLV3-10*01) and humIGLV077 (=IGLV3-27*01) (whose gene numbers are expressed in accordance with "VBASE2 ID"), with differences only in a few residues (less than 10 residues). Moreover, the consensus sequence of IGLV3 (see, e.g., WO2011/080350) also differs from the above Human_VL only in a few amino acid residues. On the other hand, a segment corresponding to FR4 (SEQ ID NO: 28) in the human FR sequence was found to have the same amino acid sequence as human λ (lambda) chain germline J segments JL2 (SEQ ID NO: 22; GenBank Accession No. M15641), JL3 (VVFGGGTKLTVL) and JL7 (AVFGGGTQLTVL). With regard to the human FR sequence in the H chain variable region intended herein (SEQ ID NOs: 35 to 38; expressed as Human_VH in FIG. 6), upon comparison with human H chain germline IGHV3 family-derived sequences, the sequences of segments corresponding to FR1, FR2 and FR3 were found to be 100% identical with humIGHV048 (=HV3-73*1; GenBank Accession No. L15467) and IGHV3-73*2 (GenBank Accession No. AM940224). Further, upon examination of IGHV3 family sequences, those sharing high identity with humIGHV048 are humIGHV025, humIGHV178, humIGHV215 and humIGHV240 (all expressed in accordance with VBASE2 ID), and differences from the amino acid sequence encoded by humIGHV048 are found only in 5 or less amino acid residues. Thus, there are several germline sequences sharing high identity in the IGHV3 family. The consensus sequence of IGHV3 (see, e.g., WO2011/080350) also differs from the above Human_VH only in a few amino acid residues. Moreover, the sequence of FR4 segment (WGQGTLVTVSS) in Human_VL is identical with human H chain germline J segments JH1, JH4 and JH5 (see GenBank Accession No. J00256).

In view of the foregoing, a more preferred embodiment of the present invention also includes a humanized antibody or an antigen-binding fragment thereof, (i) whose heavy chain variable region (VH) comprises the amino acid sequences of SEQ ID NOs: 7, 8 and 9 as amino acid sequences of CDR1, CDR2 and CDR3, respectively, and the amino acid sequences of SEQ ID NOs: 43, 44, 45 and 46 as amino acid sequences of FR1, FR2, FR3 and FR4, respectively, provided that the amino acid sequences of FR1, FR2, FR3 and FR4 may be mutated to have deletion, substitution, insertion and/or addition of one to several amino acid residues (more specifically 1 to 9 residues, 1 to 8 residues, 1 to 7 residues, 1 to 6 residues, 1 to 5 residues, 1 to 4 residues, 1 to 3 residues, 1 to 2 residues, or a single residue) in the amino acid sequences of SEQ ID NOs: 43, 44, 45 and 46, respectively, and (ii) whose light chain variable region (VL) comprises the amino acid sequences of SEQ ID NOs: 10, 11 and 12 as amino acid sequences of CDR1, CDR2 and CDR3, respectively, and the amino acid sequences of SEQ ID NOs: 47, 48, 49 and 50 as amino acid sequences of FR1, FR2, FR3 and FR4, respectively, provided that the amino acid sequences of FR1, FR2, FR3 and FR4 may be mutated to have deletion, substitution, insertion and/or addition of one to several amino acid residues (more specifically 1 to 9 residues, 1 to 8 residues, 1 to 7 residues, 1 to 6 residues, 1 to 5 residues, 1 to 4 residues, 1 to 3 residues, 1 to 2 residues, or a single residue) in the amino acid sequences of SEQ ID NOs: 47, 48, 49 and 50, respectively, as long as it is a monoclonal antibody or an antigen-binding fragment thereof, which specifically binds to HMGB1, preferably the amino acid sequence of SEQ ID NO: 60 (EEEDDDDE) present in the C-terminal domain of HMGB1, and is capable of neutralizing its biological activity. In the above FR sequences, more preferred are those in which at least two amino acid residues at positions 49 and 94 in the H chain are amino acid residues derived from the rat antibody #10-22 and at least two amino acid residues at positions 44 and 46 in the L chain are derived from the rat antibody #10-22. Further, the most preferred is a humanized antibody or an antigen-binding fragment thereof, which comprises FR sequences contained in a heavy chain variable region (VH) comprising the amino acid sequence of SEQ ID NO: 33 and in a light chain variable region (VL) comprising the amino acid sequence of SEQ ID NO: 34, respectively. In this case, a humanized antibody or an antigen-binding fragment thereof, which comprises a heavy chain variable region (VH) comprising an amino acid sequence having a 90% or more identity with the amino acid sequence of SEQ ID NO: 33 and a light chain variable region (VL) comprising an amino acid sequence having a 90% or more identity with the amino acid sequence of SEQ ID NO: 34 also falls within the present invention, as long as it is a monoclonal antibody which specifically binds to the amino acid sequence of SEQ ID NO: 60 (EEEDDDDE) present in the C-terminal domain of HMGB1 and is capable of neutralizing its biological activity.

Moreover, classes (subclasses) preferred for the humanized antibody of the present invention are exemplified by IgG1(λ) and IgG2(λ), although IgG3(λ) and IgG4(λ) also fall within the present invention.

6. Nucleic Acid Encoding the Antibody of the Present Invention

According to another embodiment of the present invention, the present invention also encompasses a nucleic acid (nucleotide) encoding a humanized antibody or an antigen-binding fragment thereof, which specifically binds to HMGB1, preferably the amino acid sequence of SEQ ID NO: 60 (EEEDDDDE) present in the C-terminal domain of HMGB1, and is capable of neutralizing its biological activity, i.e., a nucleic acid encoding the amino acid sequences of SEQ ID NOs: 7 to 9, the amino acid sequences of SEQ ID NOs: 10 to 12, or the amino acid sequence of 39, 40, 41 or 42, as well as an isolated nucleic acid sharing high identity with this nucleic acid. As used herein, the phrase "sharing high identity" is intended to mean having a sequence identity sufficient to allow hybridization with a given nucleic acid sequence under high stringent conditions, for example, an identity of 60%, 70%, 80%, 90%, 95% or higher. There is provided an isolated nucleic acid selected from among nucleic acids hybridizable under high stringent conditions. The above nucleic acid is preferably DNA or RNA, and more preferably DNA.

The term "high stringent conditions" refers to, for example, conditions of 5×SSC, 5×Denhardt's solution, 0.5% SDS, 50% formamide and 50° C. (see, e.g., J. Sambrook et al., Molecular Cloning, A Laboratory Manual 2nd ed., Cold Spring Harbor Laboratory Press (1989), particularly Section 11.45 "Conditions for Hybridization of Oligonucleotide Probes"). Under these conditions, it can be expected that a polynucleotide (e.g., DNA) sharing a higher identity is more efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

Nucleic acids hybridizable under the above high stringent conditions include nucleic acids sharing an identity of, e.g., 70% or higher, 80% or higher, 90% or higher, 95% or higher, 97% or higher, or 99% or higher with a nucleic acid encoding the intended amino acid sequence.

The identity of nucleotide sequences can be determined by using the identity search algorithm mentioned above or the like (Proc. Natl. Acad. Sci. USA 872264-2268, 1990; Proc Natl Acad Sci USA 90: 5873, 1993).

It should be noted that a nucleic acid preferred as a humanized anti-HMGB1 antibody in the present invention is an isolated gene encoding the amino acid sequence of SEQ ID NO: 39 or 41 or an isolated gene encoding the amino acid sequence of SEQ ID NO: 40 or 42, or an isolated nucleic acid hybridizable with any of these nucleic acids (DNAs) under high stringent conditions. Further, a more preferred nucleic acid is an isolated nucleic acid (DNA) encoding both of the amino acid sequences of SEQ ID NOs: 41 and 42, and one of the most preferred nucleic acids is an isolated nucleic acid encoding both of the amino acid sequences of SEQ ID NOs: 39 and 40.

7. The Vector and Host Cell of the Present Invention and their Use for Antibody Preparation The present invention also relates to a vector comprising the above nucleic acid integrated thereinto and a host cell transformed with this vector, as well as their use for antibody preparation.

The antibody of the present invention may also be prepared as a recombinant human antibody in a known manner (see, e.g., Nature, 312:643, 1984, Nature, 321:522, 1986). For example, the antibody of the present invention may be prepared by culturing host cells transformed with the vector of the present invention and purifying the produced antibody from the culture supernatant or the like. More specifically, cDNAs encoding VH and VL may be inserted into separate expression vectors for animal cells, each comprising a gene encoding human antibody CH or human antibody CL prepared from the same cell or another human cell, to thereby construct human antibody expression vectors, which may then be introduced into animal cells and expressed therein to thereby prepare the desired antibody.

As a vector into which a nucleic acid encoding VH or VL of the antibody of the present invention is to be integrated, preferred is a vector or a high expression vector, which is commonly used for expression of protein genes and so on, and is particularly suitable for antibody gene expression, without necessarily being limited thereto. Preferred examples include vectors carrying EF promoter and/or CMV enhancer. Moreover, in most cases, nucleic acids encoding VH and VL are integrated into separate expression vectors and the thus prepared expression vectors are co-transfected into a host cell, although both nucleic acids may be integrated into a single expression vector.

As a host cell to be transformed with the expression vector(s), preferred is a cell which is commonly used for expression of protein genes and so on, and is particularly suitable for antibody gene expression, without necessarily being limited thereto. Examples include bacteria (e.g., *E. coli*), actinomycetes, yeast, insect cells (e.g., SF9), and mammalian cells (e.g., COS-1, CHO, myeloma cells, YB2/0 cells).

For industrial production of recombinant antibodies, it is usual to use recombinant animal cell lines (e.g., CHO cell line) which ensure stable high production of recombinant antibodies. For preparation and cloning of such a recombinant cell line, and for gene amplification and screening for high expression, known techniques may be used (see, e.g., Omasa T.: J. Biosci. Bioeng., 94, 600-605, 2002).

The present invention encompasses not only an antibody composed of two heavy chains and two light chains, but also an antigen-binding fragment of the antibody of the present invention. Examples of an antigen-binding fragment include: Fab (fragment of antigen binding), Fab' and F(ab')2; active fragments of antibody linked via a linker or the like, as exemplified by single chain antibody (single chain Fv: scFv) and disulfide-stabilized antibody (disulfide stabilized Fv: dsFv); and a peptide containing an active fragment of antibody, as exemplified by a peptide containing CDR. These fragments may be prepared in any known manner, e.g., by treating the antibody of the present invention with an appropriate protease or by gene recombination techniques.

Antibody purification may be conducted by using known purification means such as salting out, gel filtration, ion exchange chromatography or affinity chromatography. More specifically, for purification of anti-HMGB1 antibody, the selected cells may be grown in a dish, a roller bottle, a 2 liter spinner flask or any other culture system. The resulting culture supernatant may be filtered, concentrated and then applied to affinity chromatography on Protein A- or Protein G-sepharose (GE Healthcare), etc., to thereby purify the desired protein. After buffer replacement with PBS, the concentration may be determined by OD280 or preferably by nepherometer analysis. Isotype determination may be conducted in a manner specific to each isotype antigen. The thus obtained humanized anti-HMGB1 antibody can be expected to be less immunogenic than the original rat antibody.

By using recently developed techniques for modification of antibody sugar chain moieties or for modification and substitution of constant regions, it is possible to obtain an antibody with modified effector activity, etc., and the humanized antibody thus obtained also falls within the technical scope of the present invention. Furthermore, the antibody may be subjected to techniques for partial substitution in the Fc region (see WO2006/071877), which are intended to ensure that the antibody is provided with the ability to resist proteases and thereby available for oral administration. The thus obtained antibody or an antigen-binding fragment thereof also falls within the technical scope of the present invention.

8. Pharmaceutical Composition Comprising the Antibody of the Present Invention Then, the present invention provides a pharmaceutical composition for treatment or prevention of HMGB1-related diseases, which comprises the above antibody or an antigen-binding portion thereof and a pharmaceutically acceptable carrier.

In particular, the humanized anti-HMGB1 antibody of the present invention or an antigen-binding fragment thereof specifically binds to HMGB1 and has high activity to neutralize the biological activity of HMGB1, and is therefore useful as a prophylactic or therapeutic agent for HMGB1-related diseases. As used herein, the term "pharmaceutically acceptable carrier" is intended to include any or all solvents, dispersion media, coatings, isotonizing agents, absorption delaying agents and others, which are physiologically compatible. Examples of a pharmaceutically acceptable carrier include one or more of water, saline, phosphate buffered physiological saline, dextrose, glycerol, ethanol and so on, as well as combinations thereof. When used in the dosage form of injections or the like, the composition preferably comprises a pH adjuster or an isotonizing agent, as exemplified by sugars, polyalcohols (e.g., mannitol, sorbitol), or sodium chloride. Such pharmaceutically acceptable carriers may further comprise minor amounts of auxiliary substances which act to enhance the shelf life or effectiveness of the antibody or antibody portion, as exemplified by a wetting agent, an emulsifying agent, an antiseptic agent, a buffering agent, a stabilizing agent and so on.

The composition of the present invention may be formulated into various dosage forms. Examples of such a composition include liquid, semi-solid or solid dosage forms, such as solutions (e.g., injectable and infusible solutions), dispersions, suspensions, tablets, capsules, troches, pills, powders, liposomes, suppositories, etc. The preferred form will vary depending on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or intravenous injection. In another preferred embodiment, the antibody is administered by intramuscular injection or subcutaneous injection.

The antibody and antibody fragment of the present invention may be incorporated into pharmaceutical compositions suitable for parenteral administration. In the case of using a single type of antibody or antibody portion, it is preferably prepared as an injectable formulation containing 0.1 to 250 mg/mL antibody. On the other hand, in the case of using several types of antibodies in admixture, they are each preferably prepared as an injectable formulation containing 0.001 to 100 mg/mL antibody. It should be noted that the mixing ratio of these several types of antibodies may be determined as appropriate.

Injectable formulations may be configured such that an active ingredient is dissolved in a liquid or lyophilized and then filled into flint or amber vials, ampules or prefilled syringes. The buffering agent used for this purpose may be L-histidine (1 to 50 mM) at pH 5.0 to 7.0 (optimally at pH 6.0), and most suitably 5 to 10 mM of L-histidine. Other suitable buffering agents include, but are not limited to, sodium succinate, sodium citrate, sodium phosphate or potassium phosphate. To change the osmotic pressure of solutions having a concentration of 0 to 300 mM (optimally 150 mM for liquid dosage forms), sodium chloride may be used for this purpose. Lyophilized dosage forms may comprise a cryoprotectant, mainly 0% to 10% (optimally 0.5% to 5.0%) of sucrose. Other suitable cryoprotectants include mannitol, trehalose and lactose. Lyophilized dosage forms may comprise an extender, mainly 1% to 10% (optimally 2% to 4%) of mannitol. For both of liquid and lyophilized dosage forms, a stabilizing agent, mainly 1 to 50 mM (optimally 5 to 10 mM) of L-methionine may be used. Other suitable stabilizing agents include glycine, arginine and Polysorbate 80, etc. In the case of Polysorbate 80, it may be used at a content of 0% to 0.05% (optimally 0.005% to 0.01%). Other surfactants include, but are not limited to, Polysorbate 20 and BRIJ surfactant.

These pharmaceutical compositions should generally be sterile or stable under preparation and storage conditions. These compositions may be formulated as solutions, microemulsions, dispersions, liposomes or other ordered structures suitable for higher drug concentrations. Sterile injectable solutions may be prepared by mixing the required amount of an active compound (i.e., antibody or antibody portion) into an appropriate solvent optionally together with one of the above ingredients or any combination thereof, followed by sterilization through filtration. For preparation of dispersions, an active compound is generally mixed into a sterile vehicle containing a base dispersion medium and other required ingredients selected from among those listed above. In the case of sterile powder formulations required to prepare sterile injectable solutions, preferred procedures for their preparation involve vacuum lyophilization or spray drying of the sterile filtered solution mentioned above, thereby resulting in compositions comprising not only active ingredient powders, but also any other desired ingredients. The adequate fluidity of solutions may be maintained, for example, by using a coating such as lecithin, or by maintaining the required particle size if the solutions are dispersions, or by using a surfactant. Long-lasting absorption of injectable compositions may be accomplished by incorporating an agent for delaying absorption (e.g., monostearate or gelatin) into the compositions.

9. Evaluation Procedures for In Vitro Activity

Biological properties of the antibody or antibody composition may be evaluated by testing the antibody for its ability to suppress the biological activity of HMGB1 in vitro. Techniques for in vitro antibody evaluation include binding assay (e.g., ELISA) and neutralization assay, etc.

1) Binding Activity

As used herein, the phrase "specifically binding" or "specific binding" is intended to mean that the antibody recognizes a given antigen and binds thereto. To measure the binding affinity between antibody and HMGB1, known techniques may be used for this purpose. For example, the measurement may be accomplished by using F protein immobilized on a chip in a protein interaction analyzer such as a Biacore T200® analyzer. The binding affinity ($K_D$ value) is expressed as the ratio between the thus measured Kd (dissociation constant) and Ka (binding constant) ($K_D$=Kd/Ka). Alternatively, human-derived HMGB1 antigen-immobilized immunoplates may be prepared and used for ELISA assay to examine differences in antigen-binding activity.

Among the humanized antibodies of the present invention or antigen-binding fragments thereof, those whose binding activity to human-derived HMGB1 protein (recombinant) (analyzed by ELISA assay) is 1.5-fold or higher, preferably 2-fold or higher, most preferably 2.5-fold or higher than that of the #10-22 chimeric antibody when compared at 250 ng/ml also fall within the present invention. Moreover, when compared with human anti-HMGB1 antibody G4 (WO2007/001422) in the same manner, humanized antibodies or antigen-binding fragments thereof whose activity is 5-fold or higher, preferably 10-fold or higher, more preferably 20-fold or higher than that of G4 also fall within the present invention.

2) Inhibitory Activity Against RAGE Binding

The inhibitory activity of anti-HMGB1 antibody against RAGE binding may be evaluated, for example, by using RAGE-Fc. RAGE-Fc-immobilized immunoplates may be prepared, and a fixed amount of HMGB1 and various concentrations of anti-HMGB1 antibodies (#10-22, EV007156 and G4) may be mixed and incubated to detect the amount of HMGB1 bound to RAGE, whereby these various antibodies can be examined for their activity to inhibit the binding of HMGB1 to RAGE. It should be noted that among the human monoclonal antibodies reported previously, G4 has been shown to have the highest inhibitory activity against RAGE binding (WO2007/001422).

3) Inhibitory Activity Against TNF-α Release in Human PBMCs

The inhibitory activity of anti-HMGB1 antibody against TNF-α release may be evaluated by using human peripheral blood mononuclear cells (PBMCs).

PBMCs may be isolated from human normal subjects and used to examine whether addition of anti-HMGB1 antibody inhibits the released amount of TNF-α observed upon stimulation with HMGB1. In view of the fact that HMGB1-induced in vitro activation of the TLR4 signaling system is also mediated by MD2, CD14 and others, this in vitro evaluation technique using human PBMCs can be regarded as a more significant evaluation system than techniques designed to merely evaluate the inhibitory effect of anti-HMGB1 antibody against binding between TLR4 molecule and HMGB1.

10. Evaluation System for In Vivo Activity

The in vivo activity of anti-HMGB1 antibody may be evaluated in various animal models, one example of which is that the protection effect on sepsis-induced death is evaluated by calculation of survival rate after antibody administration. For preparation of mouse sepsis models, the CLP method (cecal ligation and puncture; Lutterloh et al.) is known, details of which will be given in the Example section.

As used herein, the terms and phrases including "neutralization," "inhibitory effect," "inhibition," "suppression," "capable of inhibiting" and so on are intended to mean that biological activity caused by the antigen (HMGB1) is reduced by about 5% to 100%, preferably 10% to 100%, more preferably 20% to 100%, more preferably 30% to 100%, more preferably 40% to 100%, more preferably 50% to 100%, more preferably 60% to 100%, more preferably 70% to 100%, and even more preferably 80% to 100%.

Humanized antibodies or antigen-binding fragments thereof, whose activity required for 50% inhibition (IC50) of binding of HMGB1 protein to RAGE is 20 µg/mL (about 0.13 µM) or less, preferably, 10 µg/mL (about 67 nM) or less, more preferably 5 µg/mL (about 33 nM), most preferably 4.05 µg/mL (about 27 nM) or less, fall within the present invention. Moreover, humanized antibodies or antigen-binding fragments thereof, whose inhibition rate (%) against binding of HMGB1 protein to RAGE is 40% or more at an antibody concentration of 2 µg/ml, fall within the present invention.

Humanized antibodies or antigen-binding fragments thereof, whose activity required for 50% inhibition (IC50) of HMGB1 protein-stimulated TNF-α release in human PBMCs is 0.05 µg/mL (about 0.33 nM) or less, preferably 0.02 µg/mL (about 0.13 nM) or less, most preferably 0.016 µg/mL (about 0.11 nM) or less, fall within the present invention. Moreover, humanized antibodies or antigen-binding fragments thereof, whose inhibitory effect against TNF-α release upon addition of 0.01 µg/ml antibody is 30% or more, preferably 40% or more, most preferably 42.0% or more, fall within the present invention.

The present invention will be further described in more detail by way of the following examples, which are not intended to limit the scope of the present invention. The procedures used in these examples may be found by reference to Molecular Cloning: A Laboratory Manual (Third Edition) (Sambrook et al., Cold Spring Harbor Laboratory Press, 2001), unless otherwise specified.

EXAMPLES

Example 1

Preparation of Anti-HMGB1 Rat Monoclonal Antibody

How to obtain hybridoma cells producing rat antibody #10-22 against the HMGB1 antigen used in the present patent application is summarized below although it is disclosed in WO2007/049468, US2009/0252739, and FASEB J, 2007 (21) p. 3904, etc.

(a) Immunization of Rats

A commercially available mixture of bovine thymus-derived HMGB1 and HMGB2 (Wako Pure Chemical Industries, Ltd., Japan, code number: 080-070741) was administered together with Freund's complete adjuvant into the hind footpads of rats. After 2 weeks, the rats were confirmed to show increased antibody titers, and after 5 weeks, lymph node cells were then collected aseptically from their swollen iliac bone lymph nodes.

(b) Cell Fusion and Cloning of Anti-HMGB1 Antibody-Producing Cells

The above iliac bone lymph node cells and mouse myeloma SP2/O-Ag14(SP2) cells were fused with each other using polyethylene glycol, and the resulting fused cells were cultured in 96-well microplates and subjected to primary screening by ELISA and secondary screening by Western blotting to thereby clone anti-HMGB1 antibody-producing cells.

Example 2

Cloning of Antibody Genes (a) Antibody Gene Cloning

Total RNA was purified from the #10-22-producing hybridoma cells with a QIAamp RNA Blood Mini Kit (QIAGEN) and then used to synthesize cDNA with Cells-to-cDNA II (Ambion). Further, from the resulting cDNA, the full-length H and L chain antibody genes were amplified by PCR with their respective primers by using 5' RACE (rapid amplification of cDNA ends)-PCR techniques. The amplified #10-22 antibody H and L chain gene fragments were cloned into vectors for expression in eukaryotic cells.

(b) Confirmation of Cloned #10-22 for Antigen-Binding Ability

The H chain- and L chain-encoding plasmids were co-transformed into CHO-K1 cells. Transformation was accomplished by using Lipofectamine LTX and Plus reagent (Invitrogen). After 2 days, the culture supernatant was collected and reacted at room temperature for 1 hour with bovine thymus-derived HMGB1 (Shino-Test Corporation, Japan, #326059683, 100 ng/well) immobilized on an immunoplate (Nunc, Maxisorp), followed by reaction at room temperature for 1 hour with HRP-labeled anti-rat IgG antibody (DAKO, P0450). TMB (3,3',5,5'-tetramethylbenzidine; SureBlue, KPL, #52-00-03) was added to confirm that the antibody in the culture supernatant bound to HMGB1, as determined by absorbance at 450 nm (FIG. 1).

(c) Determination of #10-22 Amino Acid Sequence from Nucleotide Sequence

The H and L chain nucleotide sequences of #10-22 were confirmed with an ABI sequencer. The resulting nucleotide sequences were used to determine the H and L chain amino acid sequences of #10-22. The H and L chain amino acid sequences with signal sequences are shown in SEQ ID NOs: 1 and 2, respectively, while the H and L chain amino acid sequences without signal sequences are shown in SEQ ID NOs: 3 and 4, respectively, and the variable region (VH and VL) amino acid sequences are shown in SEQ ID NOs: 5 and 6, respectively.

Moreover, for analysis of antibody complementarity determining regions (CDRs), "the definition of Kabat" was used (www.bioinf.org.uk: Dr. Andrew C. R. Martin's Group, Antibodies: General Information). However, H chain CDR1 was defined to be a sequence according to both "the definition of Kabat" and "the definition of Chothia" (http://www.bioinf.org.uk/abs/#kabatnum). The H chain CDR1, CDR2 and CDR3 amino acid sequences of #10-22 are shown in SEQ ID NOs: 7, 8 and 9, respectively, while the L chain CDR1, CDR2 and CDR3 amino acid sequences are shown in SEQ ID NOs: 10, 11 and 12, respectively.

Example 3

Preparation of Chimeric Antibody and Humanized Antibody (a) Preparation of #10-22 Chimeric Antibody In order that the rat antibody can be used as an antibody drug, a chimeric antibody and a humanized antibody were prepared by antibody genetic engineering with the aim of reducing the immunogenicity of the rat antibody while maintaining its antigen-binding ability. First, a chimeric antibody was prepared, in which the constant regions of the rat antibody were replaced with human-derived amino acid sequences (IgG1(λ)). The antigen-binding ability of the thus prepared chimeric antibody was detected in the same manner as used for the rat antibody, thus confirming that the antigen-binding ability was maintained (FIG. 2). The H and L chain amino acid sequences of the chimeric antibody are shown in SEQ ID NOs: 13 and 14, respectively.

(b) Humanization of #10-22 Chimeric Antibody L Chain

Figure 4:
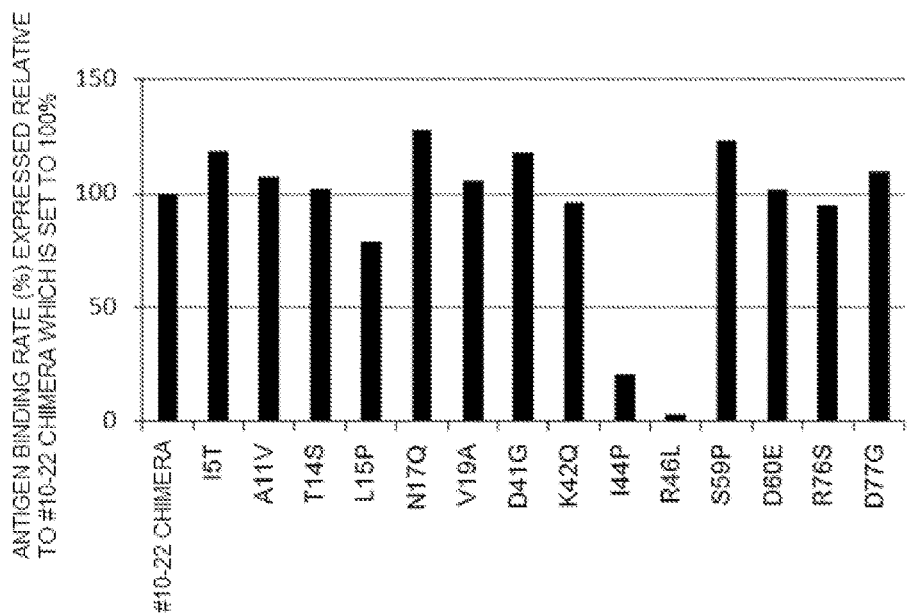
FIG. 4 shows the binding ability to HMGB1 evaluated after #10-22 chimeric antibody L chain site substitution. This evaluation was conducted by ELISA assay using HMGB1-immobilized immunoplates. As a control, #10-22 chimeric antibody was used, and the binding rate to HMGB1 was calculated for #10-22 chimeric antibody L chain site substitution variants (14 types), assuming that the OD value of this control was set to 100%.

For humanization, it is necessary to keep six CDR regions of the #10-22 chimeric antibody (#10-22 VL-CDR1/2/3 and #10-22 VH-CDR1/2/3) and to replace framework regions (FRs) derived from the rat antibody #10-22 with human FRs (FR1, FR2, FR3 and FR4). First, a search was conducted for human FR sequence candidates highly homologous to the #10-22 chimeric antibody L chain FR sequence using V-BASE (http://vbase.mrc-cpe.cam.ac.uk/) and Blast (http://blast.ncbi.nlm.nih.gov) to select 8 types of human-derived L chain variable region sequences (SEQ ID NOs: 15 to 24). An alignment of amino acid sequences was made between these variable regions and the #10-22 chimeric antibody to select "rat amino acid residues" which were not observed in these human FR sequences, thereby determining human amino acid sequences for L chain FRs (Human_VL; SEQ ID NOs: 25 to 28) in which all of these 14 positions (positions 5, 11, 14, 15, 17, 19, 41, 42, 44, 46, 59, 60, 76 and 77) were replaced with consensus sequences of the above 8 human FR sequences (FIG. 3). Secondly, genes were prepared respectively for site-substituted chimeric antibodies (L chain) (I5T, A11V, T14S, L15P, N17Q, V19A, D41G, K42Q, I44P, R46L, S59P, D60E, R76S and D77G) in which 14 sites of rat amino acid residues were replaced one by one. The resulting genes for 14 types of #10-22 chimeric antibody (L chain) site substitution variants were each transformed together with the #10-22 chimeric antibody (H chain) gene into CHO-K1 cells. The thus prepared 14 types of antibodies were quantified by ELISA assay using anti-IgG antibody-immobilized immunoplates, adjusted to an equal antibody concentration and then tested for antigen-binding ability. Among these site substitution variants, two site substitution variants I44P and R46L within the L chain variable region were each found to have significantly reduced antigen-binding ability when compared to the chimeric antibody (FIG. 4). It should be noted that the positions of substitution sites were expressed in accordance with the numbering system of Kabat.

Figure 5:
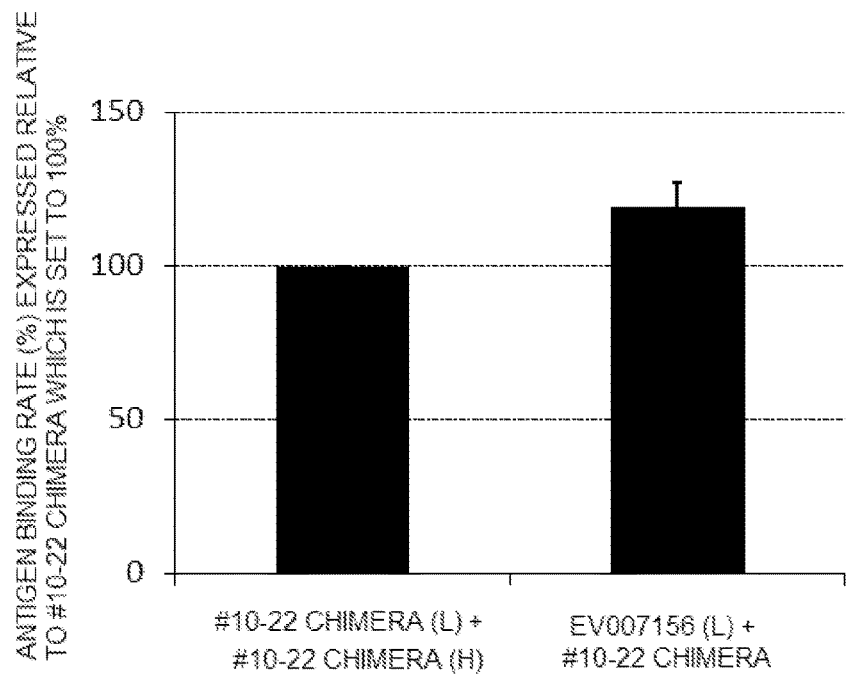
FIG. 5 shows the antibody binding ability to HMGB1 evaluated after #10-22 chimeric antibody L chain humanization. This evaluation was conducted by ELISA assay using HMGB1-immobilized immunoplates. As a control, #10-22 chimeric antibody was used, and the binding rate to HMGB1 was calculated for an antibody obtained by co-expression of #10-22 (L chain) humanized antibody (EV007156L) and #10-22 chimeric antibody (H chain), assuming that the OD value of this control was set to 100%.

In the #10-11 chimeric antibody L chain, the original amino acid sequences derived from the rat antibody L chain variable region were kept for positions 44 and 46 and three CDR sequences, while the other amino acid sequences in the variable region were all replaced with amino acid sequences from the above Human_VL to thereby prepare a humanized antibody (L chain) gene encoding such a recombinant L chain. The resulting #10-22 humanized antibody (L chain) (hereinafter referred to as EV007156L) gene and the #10-22 chimeric antibody (H chain) gene were co-transformed into CHO-K1 cells. The thus prepared antibody was quantified by ELISA assay using anti-IgG antibody-immobilized immunoplates, adjusted to an equal antibody concentration and then tested for antigen-binding ability. This antibody was found to have equal or slightly increased antigen-binding ability when compared to the chimeric antibody (FIG. 5).

(c) Humanization of #10-22 Chimeric Antibody H Chain

Figure 6:
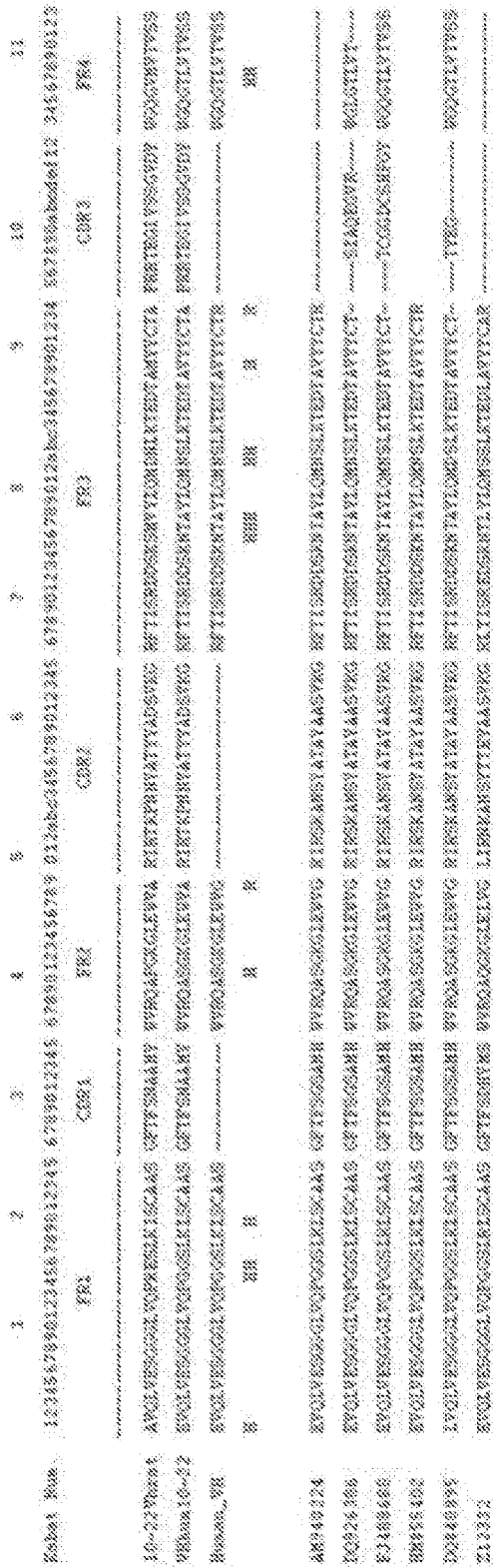
FIG. 6 shows the amino acid sequences of the H chain variable region of rat antibody #10-22 and its humanized antibody (VHhum10-22), along with human FR (Human_VH), and also shows the amino acid sequences of 6 human-derived antibody or germline (GenBank Accession Nos.: AM940224, DQ926386, FJ488688, HM855402, DQ840895 and Z12332) H chain variable regions highly homologous to the H chain FR sequence of #10-22. In this figure, Human_VH is a FR sequence modified to substitute consensus sequences in the above 6 human FR sequences for all 15 positions of the rat antibody #10-22 FR sequence at which amino acid residues not observed in the above 6 human-derived sequences, i.e., "rat amino acid residues" are located (these positions are indicated with the symbol "H: human" or "R: rat" under the Human VH sequence in the figure). In this figure, VHhum10-22 represents the H chain variable region of humanized antibody (EV007156), and its FR amino acid residues other than those at positions 49 and 94 are the same as in the above Human_VH sequence. It should be noted that the positions of amino acid residues in this figure are expressed in accordance with the numbering system of Kabat (http://vbase.mrc-cpe.cam.ac.uk/).
Figure 7:
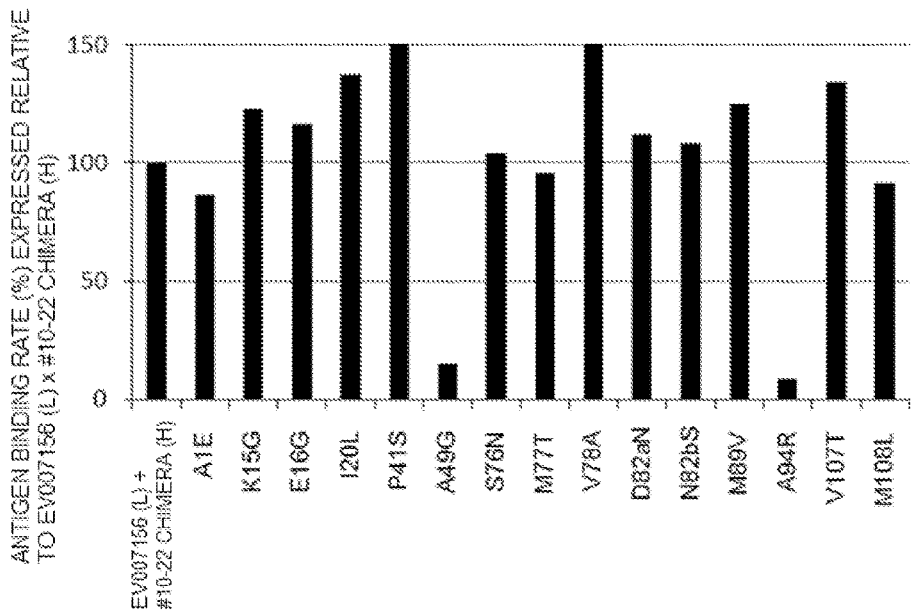
FIG. 7 shows the binding ability to HMGB1 evaluated after #10-22 chimeric antibody H chain site substitution. This evaluation was conducted by ELISA assay using HMGB1-immobilized immunoplates. As a control, the H chain of #10-22 chimeric antibody was used, and the binding rate to HMGB1 was calculated for #10-22 chimeric antibody H chain site substitution variants (15 types), assuming that the OD value of this control was set to 100%.

In the same manner as used for the L chain, a search was conducted for human FR sequence candidates highly homologous to the #10-22 chimeric antibody H chain FR sequence to select 6 types of human-derived H chain sequences (SEQ ID NOs: 29 to 34). An alignment of amino acid sequences was made between these variable regions and the rat antibody #10-22-derived H chain variable region (FIG. 6) to select 15 "rat amino acid residues" which were not observed in these human FR sequences (at positions 1, 15, 16, 20, 41, 49, 76, 77, 78, 82a, 82b, 89, 94, 107 and 108), thereby determining human amino acid sequences for H chain FRs (Human_VH; SEQ ID NOs: 35 to 38) in which all of these 15 positions were replaced with consensus sequences of the above 6 human FR sequences (FIG. 6). Secondly, for the above chimeric antibody H chain, genes were prepared respectively for site-substituted chimeric antibodies (H chain) (A1E, K15G, E16G, I20L, P41S, A49G, S76N, M77T, V78A, D82aN, N82bS, M89V, A94R, V107T and M108L) in which 15 sites of non-human amino acid residues on the FR sequence were replaced one by one. The resulting genes for 15 types of #10-22 chimeric antibody (H chain) site substitution variants were each transformed together with the EV007156L gene into CHO-K1 cells. The thus prepared 15 types of antibodies were quantified by ELISA assay using anti-IgG antibody-immobilized immunoplates, adjusted to an equal antibody concentration and then tested for antigen-binding ability. Among these site-substituted antibodies, two site substitution variants A49G and A94R within the H chain variable region were each found to have significantly reduced antigen-binding ability when compared to the antibody obtained by co-expression of the chimeric antibody (H chain) gene and the EV007156L gene (FIG. 7).

Figure 8:
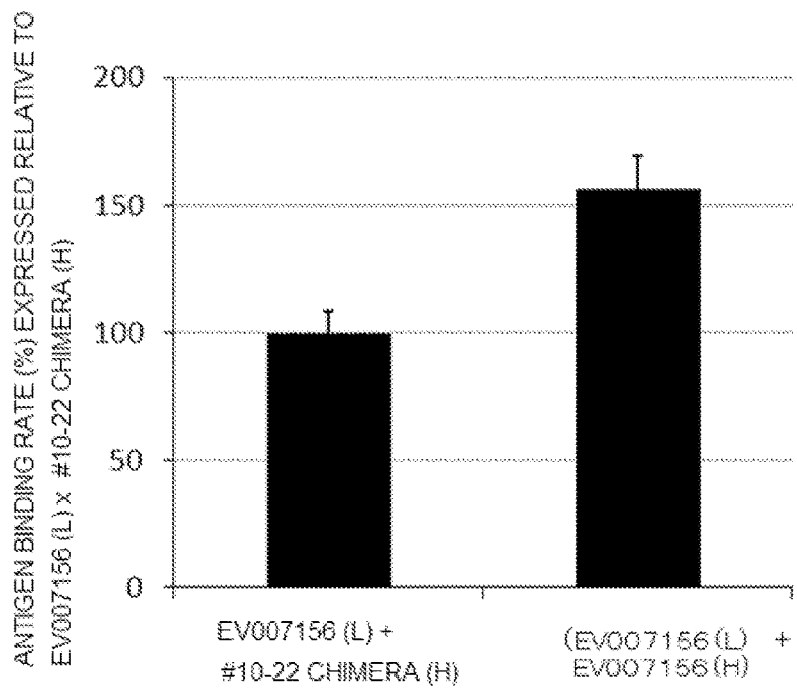
FIG. 8 shows the binding ability to HMGB1 evaluated after #10-22 chimeric antibody humanization. This evaluation was conducted by ELISA assay using HMGB1-immobilized immunoplates. As a control, the H chain of #10-22 chimeric antibody was used, and the binding rate to HMGB1 was calculated for #10-22 humanized antibody (EV007156), assuming that the OD value of this control was set to 100%.

In the #10-11 chimeric antibody H chain, the original amino acid sequences derived from the rat antibody H chain variable region were kept for positions 49 and 94 and three CDR sequences, while the other amino acid sequences in the H variable region were all replaced with amino acid sequences from the above Human_VH to thereby prepare a humanized antibody (H chain) gene encoding such a recombinant H chain. The resulting #10-22 humanized antibody (H chain) (hereinafter referred to as EV007156H) gene and the EV007156L gene were co-transformed into CHO-K1 cells. The thus prepared antibody was quantified by ELISA assay using anti-IgG antibody-immobilized immunoplates, adjusted to an equal antibody concentration and then tested for antigen-binding ability. This antibody was found to have significantly increased antigen-binding ability when compared to the antibody obtained by co-expression of the #10-22 chimeric antibody (H chain) gene and the EV007156L gene (FIG. 8). The full-length H and L chain amino acid sequences of the #10-22 humanized antibody (hereinafter referred to as EV007156) are shown in SEQ ID NOs: 39 and 40, respectively, and their variable region amino acid sequences are shown in SEQ ID NOs: 41 and 42, respectively. Likewise, the amino acid sequences of H chain variable region FR1, FR2, FR3 and FR4 are shown in SEQ ID NOs: 43, 44, 45 and 46, respectively, while the amino acid sequences of L chain variable region FR1, FR2, FR3 and FR4 are shown in SEQ ID NOs: 47, 48, 49 and 50, respectively.

To evaluate the #10-22 chimeric antibody and EV007156 for their binding activity to HMGB1 (analyzed by ELISA assay), bovine thymus-derived HMGB1 was immobilized overnight at 4° C. on immunoplates (Nunc, Maxisorp) at a concentration of 25 ng/well and N101 (NOF Corporation, Japan) was added thereto to block the plates for 2 hours, followed by reaction at room temperature for 1 hour with dilution samples (prepared at 7 concentrations) of the #10-22 chimeric antibody or EV007156 diluted 4-fold starting from 4 μg/ml as a primary antibody. Subsequently, HRP-labeled anti-human IgGγ antibody (MBL, #208) was reacted at room temperature for 1 hour. After addition of TMB, detection was accomplished by absorbance at 450 nm. As a result, the humanized antibody EV007156 at an antibody concentration of 250 ng/ml was found to have about 5-fold higher antigen-binding ability than the #10-22 chimeric antibody.

Example 4

Binding Ability to Various HMGB1s (a) Preparation of Various HMGB1s
(a-1) Bovine Thymus-Derived HMGB1
Bovine thymus-derived HMGB1 was available from Shino-Test Corporation, Japan, or Chondrex.
(a-2) Human-Derived Recombinant HMGB1 (Expressed in Sf9 Cells)

Human-derived recombinant HMGB1 was purified in the form of being N-terminally His-tagged from baculovirus-infected Sf9 cells. Namely, Sf9 cells were infected with HMGB1-expressing baculovirus and then cultured for 72 hours under rotary conditions, followed by centrifugation to obtain a cell pellet. Then, the cells were suspended in a buffer containing protease inhibitors and sonicated (1 minute, repeated four times) to homogenize the cells. Subsequently, the cell homogenate was centrifuged at 15,000 rpm for 15 minutes to collect the HMGB1-containing supernatant. HMGB1 contained in the supernatant was purified by being adsorbed to QIAGEN Ni-NTA, eluted with 100 mM imidazole and dialyzed against phosphate buffer (PBS(−)).
(a-3) Nuclear HMGB1
Nuclear HMGB1 was prepared from CHO-K1 cells cultured in 10% FCS-DMEM. Namely, CHO-K1 cells were cultured under conditions of 10% FCS-DMEM, 5% $CO_2$ and 37° C., and when the cell density reached confluency, the CHO-K1 cells were washed twice with PBS(−), scraped off with a cell scraper (Nunc, #179693) and then collected into centrifugal tubes. To the cell suspension, TritonX-100 was added at a concentration of 0.2%, followed by sonication to disrupt the cells. The resulting solution was used as a nuclear antigen.
(a-4) Necrotic HMGB1
Necrotic HMGB1 was prepared from CHO-K1 cells cultured in 10% FCS-DMEM. Namely, CHO-K1 cells were cultured under conditions of 10% FCS-DMEM, 5% $CO_2$ and 37° C., and when the cell density reached confluency, the cells were washed twice by addition of PBS(−). Then, after ultrapure water was added in an appropriate amount, the cells were scraped off with a cell scraper. Freezing and thawing were repeated five times by using a thermostatic vessel and dry ice to disrupt the cells, followed by centrifugation at 12,000 rpm for 10 minutes to remove cell debris. The supernatant was stored at −80° C. for use as necrotic HMGB1.
(a-5) Apoptotic HMGB1
Apoptotic HMGB1 was prepared from CHO-K1 cells cultured in 10% FCS-DMEM. CHO-K1 cells were cultured under conditions of 10% FCS-DMEM, 5% $CO_2$ and 37° C., and when the cell density reached confluency, the CHO-K1 cells were irradiated with UV for 2 minutes, followed by replacement with serum-free DMEM medium. After being cultured for 16 hours, the medium was collected and centrifuged to remove the cells, and the resulting supernatant was used as apoptotic HMGB1.
(a-6) Secondary Necrotic HMGB1
Secondary necrotic HMGB1 was prepared from CHO-K1 cells cultured in 10% FCS-DMEM. CHO-K1 cells were cultured under conditions of 10% FCS-DMEM, 5% $CO_2$ and 37° C., and when the cell density reached confluency, the CHO-K1 cells were irradiated with UV for 2 minutes, followed by replacement with serum-free DMEM medium. After being cultured for 48 hours, the medium was collected and centrifuged to remove the cells, and the resulting supernatant was used as secondary necrotic HMGB1.
(a-7) Activated HMGB1
Activated HMGB1 was prepared from RAW cells (RIKEN) cultured in 10% FCS-RPMI. RAW cells were cultured under conditions of 10% FCS-RPMI, 5% $CO_2$ and 37° C., and when the cell density reached confluency, the RAW cells were washed twice with PBS(−), followed by replacement with serum-free RPMI medium and the subsequent stimulation with 1 μg/ml PolyIC. At 24 hours after stimulation, the culture supernatant was collected and centrifuged to remove the cells, and the resulting supernatant was used as activated HMGB1.

(b) Binding Ability of EV007156 to Various HMGB1s, as Analyzed by Western Blotting

10-22 and its humanized antibody (EV007156), and S6 (MedImmune) and G4 (MedImmune) antibodies were tested by Western blotting for their binding ability to various HMGB1s prepared as above. Namely, bovine thymus-derived HMGB1, Sf6-expressed recombinant human HMGB1, nuclear HMGB1, necrotic HMGB1, apoptotic HMGB1, secondary necrotic HMGB1 and activated HMGB1 were each mixed with 5×SDS sample buffer and boiled at 95° C. for 5 minutes. Serial dilutions of each HMGB1 sample were electrophoresed on a 12% polyacrylamide gel and the proteins were then transferred onto a PVDF membrane. After blocking with 5% skimmed milk-TBST for 2 hours, #10-22, EV007156, S6 and G4 (2 μg/ml each) were reacted at room temperature for 1 hour. Subsequently, HRP-labeled secondary antibody was reacted at room temperature for 1 hour, and detection was accomplished by using ECL prime (GE Healthcare, RPN2232) (Table 4). For use in testing as positive control antibodies, the human anti-HMGB1 antibodies (S6 and G4) described in WO2007/001422 were obtained by synthesis of genes encoding the amino acid sequences disclosed in this patent, and the subsequent antibody production and purification.

[Table 4]

TABLE 4

Evaluation of antibody binding ability to various antigens (Western blotting)

| Antigen type | Anti-HMGB1 antibody | | | |
|---|---|---|---|---|
| | #10-22 | EV007156 | S6 | G4 |
| Bovine Thymus | ++ | ++ | ++ | ++ |
| Recombinant | ++ | ++ | + | + |
| Nuclear | ++ | ++ | − | + |
| Necrotic | ++ | ++ | + | ++ |
| Apoptotic | ++ | + | − | ++ |
| Secondary Necrotic | + | + | − | − |
| Activated | ++ | ++ | − | ++ |

Evaluation of HMGB1 antibodies (#10-22, EV007156, S6 and G4) for their binding ability to various HMGB1s (bovine thymus, recombinant, nuclear, necrotic, apoptotic, secondary necrotic and activated HMGB1s).
−: no binding,
+: weak binding,
++: strong binding (c) Antigen-Binding ELISA on #10-22 Chimeric Antibody and EV007156

Figure 9:
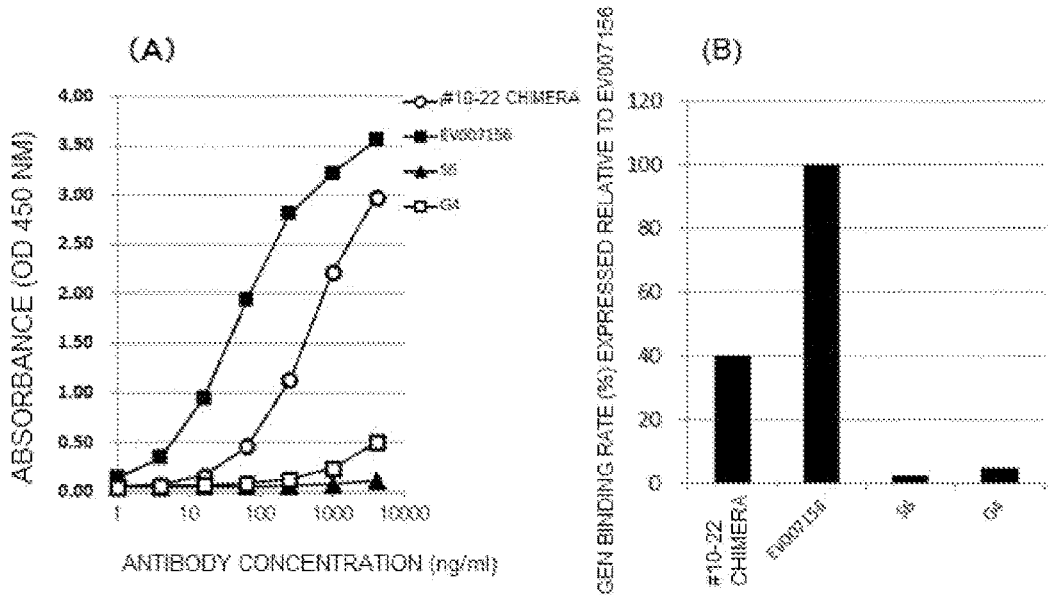
FIG. 9 shows the binding ability to recombinant HMGB1 (derived from Sf9 cells) evaluated for anti-HMGB1 antibodies (#10-22 chimeric antibody, EV007156, S6 and G4). This evaluation was conducted by ELISA assay using HMGB1-immobilized immunoplates (A). The binding ability to each HMGB1 (derived from bovine thymus or Sf9 cells) was calculated for each HMGB1 antibody at an antibody concentration of 250 ng/ml, based on the OD value of EV007156 (B). Open circles: #10-22 chimera, solid squares: EV007156, solid triangles: S6, and open squares: G4.

The above human-derived recombinant HMGB1 was immobilized overnight at 4° C. on immunoplates (Nunc, Maxisorp) at a concentration of 25 ng/well and N101 (NOF Corporation, Japan) was added thereto to block the plates for 2 hours, followed by reaction at room temperature for 1 hour with dilution samples (prepared at 7 concentrations) of the #10-22 chimeric antibody, EV007156, S6 or G4 diluted 4-fold starting from 4 μg/ml as a primary antibody. Subsequently, HRP-labeled anti-human IgGγ antibody (MBL, #208) was reacted at room temperature for 1 hour. After addition of TMB, detection was accomplished by absorbance at 450 nm (FIG. 9(A)). In addition, FIG. 9(B) shows the binding rate of each HMGB1 antibody to each HMGB1 (recombinant) at an antibody concentration of 250 ng/ml. The humanized antibody EV007156 was found to have about 2.5-fold higher antigen-binding ability to recombinant HMGB1 than the #10-22 chimeric antibody. Moreover, EV007156 was found to have 45-fold and 22-fold higher binding ability to recombinant HMGB1 than S6 and G4, respectively.

Example 5

Binding Inhibition Assay

RAGE Binding Inhibition Assay

Figure 10:
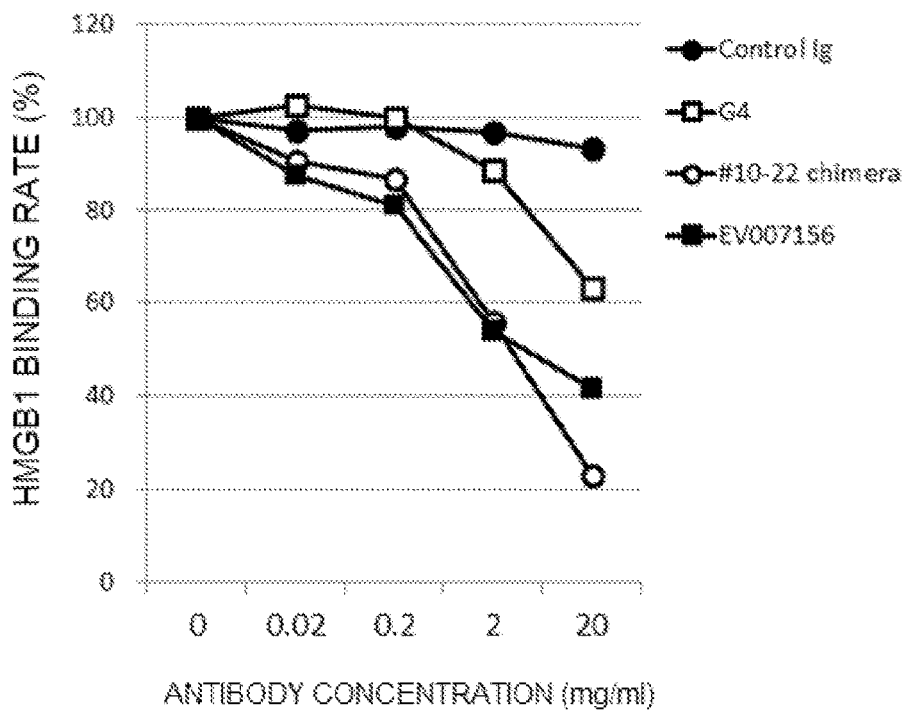
FIG. 10 shows the inhibitory effect of anti-HMGB1 antibodies on binding to RAGE. After the amount of HMGB1 was quantified from the OD value obtained by ELISA, the binding rate of HMGB1 to RAGE was calculated assuming that the amount of HMGB1 used for the binding inhibition assay (2 μg/ml) was set to 100%. Open circles: #10-22 chimera, solid squares: EV007156, open squares: G4, and solid circles: Control Ig.

RAGE-Fc (R&D, 250 ng/well) was immobilized overnight at 4° C. on immunoplates (Nunc, Maxisorp) and 5% BSA (bovine serum albumin) was added thereto to block the plates for 2 hours, followed by addition of human monoclonal antibody (Control Ig) to block the plates for 2 hours. HMGB1 (Sf6-derived recombinant HMGB1, final concentration: 2 μg/ml) was mixed with anti-HMGB1 antibody (#10-22 chimera, EV007156 or G4) or non-HMGB1-specific human monoclonal antibody (Control Ig) serving as a negative control antibody at a final concentration of 0, 0.02, 0.2, 2 or 20 μg/ml and incubated for 60 minutes. Subsequently, the reaction solutions were added to the immunoplates and reacted for 2 hours. Then, anti-HMGB1 antibody (Abnova, #H00003146-M08, 1 μg/ml) which had been biotinylated with a Biotin Labeling Kit (Dojindo, LK03) was reacted at room temperature for 1 hour. Finally, HRP-labeled streptavidin was reacted at room temperature for 1 hour. TMB (3,3',5,5'-tetramethylbenzidine; SureBlue, KPL, #52-00-03) was added and HMGB1 bound to RAGE was detected by absorbance at 450 nm (FIG. 10). #10-22 chimera, EV007156 and G4 were all found to inhibit the binding of HMGB1 to RAGE in a manner dependent on the added antibody concentration. Moreover, the inhibitory effect upon addition of 2 μg/ml antibody was 44.0% for #10-22 chimera and 46.2% for EV007156, but 1.4% for G4. Likewise, upon addition of 20 μg/ml antibody, the inhibitory effect was 77.0% for #10-22 chimera and 58.6% for EV007156, but 36.9% for G4. Moreover, the 50% inhibitory concentration (IC50) was 3.04 μg/ml (20.3 nM) for #10-22 chimera, 4.05 μg/ml (27 nM) for EV007156, and 20 μg/ml (130 nM) or higher for G4. Thus, #10-22 chimera and EV007156 were found to have a significantly stronger inhibitory effect than G4 against HMGB1 binding to RAGE.

Example 6

TNF-Alpha Release Inhibition Assay

Figure 11:
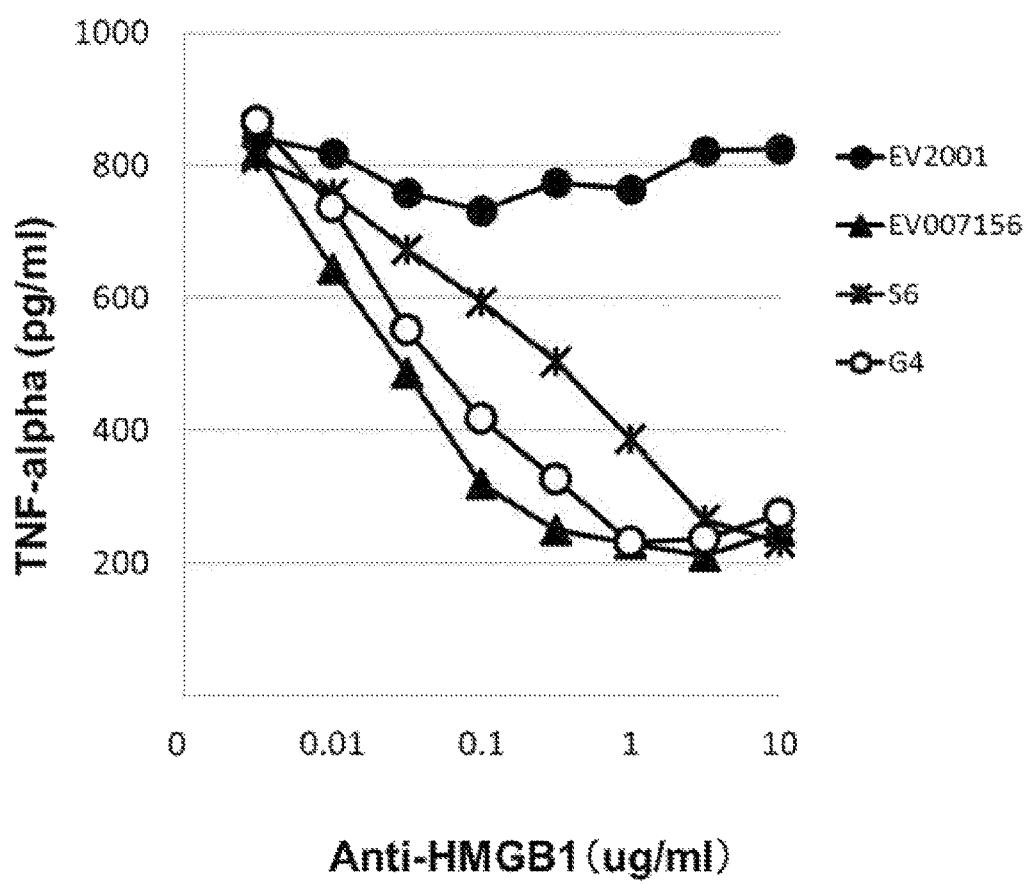
FIG. 11 shows the inhibitory effect of anti-HMGB1 antibodies on HMGB1-induced TNF-alpha release activity in PBMCs. PBMCs obtained from peripheral blood were stimulated with HMGB1, and the amount of TNF-alpha contained in the culture supernatant obtained after 24 hours was quantified (eBioscience, Human TNF-alpha Ready-Set-Go!). Solid circles: negative control (EV2001), solid triangles: EV007156, asterisks: S6, and open circles: G4.

Peripheral blood mononuclear cells (PBMCs) were isolated from human normal subjects and used to examine whether addition of EV007156 would inhibit the released amount of TNF-alpha observed upon stimulation with HMGB1. First, human peripheral blood was centrifuged (1,400 rpm, 30 minutes) using Histopaque (SIGMA, #10771) to separate and collect PBMCs. Secondly, the resulting PBMCs were seeded in 96-well multiplates (BD, #353072) at 2×10$^5$ cells/well in Opti-MEM (Gibco), followed by addition of a mixture pre-incubated at 37° C. for 30 minutes containing bovine thymus-derived HMGB1 (Chondrex, final concentration: 1 μg/ml) and anti-HMGB1 antibody (EV007156, S6 or G4) or non-HMGB1-specific human monoclonal antibody serving as a negative control antibody (final concentration: serial dilution starting from 10 μg/ml). After being cultured for 24 hours, the culture supernatants were collected and quantified for TNF-alpha using Human TNF-alpha ELISA Ready-SET-Go! (eBioscience, #88-7346) (FIG. 11). Moreover, the inhibitory effect upon addition of 0.01 μg/ml antibody was 42.0% for EV007156, but 21.3% for S6 and 25.5% for G4. Likewise, upon addition of 0.1 μg/ml antibody, the inhibitory effect was 75.9% for EV007156, but 49.4% for S6 and 68.5% for G4. Moreover, the 50% inhibitory concentration (IC50) was 0.016 μg/ml (0.106 nM) for EV007156, but 0.106 μg/ml (0.706 nM) for S6 and 0.026 μg/ml (0.173 nM) or higher for G4. In view of the foregoing, EV007156 was found to have a significantly stronger inhibitory effect than S6 and G4 against TNF-alpha release.

These findings indicate that the humanized antibody EV007156 of the present invention has a substantially higher inhibitory effect against HMGB1-induced activation of TLR-4 receptor-mediated signaling in macrophages and monocyte cells.

Example 7

Affinity Measurement

A Biacore T200 analyzer designed to detect binding interaction between biomolecules by surface plasmon resonance was used to measure the affinity of antibody to HMGB1. First, a sensor chip (CMS) was adsorbed with EV007156, S6 or G4 as a ligand at a concentration of 0.5 μg/ml. Secondly, recombinant HMGB1 adjusted by 2-fold serial dilution starting from 10 nM was passed as an analyte over the sensor chip to measure binding affinity. The results obtained indicated that the $K_D$ (M) value of each antibody was $3.29 \times 10^{-10}$ M for EV007156, and $2.67 \times 10^{-10}$ M and $6.79 \times 10^{-10}$ M for S6 and G4, respectively (Table 5).

TABLE 5

| Antibody name | $k_a$ (1/Ms) | $k_d$ (1/s) | $K_D$ (M) |
|---|---|---|---|
| EV007156 | $7.11 \times 10^6$ | $2.34 \times 10^{-3}$ | $3.29 \times 10^{-10}$ |
| S6 | $4.11 \times 10^6$ | $1.18 \times 10^{-3}$ | $2.67 \times 10^{-10}$ |
| G4 | $3.32 \times 10^6$ | $2.26 \times 10^{-3}$ | $6.79 \times 10^{-10}$ |

Example 8

Pharmacokinetic Testing

Figure 12:
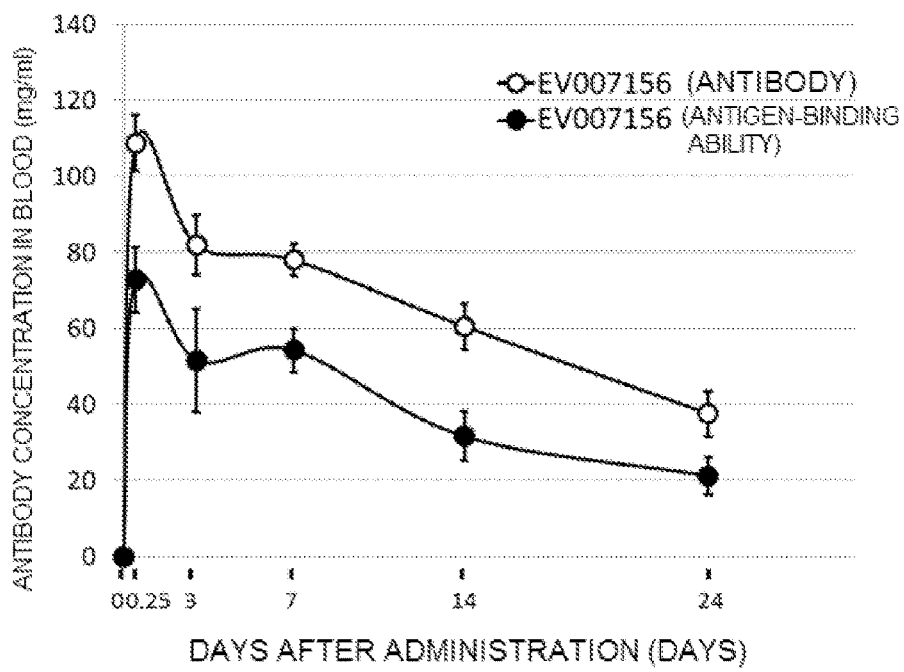
FIG. 12 shows the results of pharmacokinetic testing in the mouse body with the use of EV007156. EV007156 was intraperitoneally administered to C57BL/6N mice at a dose of 10 mg/kg, and blood samples collected at 0.25, 3, 7, 14 and 24 days after administration were quantified for EV007156 contained therein by ELISA. Open circles: EV007156 quantified with immobilized anti-human IgG, and solid circles: EV007156 quantified with immobilized HMGB1.

C57BL/6N mice (female) at 8 weeks of age were intraperitoneally administered with EV007156 at a dose of 10 mg/kg, and their blood was collected at 6 hours (0.25 days), 3 days, 7 days, 14 days and 24 days after administration. Each blood sample was centrifuged at 3,500 rpm for 10 minutes to separate serum, and the resulting serum was reacted for 1 hour with an immunoplate (Nunc, Maxisorp) on which anti-human IgG antibody had been immobilized overnight at a concentration of 250 ng/well. Subsequently, HRP-labeled anti-human IgG antibody (MBL, #208) was reacted for 1 hour. After addition of TMB (3,3',5,5'-tetramethylbenzidine; SureBlue, KPL, #52-00-03), the antibody concentration was quantified by absorbance at 450 nm. Moreover, to confirm the binding ability of EV007156 to the antigen, an immunoplate (Nunc, Maxisorp) on which recombinant HMGB1 had been immobilized overnight at a concentration of 25 ng/well was used for detection in accordance with the same procedures as used for antibody quantification. The results obtained are shown in FIG. 12. The antibody concentration in blood already began to increase from 6 hours after antibody administration and was stabilized at 80 μg/ml until 3 days after administration. Then, the antibody concentration gradually decreased over 24 days after administration and finally reached 40 μg/ml. The half-life of EV007156 administered in the mouse body was calculated to be 22.8 days. With regard to the antigen-binding ability per antibody, there was no reduction in the antigen-binding ability relative to the amount of antibody during the period from 3 days until 24 days after administration. This result indicated that even after 24 days in the mouse body, EV007156 had antigen-binding ability commensurate with the amount of antibody and retained its stability as an antibody.

Example 9

Epitope Mapping (a) Preparation of Deletion Constructs

Prior to the preparation of deletion constructs, human-derived HMGB1 gene was cloned from HEK293 cells. Namely, RT-PCR was performed on HEK293 cells using Cells to cDNA II (ambion, #AM1723), and the amplified PCR fragment with a histidine tag added at the N-terminal end was then cloned into a pcDNA3.1(+) vector. The resulting gene sequence was confirmed to be a gene for human HMGB1 with a sequencer (ABI, 3130 Genetic Analyzer).

Figure 13:
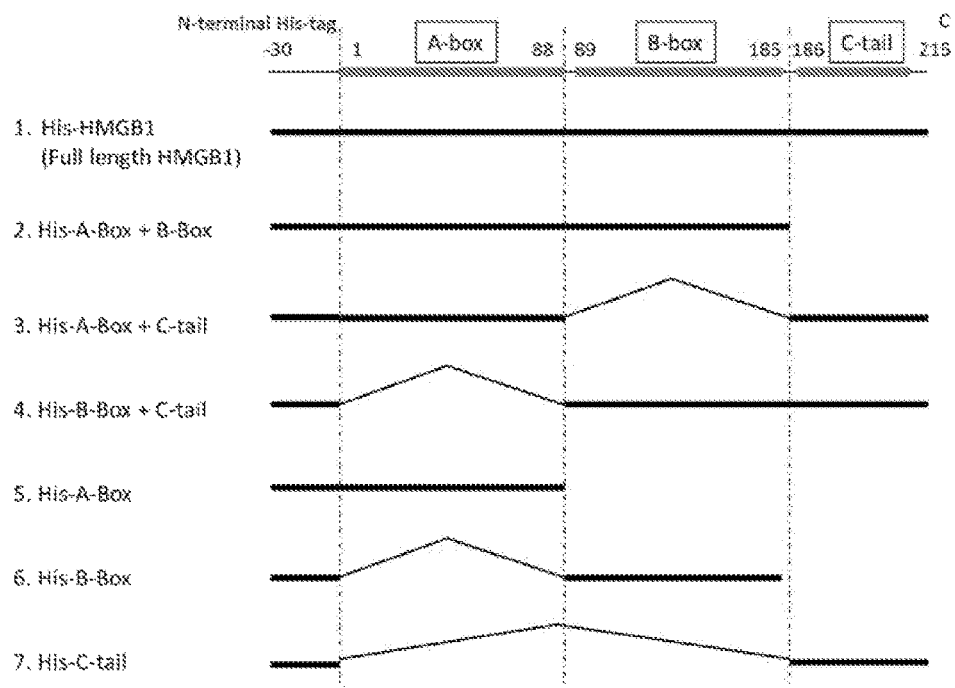
FIG. 13 shows HMGB1 domains and the prepared deletion constructs. The range of amino acids for each domain is as follows: −30 to 0: His tag and linker, 1 to 88: A-Box, 89 to 185: B-Box, and 186 to 125: C-tail (each numeral represents the number of amino acids counted from methionine). This figure shows constituent domains for each of His-tagged full-length HMGB1 and six deletion constructs.
Figure 14:
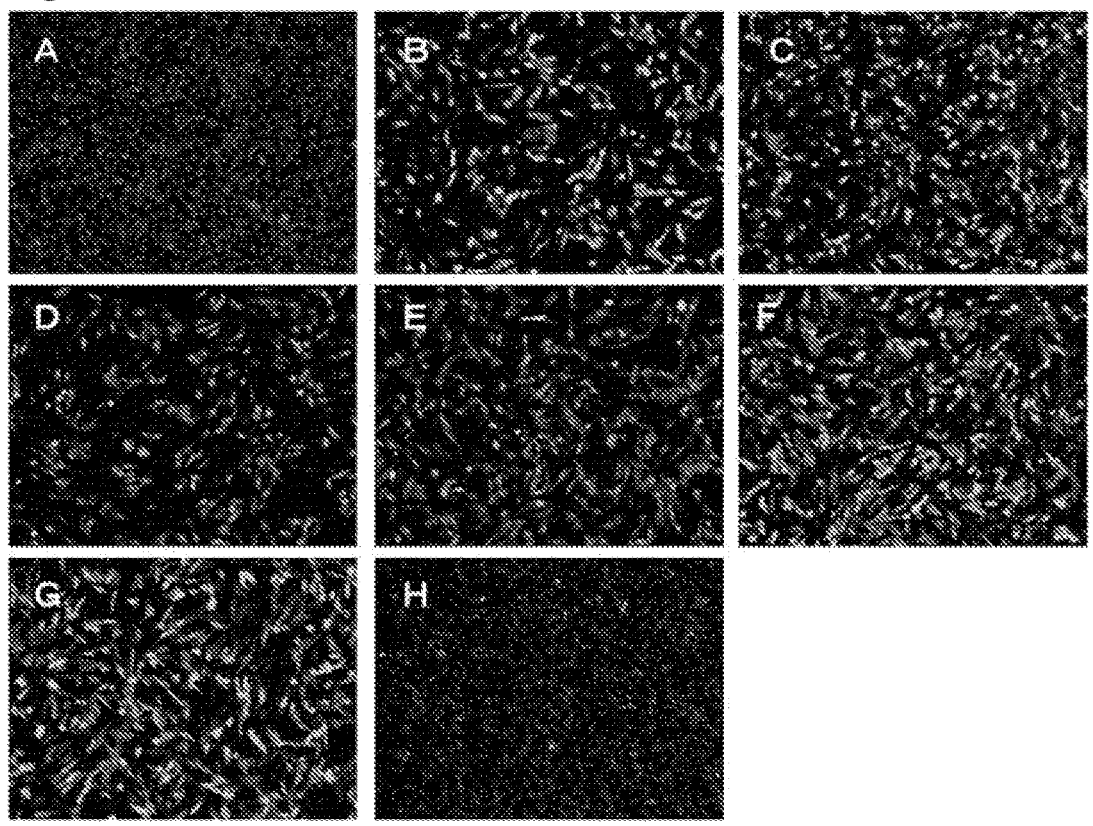
FIG. 14 shows the results of expression confirmation test on the prepared deletion constructs with the use of anti-His antibody. His-tagged full-length HMGB1 and six deletion constructs were each transfected into CHO-K1 cells, followed by staining with anti-His antibody to confirm the expression of each deletion construct. A: CHO-K1, B: His-HMGB1 (full length), C: A-Box+B-Box, D: A-Box+C-tail, E: B-Box+C-tail, F: A-Box, G: B-Box, and H: +C-tail.
Figure 15:
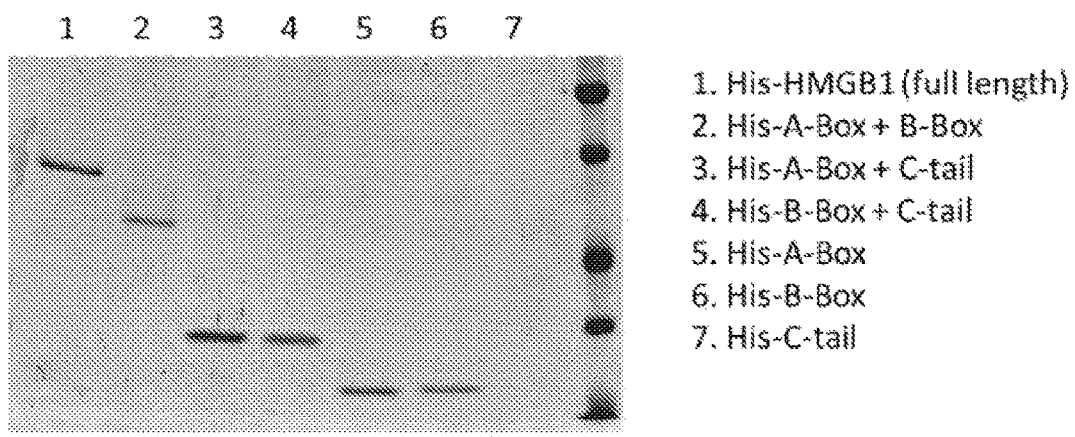
FIG. 15 shows the results of expression confirmation test on the prepared deletion constructs by CBB staining. His-tagged full-length HMGB1 and six deletion constructs were each transfected into CHO-K1 cells. After preparation of cell lysates, the expressed proteins were purified using Ni-sepharose. The individual proteins were electrophoresed on a polyacrylamide gel and stained with CBB.

Subsequently, to determine the epitope of EV007156, HMGB1 was divided into three regions, i.e., A-BOX, B-BOX and C-tail, and six types of deletion constructs were prepared in total (full-length HMGB1, A-Box+B-Box, A-Box+C-tail, B-Box+C-tail, A-Box, B-Box, and C-tail) (FIG. 13). The deletion constructs were each confirmed for their expression by immunofluorescence staining and CBB staining. For confirmation by immunofluorescence staining, plasmids expressing the respective fragments (7 types in total, including full-length HMGB1) were each transfected into CHO-K1 cells using Lipofectamine LTX (Invitrogen). After 24 hours, the cells were fixed with 4% paraformaldehyde and then reacted for 1 hour with anti-His antibody (MBL, PM032) at a concentration of 1 μg/ml. Subsequently, Alexa 488 anti-rabbit IgG antibody (Invitrogen, A11070) was reacted for 1 hour at a concentration of 1 μg/ml, and fluorescence signals were observed under an epifluorescence microscope (FIG. 14). On the other hand, for confirmation by CBB staining, to the cells at 24 hours after transfection, Lysis buffer (PBS, 0.2% TritonX-100, 1 mM EDTA) was added to lyse the cells. The deletion constructs contained in the cell lysates were purified with Ni-sepharose 6B (GE Healthcare). The samples eluted with an eluent (50 mM Tris-HCl (pH 8.0), 500 mM NaCl, 500 mM imidazole) were each added to 5×SDS sample buffer and boiled at 95° C. for 5 minutes. Each sample was electrophoresed on a 12% polyacrylamide gel and then stained with CBB to confirm the expression of each deletion construct (FIG. 15). As a result, all deletion constructs except for C-tail were confirmed for their expression in both cases of immunofluorescence staining and CBB staining.

(b) Detection of Epitope Region by Immunofluorescence Staining

Plasmids expressing the respective fragments (7 types in total, including full-length HMGB1) were each transfected into CHO-K1 cells using Lipofectamine LTX (Invitrogen). After 24 hours, the cells were fixed with 4% paraformaldehyde and then reacted for 1 hour with EV007156 (1 μg/ml). Subsequently, Alexa 488 anti-human IgG antibody was reacted for 1 hour at a concentration of 1 μg/ml, and fluorescence signals were observed under an epifluorescence microscope (FIG. 16). EV007156 was found to be reactive not only with full-length HMGB1, but also with A-Box+C-tail and B-Box+C-tail, i.e., the constructs containing the C-terminal end. Based on this result, it was determined that the epitope of EV007156 would be probably located in the C-terminal region of HMGB1. Then, the same experiment was also performed on S6 and G4. The results indicated that S6 (FIG. 16-b) and G4 (FIG. 16-c) were both reactive with the constructs containing B-Box. Their results were different from the staining pattern of EV007156.

(c) Detection of Epitope Region by Western Blotting

Plasmids expressing the respective fragments were each transfected into CHO-K1 cells using Lipofectamine LTX (Invitrogen). After 24 hours, to the cells, Lysis buffer (PBS, 0.2% TritonX-100, 1 mM EDTA) was added to lyse the cells. Subsequently, 5×SDS sample buffer was added to the cell lysates, followed by boiling at 95° C. for 5 minutes. The respective samples were electrophoresed on a 12% polyacrylamide gel and the proteins were then transferred onto a PVDF membrane at 100 mA for 1 hour. The transferred PVDF membrane was blocked with 5% skimmed milk-TBST for 2 hours and then reacted at room temperature for 1 hour with EV007156 (1 µg/ml). Subsequently, HRP-labeled anti-human IgG (MBL, #208) was reacted at room temperature for 1 hour as a secondary antibody. EV007156 was detected using ECL prime (GE Healthcare, RPN2232) (FIG. 17). The results indicated that EV007156 was reactive not only with full-length HMGB1, but also with the constructs containing the C-terminal end (i.e., A-Box+C-tail and B-Box+C-tail), as in the case of the results of immunofluorescence staining. Thus, the epitope of EV007156 was determined to be located in the C-terminal region. Then, the same experiment was also performed on S6 and G4. S6 and G4 were found to be reactive with the constructs containing B-Box (i.e., A-Box+B-Box, B-Box+C-tail, and B-Box alone), as in the case of the results of immunofluorescence staining. Thus, the epitopes of S6 and G4 were determined to be located in B-Box. This indicated that EV007156 had an epitope different from those of S6 and G4.

(d) Peptide Mapping (Dot Blotting)

Figure 18:
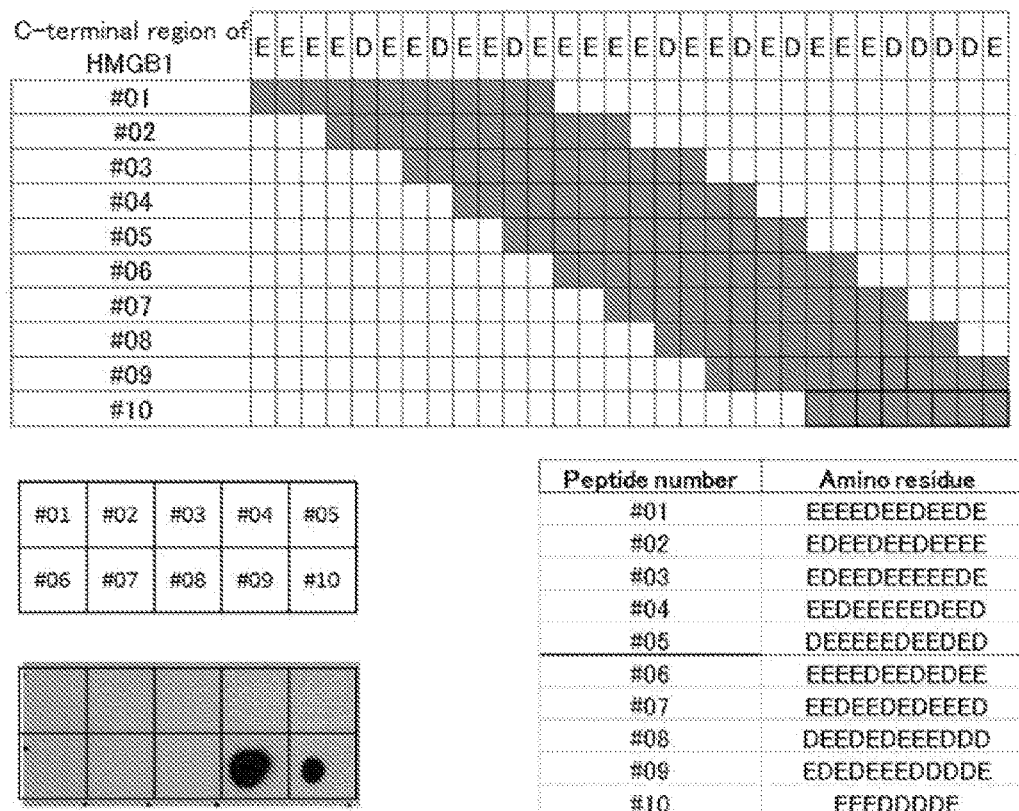
FIG. 18 shows the epitope mapping of EV007156 with synthetic peptides of the HMGB1 C-terminal region. Ten peptides #1 to #10 were synthesized and provided for dot blotting to detect which of the peptides was recognized by EV007156. The amount of peptide to be dotted is set to 4 μg/spot in all cases.

To identify the positions of amino acids where the epitope of EV007156 against HMGB1 was located from among those constituting the C-terminal end of HMGB1, peptide mapping was conducted. Namely, 9 types of 12-residue long amino acids at 3 residue intervals and the most C-terminal 8 residues, i.e., 10 peptides in total (#1. EEEEDEEDEEDE (SEQ ID NO: 51), #2. EDEEDEEDEEEE (SEQ ID NO: 52), #3. EDEEDEEEEEDE (SEQ ID NO: 53), #4. EEDEEEEEDEED (SEQ ID NO: 54), #5. DEEEEDEEDED (SEQ ID NO: 55), #6. EEEEDEEDEDEE (SEQ ID NO: 56), #7. EEDEEDEDEEED (SEQ ID NO: 57), #8. DEEDEDEEDDD (SEQ ID NO: 58), #9. EDEDEEEDDDDE (SEQ ID NO: 59), #10. EEEDDDDE (SEQ ID NO: 60)) were designed to cover all the amino acids constituting the C-terminal region of HMGB1. The peptides thus synthesized (SIGMA-ALDRICH, PEPScreen) were each dissolved at 4 mg/ml in a 0.1 M ammonium acetate solution and added dropwise at 4 µg/spot onto a nitrocellulose membrane. After drying, the membrane was blocked with 5% skimmed milk-TBST for 90 minutes. EV007156 was then reacted for 1 hour at a concentration of 1 µg/ml. Subsequently, HRP-labeled anti-human IgG antibody (MBL, #208) was reacted for 1 hour, followed by detection using ECL prime (GE Healthcare, RPN2232) (FIG. 18). The results indicated that EV007156 strongly recognized the most C-terminal region of HMGB1, i.e., #9. EDEDEEEDDDDE, and more particularly the most C-terminal 8 residues (#10. EEEDDDDE (SEQ ID NO: 60)).

Example 10

Effects of EV007156 on Sepsis Model Mice

Figure 19:
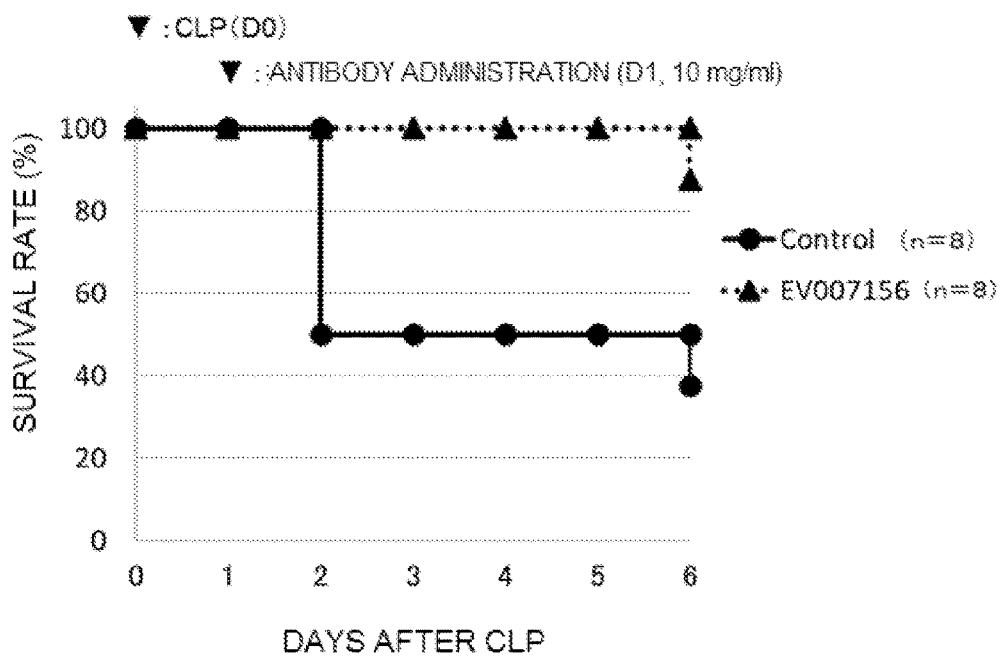
FIG. 19 shows the death protection effect provided by EV007156 administration in sepsis model mice. CLP-treated mice were administered with EV007156 at a dose of 10 mg/kg and their survival rates were calculated until 6 days after surgery. Solid circles: negative control group, and solid triangles: EV007156-administered group.

Whether EV007156 had the ability to protect sepsis-induced death was examined by calculating the survival rate after antibody administration. A mouse model of sepsis was prepared in accordance with the CLP method (cecal ligation and puncture, Lutterloh et al.). Namely, BALB/c mice (Japan SLC, Inc., female, 8 weeks of age, 16 mice) were anesthetized by being intraperitoneally administered with pentobarbital sodium (Nacalai Tesque, Inc., Japan, #26427-14) at a dose of 80 mg/kg. A median incision of about 1 cm was made to take out the cecum, about 90% of which was then ligated with a suture. Subsequently, a 23-gauge syringe needle (Terumo Corporation, Japan, #NN-2332S) was used to puncture the cecal wall once upward and once downward (twice in total). The cecum was returned into place in the abdominal cavity and the incision site was sutured with a suture. The incision site was rubbed with xylocaine (AstraZeneca) at a final concentration of 1% and 125 U/g baramycin (Ono Pharmaceutical Co., Ltd., Japan). Further, each mouse was intramuscularly administered with histamine (Nichi-Iko Pharmaceutical Co., Ltd., Japan) at a dose of 25 mg/kg. On the following day, at 24 hours after surgery, the mice were intraperitoneally administered with EV007156 at a dose of 10 mg/kg as an antibody-administered group. Likewise, in the control group, each mouse was intraperitoneally administered with physiological saline alone. Then, the state of each mouse was observed until 6 days after antibody administration to calculate the survival rate for each group (FIG. 19). As a result, at 48 hours after surgery, the survival rate was reduced to 50% in the control group, whereas the survival rate was maintained at 100% in the antibody-administered group receiving EV007156 administration. This survival rate maintenance was found to continue until 5 days after surgery. Moreover, the survival rate at 6 days after surgery was as high as 87.5% in the antibody-administered group, in comparison with 37.5% in the control group. This result indicated that administration of EV007156 significantly improved the mouse survival rate in CLP-induced sepsis model mice; and hence administration of this antibody was shown to be an extremely effective means against sepsis-induced death.

INDUSTRIAL APPLICABILITY

The humanized anti-HMGB1 antibody of the present invention or an antigen-binding fragment thereof has high affinity and neutralizing activity to mammalian HMGB1 in comparison with conventional human-derived anti-HMGB1 antibodies. Moreover, since the immunogenicity of the original rat antibody has been attenuated as a result of humanization, the humanized anti-HMGB1 antibody of the present invention or an antigen-binding fragment thereof is advantageous in application to humans and is useful as being able to provide new therapeutic and/or prophylactic methods for many serious HMGB1-related diseases.

The invention claimed is:

1. A humanized antibody specifically binding to an amino acid sequence (EEEDDDDE (SEQ ID NO: 60)) present in the C-terminal domain of HMGB1 protein, or an antigen-binding fragment thereof, which capable of neutralizing the biological activity of HMGB1 protein, comprising a heavy chain variable region (VH) and a light chain variable region (VL), wherein
   (i) the heavy chain variable region (VH) comprises:
      (a) an amino acid sequence of heavy chain CDR1 comprising the amino acid sequence of SEQ ID NO: 7;
      (b) an amino acid sequence of heavy chain CDR2 comprising the amino acid sequence of SEQ ID NO: 8;
      (c) an amino acid sequence of heavy chain CDR3 comprising the amino acid sequence of SEQ ID NO: 9;
      (d) amino acid sequences of SEQ ID Nos: 43, 44, 45, and 46 as amino acid sequences of FR1, FR2, FR3, and FR4, respectively, wherein the amino acid sequences of FR1, FR2, FR3, and FR4 optionally have mutations of deletion, substitution and/or addition of one or several amino acid residues in the amino acid sequences of SEQ ID NOs: 43, 44, 45 and 46, respectively; and
   (ii) the light chain variable region (VL) comprises:
      (a) an amino acid sequence of light chain CDR1 comprising the amino acid sequence of SEQ ID NO: 10,
      (b) an amino acid sequence of light chain CDR2 comprising the amino acid sequence of SEQ ID NO: 11;
      (c) an amino acid sequence of light chain CDR3 comprising the amino acid sequence of SEQ ID NO: 12; and
      (d) the light chain variable region (VL) further comprises the amino acid sequences of SEQ ID Nos: 47, 48, 49 and 50 as amino acid sequences of FR1, FR2, FR3, and FR4, respectively, wherein the amino acids sequences of FR1, FR2, FR3, and FR4 optionally have mutations of deletion, substitution, insertion, and/or addition of one to several amino acid residues in the amino acid sequences of SEQ ID NOs: 47, 48, 49, and 50, respectively.

2. The humanized antibody or antigen-binding fragment thereof of claim 1, wherein
   (i) the heavy chain variable region (VH) comprises an amino acid sequence in which the amino acid residues at positions 49 and 94 are alanine and alanine, respectively, and
   (ii) the light chain variable region (VL) comprises an amino acid sequence in which the amino acid residues at positions 44 and 46 are isoleucine and arginine, respectively.

3. The humanized antibody or antigen-binding fragment thereof of claim 1, wherein the class (subclass) of the humanized antibody is IgG1($\lambda$) or IgG2($\lambda$).

4. The humanized antibody or antigen-binding fragment thereof of claim 1, wherein the binding activity thereof to human HMGB1 protein (analyzed by ELISA assay) is 2-fold or higher than that of #10-22 chimeric antibody when compared at 250 ng/ml, wherein the #10-22 chimeric antibody comprises a heavy chain having the amino acid sequence of SEQ ID NO: 13 and a light chain having the amino acid sequence of SEQ ID NO: 14.

5. The humanized antibody or antigen-binding fragment thereof of claim 1, wherein the activity thereof required for 50% inhibition (IC50) of binding of human HMGB1 protein to RAGE is 5 µg/mL (about 33 nM) or less.

6. The antibody or antigen-binding fragment thereof of claim 1, wherein the activity thereof required for 50% inhibition (IC50) of HMGB1 protein-stimulated TNF-α release in human PBMCs is 0.02 µg/mL (about 0.13 nM) or less.

7. A pharmaceutical composition for use in the treatment or prevention of a HMGB1-related disease, said composition comprising the humanized antibody or antigen-binding fragment thereof of claim 1 and a pharmaceutically acceptable carrier.

8. The pharmaceutical composition according to claim 7 for use in treatment or prevention of an HMGB1-related diseases induced by HMGB1 released from cells.

9. The pharmaceutical composition according to claim 7 wherein the HMGB1-related disease is any one of cerebral infarction, cerebral edema, cerebral vasospasm, traumatic brain damage, atherosclerosis, neuropathic pain, sepsis, arthritis, acute lung trauma, cerebral ischemia, renal ischemia, and hepatic ischemia.

10. An isolated nucleic acid encoding the amino acid sequence of the humanized antibody of claim 1 or the antigen-binding fragment thereof.

11. A recombinant expression vector comprising the isolated nucleic acid according to claim 10.

12. A host cell transformed with the recombinant expression vector according to claim 11.

13. A humanized antibody specifically binding to an amino acid sequence (EEEDDDDE(SEQ ID NO: 60))present in the C-terminal domain of HMGB1 protein, or an antigen-binding fragment thereof, which is capable of neutralizing the biological activity of HMGB1 protein, comprising a heavy chain variable region (VH) and a light chain variable region (VL), wherein
   (i) the heavy chain variable region (VH) comprises an amino acid sequence having a 90% or more identity with the amino acid sequence of SEQ ID NO: 41, and
   (ii) the light chain variable region (VL) comprises an amino acid sequence having a 90% or more identity with the amino acid sequence of SEQ ID NO: 42.

14. The humanized antibody or antigen-binding fragment thereof of claim 13, wherein (i) the heavy chain variable region (VH) comprises the amino acid sequence of SEQ ID NO: 41, and
(ii) the light chain variable region (VL) comprises the amino acid sequence of SEQ ID NO: 42.

* * * * *